(12) United States Patent
Chow et al.

(10) Patent No.: US 10,111,854 B2
(45) Date of Patent: *Oct. 30, 2018

(54) SYNTHESIS AND USE OF AMINE-CONTAINING FLAVONOIDS AS POTENT ANTI-LEISHMANIAL AGENTS

(71) Applicant: The Hong Kong Polytechnic University, Hung Hom, Kowloon (HK)

(72) Inventors: Larry Ming-Cheung Chow, Kowloon (HK); Tak Hang William Chan, Kowloon (HK); Kin-Fai Chan, Kowloon (HK); Iris Lai King Wong, Kowloon (HK); Wing-Yiu Kan, Kowloon (HK)

(73) Assignee: The Hong Kong Polytechnic University, Kowloon (HK)

( * ) Notice: Subject to any disclaimer, the term of this patent is extended or adjusted under 35 U.S.C. 154(b) by 0 days.

This patent is subject to a terminal disclaimer.

(21) Appl. No.: 15/425,481

(22) Filed: Feb. 6, 2017

(65) Prior Publication Data

US 2017/0143665 A1    May 25, 2017

Related U.S. Application Data

(63) Continuation-in-part of application No. 14/632,647, filed on Feb. 26, 2015, now Pat. No. 9,562,037.

(60) Provisional application No. 61/945,077, filed on Feb. 26, 2014.

(51) Int. Cl.

| | | |
|---|---|---|
| A61K 31/352 | (2006.01) |
| A61K 31/496 | (2006.01) |
| A61K 31/443 | (2006.01) |
| A61K 31/4545 | (2006.01) |
| A61K 31/551 | (2006.01) |
| A61K 31/4439 | (2006.01) |
| A61K 31/444 | (2006.01) |
| A61K 31/4709 | (2006.01) |
| A61K 45/06 | (2006.01) |
| A61K 31/506 | (2006.01) |
| C07D 405/14 | (2006.01) |
| C07D 405/12 | (2006.01) |
| C07D 311/30 | (2006.01) |
| A61K 31/4433 | (2006.01) |

(52) U.S. Cl.
CPC .......... *A61K 31/352* (2013.01); *A61K 31/444* (2013.01); *A61K 31/4433* (2013.01); *A61K 31/4439* (2013.01); *A61K 31/4545* (2013.01); *A61K 31/4709* (2013.01); *A61K 31/496* (2013.01); *A61K 31/506* (2013.01); *A61K 31/551* (2013.01); *A61K 45/06* (2013.01); *C07D 311/30* (2013.01); *C07D 405/12* (2013.01); *C07D 405/14* (2013.01); *Y02A 50/409* (2018.01); *Y02A 50/411* (2018.01); *Y02A 50/414* (2018.01)

(58) Field of Classification Search
CPC .. C07D 311/30; C07D 405/12; C07D 405/14; A61K 31/352; A61K 31/4433; A61K 31/4439; A61K 31/444; A61K 31/4545; A61K 31/496; A61K 31/551; A61K 45/06
See application file for complete search history.

(56) References Cited

U.S. PATENT DOCUMENTS 8,980,848 B2 * 3/2015 Chan ................... C07D 311/30
514/27
9,562,037 B2 * 2/2017 Chow

OTHER PUBLICATIONS

Harborne and Williams, "Advances in flavonoid research since 1992", Phytochemistry, 55:481-504 (2000).
Singh, et al., "Natural product based leads to fight against leishmaniasis",Bioorg. Med. Chem., 22:18-45 (2014).
Weniger, et al.,"Comparative antiplasmodial, leishmanicidal and antitrypanosomal activities of several bioflavonoids", Phytomedicine, 13:176-80 (2006).
Wong, et al., "Flavonoid dimers as bivalent modulators for pentamidine and sodium stiboglucanate resistance in leishmania", Antimicrob Agents Chemother, 51:930-40 (2007).
Wong, et al., "Quinacrine and a novel apigenin dimer can synergistically increase the pentamidine susceptibility of the protozoan parasite Leishmania", J Antimicrob Chemother., 63:1179-90 (2009).
Wong, et al., "Flavonoid dimers as novel, potent antileishmanial agents", J Med Chem., 55:8891 902 (2012).
Wong, et al., In vitro and in vivo efficacy of novel flavonoid dimers against cutaneous leishmaniasis, Antimicrob Agents Chemother., 58:3379-88 (2014).

* cited by examiner

*Primary Examiner* — Erich A Leeser
(74) *Attorney, Agent, or Firm* — Pabst Patent Group LLP

(57) ABSTRACT

The present invention relates to novel series of amine-containing flavonoids and compositions containing the compounds, as well as the synthesis and the use of the same. The invention also relates to methods of treatment and prevention of diseases, in particular, parasitic infections including Leishmaniasis, comprising administration of the compounds.

17 Claims, 5 Drawing Sheets

SYNTHESIS AND USE OF AMINE-CONTAINING FLAVONOIDS AS POTENT ANTI-LEISHMANIAL AGENTS

CROSS REFERENCE TO RELATED APPLICATIONS

This application claims benefit of U.S. Ser. No. 14/632,647 filed Feb. 26, 2015, which claims benefit of U.S. Provisional Application No. 61/945,077, filed Feb. 26, 2014, which is hereby incorporated herein by reference in its entirety.

FIELD OF THE INVENTION

The present invention relates to a novel series of amine-containing flavonoids and to the treatment of parasitic infections including Leishmaniasis.

BACKGROUND OF THE INVENTION

Leishmaniasis is one of the six major parasitic diseases in the world. Different clinical manifestations of leishmaniasis include cutaneous, mucocutaneous, diffuse cutaneous, visceral and post kala azar dermal leishmaniasis (PKDL). Out of a total of 2 million annual cases of leishmaniasis, 500,000 of them belong to the visceral leishmaniasis (VL), the most serious and potentially fatal form of leishmaniasis (Ashford R W, et al., Parasitol Today. 1992; 8:104-5). VL is caused by *Leishmania donovani* in Indian subcontinent, Asia and Africa, and by *L. infantum* or *L. chagasi* in the Mediterranean region and South America. There are currently no vaccines available for leishmaniasis.

The primary method for treatment of leishmaniasis has been pentavalent antimonials ($Sb^V$):Pentostam (sodium stibogluconate; SSG) and Glucantime (meglumine antimoniate). However, large-scale antimony resistant cases have been reported in regions, including North Bihar of India. Antimonial drugs suffer from many problems including numerous side effects and a long treatment period (20 mg/kg in 2 divided doses for 30 days, intramuscular i.m. or intravenous i.v.).

Amphotericin B is normally considered a secondary treatment for VL, due to its potent antileishmanial activity. Although the use of Amphotericin B (in doses of 0.75-1 mg/kg for 15 to 20 treatments results in high cure rate, this drug suffers from the need for hospitalisation for prolonged periods, high-cost and high incidence of adverse side-effects. A liposomal formulation of amphotericin B (AmBisome® by Gilead) with lower nephrotoxicity has become available, however, this drug is not only expensive, it has other drawbacks including the need for intravenous administration and temperature instability (therefore requiring cold storage).

Paromomycin is an aminoglycoside that can be used alone or in combination with antimonials drugs. Intramuscular administration of paromomycin (15 mg/kg for 20 days) in a clinical trial in India demonstrated 94% efficacy (Sundar S, et al., N Engl J Med. 2007; 356:2571-81). Another antileishmanial agent, pentamidine, requires intramuscular or intravenous administration (2 to 3 mg/kg once a day or every second day for 4 to 7 doses), with higher doses up to 15 doses used for visceral leishmaniasis. The application of this drug is also limited by its toxicity. All of the above currently available treatment options necessitate parenteral administration, and/or hospitalization. Given the poor social infrastructure in the developing countries where most leishmaniasis are found, a chemotherapy-based disease eradication program will rely on the availability of oral drug(s) that can be self-administered without hospitalization.

Miltefosine is currently the only oral treatment available for VL. However, the use of miltefosine is associated with a number of limitations, including (i) potential teratogenicity, (ii) long treatment period of 28 days which leads to poor compliance, (iii) long residence time of miltefosine in patients' plasma which potentially can lead to emergence of miltefosine-resistant parasites, and (iv) high-cost.

In VL, resistance to SSG is a problem in Bihar of India, where half of the world's VL cases are reported. The efficacy of SSG (20 mg/kg/day for 28 days) has steadily dropped from 80% to 40% between 1988 and 2002 (Croft S L, et al. Clin Microbiol Rev. 2006; 19:111-26.). In India where VL is anthroponotic (as opposed to zoonotic in other regions), mono-therapy of miltefosine could lead to rapid emergence of resistance (Bryceson A., Trop Med Int Health. 2001; 6:928-34.).

Some natural flavonoids are known to have antileishmanial and anti-malarial activities as described in Phytochemistry, 55, 481-504 (2000) and Bioorg. Med. Chem., 22, 18-45 (2014). Nevertheless, due to their unsatisfactory efficacy and bioavailability, usage of these naturally occurring compounds is limited.

More recent studies have demonstrated that amine-linked flavonoid dimers are highly effective anti-promastigotes and anti-amastigotes agents with $IC_{50}$ ranging from 0.2 to 0.63 μM, rendering them as preferred compounds over naturally occurring flavonoids (Wong I L K, et al., Journal of Medicinal Chemistry. 2012; 55, 8891-8902). One of the preferred potent flavonoid dimers, compound 39 (as shown in FIG. 1) disclosed in Wong I L K et al., which has the following structure:

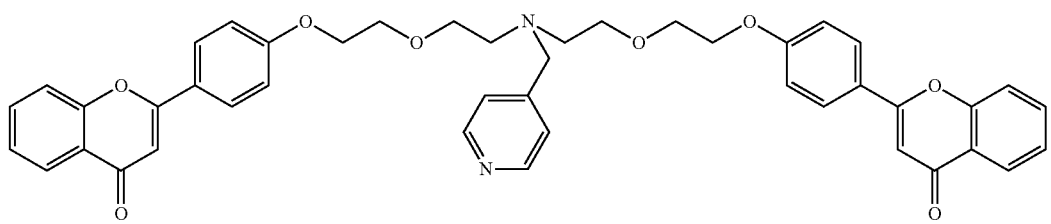

is also shown to be effective in reducing foot pad lesion size in *L. amazonensis* cutaneous leishmaniasis murine model (Wong I L K, et al., Antimicrob Agents Chemother. 2014, 58, 3379-3388). However, amine-linked flavonoid dimers are expected to have poor oral bioavailability, and hence would not provide a solution to the problems encountered in the treatment of leishmaniasis as descried above.

There is a need to provide compounds that are able to overcome at least one, but preferably more, of the problems of the prior art. It would be desirable to provide new antileishmanial agents that are effective and safe, and preferably orally bioavailable. It would be desirable to have new antileishmanial agents that are effective against both promastigotes and amastigotes.

It is an object of the invention to provide new compounds having antileishmanial activity particularly, leishmaniasis in animals with low toxicity toward the host.

It is another object of this invention to provide a method of treating mammals which are infested with protozoa parasites of the genus *Leishmania*, and to provide a method of preventing mammals, including humans, from parasitic infestation of parasites of the genus *Leishmania*.

SUMMARY OF THE INVENTION

The present invention provides novel compounds with highly potently anti-leishmaniasis activity, whilst displaying low toxicity. The invention provides compounds which are water-soluble and orally bioavailable, and suitable for formulation into anti-leishmaniasis compositions suitable for oral administration, whilst achieving the desired efficacy.

Amine-linked flavonoid dimers are disclosed in prior studies to be sparingly soluble in aqueous medium. Their poor oral bioavailability is confirmed by in vivo study in mice. In a bioavailability study, oral feeding of flavonoid dimer 39 (in 50% PEG) into Balb/c mice was compared with intravenous (i.v.) administration of 39 (also in 50% PEG). Plasma concentration of 39 was determined 30 minutes after oral feeding or i.v. administration. Oral feeding of 39 only resulted in a plasma level<1% of that of i.v. group, suggesting that oral bioavailability of 39 is low. Such low bioavailability precluded 39 from being used as an oral antileishmanial agent in the future.

One aspect of the invention relates to novel synthetic compounds with antileishmanial activities which are useful in the treatment and/or prevention of a parasitic disease caused by genus *Leishmania*, for example, infestation of parasites selected from the group consisting of *L. donovani*, *L. amazonensis*, *L. tarentolae*, *L. tropica*, *L. enriettii*, *L. mexicana*, and *L. major*. The disclosed compounds are expected to be effective against both visceral and cutaneous *Leishmania*, The compounds exhibit high potency (with both anti-promastigote activity and amastigote activity) compared to known anti-leishmanial agents, whilst displaying low cytotoxicity. In particular, the synthetic amine containing flavonoids of general structure FM are potent in vitro ($IC_{50}$=0.4-10 µM against promastigotes and $IC_{50}$=<0.37-10 µM against amastigotes), safe ($IC_{50}$ against fibroblasts=33-100 µM) and, most importantly, water soluble and orally bioavailable.

The present invention provides novel flavonoid derivatives which are more "druggable" and preferably orally bioavailable, thereby overcoming the problems of low aqueous solubility and oral bioavailability displayed by flavonoid dimers like compound 39.

The present invention provides monomeric flavonoids modified with amine functions to improve their activities relative to luteolin and quercetin. The new series of amine-containing flavonoid monomers (FM) are found to be more "druggable" and, making them highly desirable as new candidates for the development of new oral treatment for leishmaniasis, including visceral leishmaniasis. Provision of a new orally active drug translates to advantageous including: reduced cost in treatment, increased patient compliance, and increased access to treatment as hospitalization is not required. These benefits are especially prominent in the treatment of leishmaniasis, as infections are mainly observed in developing countries where medical options are limited.

BRIEF DESCRIPTION OF THE DRAWINGS

Particular embodiments of the present invention will now be explained by way of example and with reference to the accompanying drawings, in which:

FIG. 1A shows ROS levels in RAW264.7 cells exposed to 10 µM of compounds as function of incubation time. FIG. 1B shows ROS levels in RAW264.7 cells exposed to 30 µM of compounds as a function of incubation time, wherein a 2.1-fold increase in intracellular ROS level was observed in RAW264.7 cells only upon exposure to the FM09 for 46 hr. FIG. 1C shows ROS levels in *L. amazonensis* promastigotes exposed to 30 µM of compounds as a function of incubation time wherein both FM09 and amphotericin B showed a time-dependent increase in the intracellular ROS level.

FIG. 2A shows the rhodamine 123 level of promastigotes after treatment with FM09 for 24 hr and FIG. 2B shows the % of survivors determined using MTS assay after incubation with FM09 for 24 hr. FIG. 2C shows the rhodamine 123 level of promastigotes after treatment with FM09 for 48 hr and FIG. 2D shows the % of survivors determined using MTS assay after incubation with FM09 for 48 hr.

DETAILED DESCRIPTION OF THE INVENTION

Figure 1A:
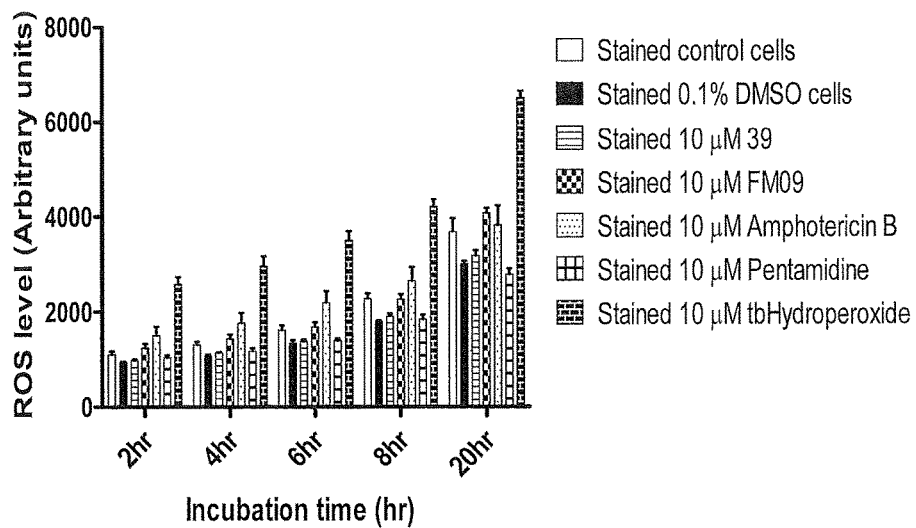
FIG. 1A-C shows the effect of amine-linked flavonoid dimer 39 on reactive oxygen species (ROS) levels of RAW264.7 and *L. amazonensis* promastigote, as compared to amine-containing flavonoid monomer FM09 and known antileishmanial compounds.

While the making and using of various embodiments are discussed below, it should be appreciated that the specific embodiments discussed herein are merely illustrative of specific ways of making and using the invention and should not be construed as to limit the scope of the invention.

The compounds of the present invention are represented by the general formula (also referred as FM) of:

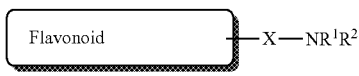

wherein:
the flavonoid is selected from the group consisting of flavone, flavonol, flavanone, and isoflavonoid;

X is a linker, wherein each linker independently comprises one or more groups selected from the group consisting of alkylene, ethyleneoxy, propyleneoxy, butyleneoxy, alkylC(O)—, ethylene amine, propylene amine, butylene amine, alkylcyclic amine, alkylcyclic diamine or a combination thereof;

$R^1$ is independently selected from the group consisting of H, alkyl, alkenyl, alkynyl, hydroxyalkyl, alkoxyalkyl, hydroxyalkenyl, hydroxyalkynyl, alkoxyalkenyl, alkoxyalkynyl, aminoalkyl, aminoalkenyl, aminoalkynyl, cycloalkyl, heterocycloalkyl, cycloalkenyl, heterocycloalkenyl, aryl, heteroaryl, —$(CH_2)_n$-aryl, —$(CH_2)_n$-heteroaryl, —$(CH_2)_n$-pyrimidyl, —$(CH_2)_n$-quinolyl, —$(CH_2)_n$-cycloalkyl, $(CH_2)_n$-cycloalkenyl, —$(CH_2)_n$-heterocycloalkyl, —$(CH_2)_n$-heterocycloalkenyl, —C(O)-alkyl, —C(O)-aryl, —C(O)-heteroaryl, —C(O)-cycloalkyl, —C(O)-cycloalkenyl, —C(O)—heterocycloalkyl, —C(O)-heterocycloalkenyl, —C(O)O-alkyl, —C(O)O-aryl, —C(O)O— heteroaryl, —C(O)O-cycloalkyl, —C(O)O-cycloalkenyl, —C(O)O-heterocycloalkyl, —C(O)O-heterocycloalkenyl, —$SO_2$alkyl, —$SO_2$aryl, —$SO_2$-heteroaryl, —$SO_2$cycloalkyl, —$SO_2$heterocycloalkyl, any of which may be optionally substituted;

$R^2$ is independently selected from the group consisting of H, alkyl, alkenyl, alkynyl, hydroxyalkyl, alkoxyalkyl, hydroxyalkenyl, hydroxyalkynyl, alkoxyalkenyl, alkoxyalkynyl, aminoalkyl, aminoalkenyl, aminoalkynyl, cycloalkyl, heterocycloalkyl, cycloalkenyl, heterocycloalkenyl, aryl, heteroaryl, —$(CH_2)_n$-aryl, —$(CH_2)_n$-heteroaryl, —$(CH_2)_n$-pyrimidyl, —$(CH_2)_n$-quinolyl, —$(CH_2)_n$-cycloalkyl, $(CH_2)_n$-cycloalkenyl, —$(CH_2)_n$-heterocycloalkyl, —$(CH_2)_n$-heterocycloalkenyl, —C(O)-alkyl, —C(O)-aryl, —C(O)-heteroaryl, —C(O)-cycloalkyl, —C(O)-cycloalkenyl, —C(O)—heterocycloalkyl, —C(O)-heterocycloalkenyl, —C(O)O-alkyl, —C(O)O-aryl, —C(O)O— heteroaryl, —C(O)O-cycloalkyl, —C(O)O-cycloalkenyl, —C(O)O-heterocycloalkyl, —C(O)O-heterocycloalkenyl, —$SO_2$alkyl, —$SO_2$aryl, —$SO_2$-heteroaryl, —$SO_2$cycloalkyl, —$SO_2$heterocycloalkyl, any of which may be optionally substituted;

alternatively, $NR^1R^2$ form a cyclic compound with a general structure of —$(CH_2)_n$—Y—$(CH_2)_m$- wherein Y is $CH_2$, O, or NR, any of which may be optionally substituted.

wherein n and m are independently integers between 1 and 6;

or is a pharmaceutically acceptable salt or solvate thereof.

In a preferred embodiment, $R^1$ is independently selected from hydrogen, methyl, benzyl, 2-pyridinyl-$CH_2$—, or 4-pyridinyl-$CH_2$—.

In a preferred embodiment, $R^2$ is independently selected from hydrogen, methyl, benzyl, 2-pyridinyl-$CH_2$—, or 4-pyridinyl-$CH_2$—.

In a preferred embodiment, $R^1$ and $R^2$ are each independently selected from —$(CH_2)_n$-pyrimidyl and —$(CH_2)_n$-quinolyl where n is an integer between 1 and 6; preferably n=1.

In a preferred embodiment, $R^1$ and/or $R^2$ is 2-pyridinyl-$CH_2$ or 4-pyridinyl-$CH_2$—.

In a preferred embodiment, $R^1$ and $R^2$ are both 2-pyridinyl-$CH_2$.

In a preferred embodiment, $R^1$ and $R^2$ are both H.

In a preferred embodiment, $R^1$ and/or $R^2$ is pyrimidyl-$CH_2$—, quinolyl-$CH_2$—, 2-pyridinyl-$CH_2$, or 4-pyridinyl-$CH_2$— which may each be optionally substituted at the pyrimidyl, quinolyl, or pyridinyl group and/or the —$CH_2$— group with one or more optionally substituted $C_1$-$C_{30}$ alkyl, optionally substituted $C_1$-$C_{30}$ alkoxy, halogen, optionally substituted aryl, or optionally substituted heteroaryl groups.

In a preferred embodiment, X is a linker selected from the group consisting of ethyleneoxy, propyleneoxy, and butyleneoxy.

In a preferred embodiment, X is a linker selected from the group consisting of 4-piperidinylmethoxy, 4-piperidinylethoxy, 1,4-diazepan-1-ylethoxy, or piperazinylethoxy.

In a preferred embodiment, $R^1$ or $R^2$ is 4-pyridinyl-$CH_2$— and X is a linker with 4-piperidinylmethoxy or 1,4-diazepan-1-ylethoxy.

In a preferred embodiment, $R^1$ or $R^2$ is 4-pyridinyl-$CH_2$— and X is a linker with 4-piperidinylmethoxy, 4-piperidinylethoxy, or piperazinylethoxy.

In a preferred embodiment, $R^1$ or $R^2$ is 2-pyridinyl-$CH_2$— and X is a linker with 4-piperidinylmethoxy or 1,4-diazepan-1-ylethoxy. In some embodiments the pyridinyl and/or the —$CH_2$— group with one or more $C_1$-$C_{30}$ alkyl, $C_1$-$C_{30}$ alkoxy, halogen, aryl, or heteroaryl groups.

Exemplary compounds of the amine-containing flavonoid monomers are provided below:

| | | |
|---|---|---|
| FM01 | 2-(4-(2-(4-(pyridin-4-ylmethyl)piperazin-1-yl)ethoxy)phenyl)-4H-chromen-4-one | 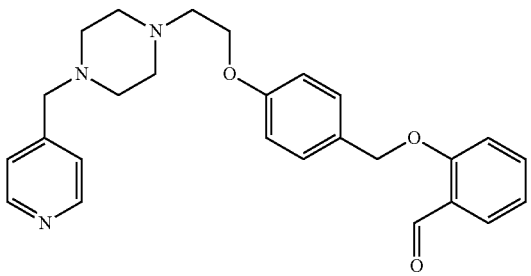 |

FM01
$C_{27}H_{27}N_3O_3$
442

| | | |
|---|---|---|
| FM02 | 2-(4-(2-(methyl(2-(methyl(pyridin-4-ylmethyl)amino)ethyl)amino)ethoxy)phenyl)-4H-chromen-4-one | 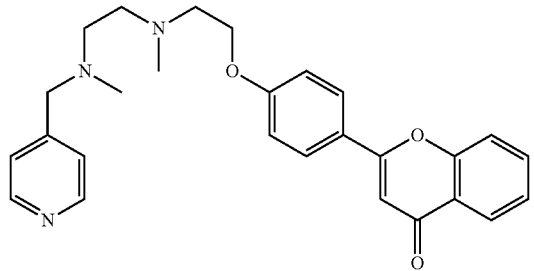<br>FM02<br>$C_{27}H_{29}N_3O_3$<br>444 |
| FM03 | N-(2-(2-(4-(4-oxo-4H-chromen-2-yl)phenoxy)ethoxy)ethyl)isonicotinamide | 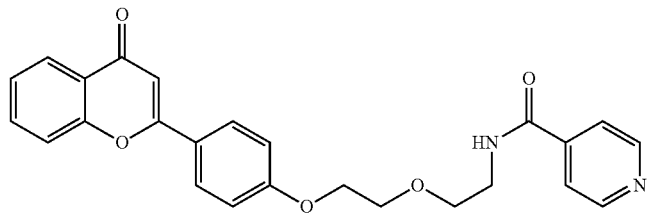<br>FM03<br>$C_{25}H_{22}N_2O_5$<br>430 |
| FM04 | 2-(4-(2-(2-(benzylamino)ethoxy)ethoxy)phenyl)-4H-chromen-4-one | 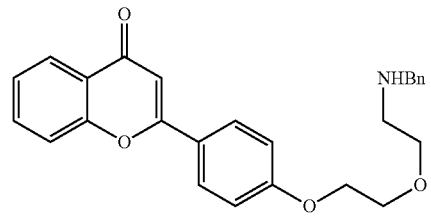<br>FM04<br>$C_{26}H_{25}NO_4$<br>415 |
| FM05 | 2-(4-(2-(1-(pyridin-4-ylmethyl)piperidin-4-yl)ethoxy)phenyl)-4H-chromen-4-one | 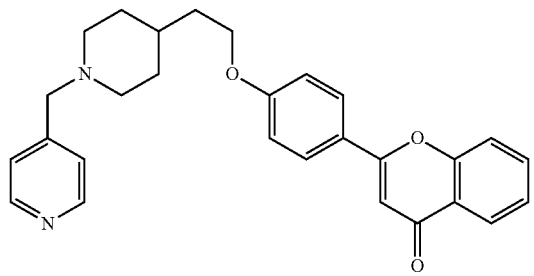<br>FM05<br>$C_{28}H_{28}N_2O_3$<br>441 |

| | | |
|---|---|---|
| FM06 | 2-(4-(2-(2-(dimethylamino)ethoxy)ethoxy)phenyl)-4H-chromen-4-one | 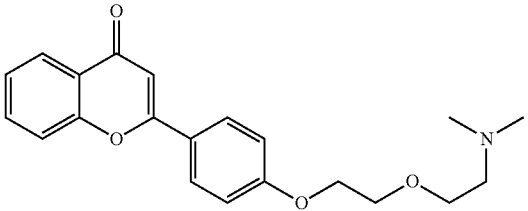<br>FM06<br>$C_{21}H_{23}NO_4$<br>353 |
| FM07 | N-(2-(2-(4-(4-oxo-4H-chromen-2-yl)phenoxy)ethoxy)ethyl)methanesulfonamide | 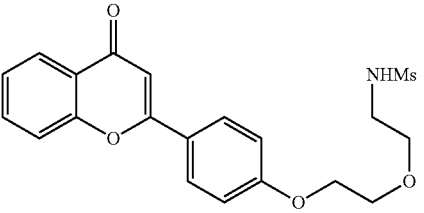<br>FM07<br>$C_{20}H_{21}NO_6S$<br>403 |
| FM08 | 2-(4-(2-(2-((pyridin-4-ylmethyl)amino)ethoxy)ethoxy)phenyl)-4H-chromen-4-one | 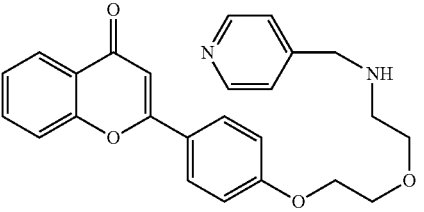<br>FM08<br>$C_{25}H_{24}N_2O_4$<br>416 |
| FM09 | 2-(4-(2-(2-(bis(pyridin-2-ylmethyl)amino)ethoxy)ethoxy)phenyl-4H-chromen-4-one | 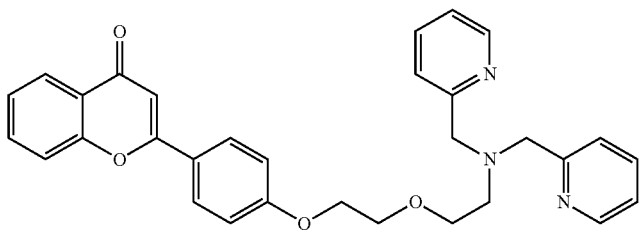<br>FM09<br>$C_{31}H_{29}N_3O_4$<br>508 |
| FM10 | 2-(4-(2-oxo-2-(piperazin-1-yl)ethoxy)phenyl)-4H-chromen-4-one | 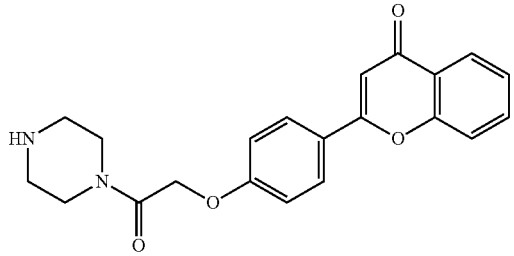<br>FM10<br>$C_{21}H_{20}N_2O_4$<br>364 |

-continued
| | | |
|---|---|---|
| FM11 | 2-(4-(2-(1,4-diazepan-1-yl)-2-oxoethoxy)phenyl)-4H-chromen-4-one | 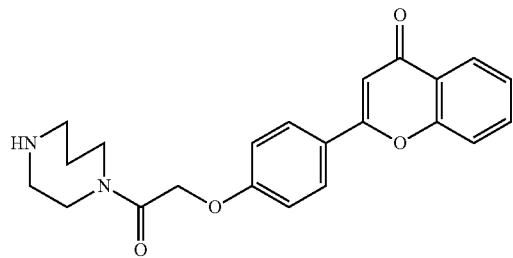<br>FM11<br>C$_{22}$H$_{22}$N$_2$O$_4$<br>378 |
| FM12 | 2-(4-(2-oxo-2-(4-(pyridin-4-ylmethyl)piperazin-1-yl)ethoxy)phenyl)-4H-chromen-4-one | 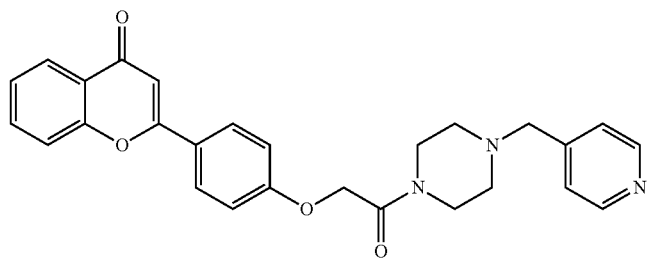<br>FM12<br>C$_{27}$H$_{25}$N$_3$O$_4$<br>456 |
| FM13 | 2-(4-((1-(pyridin-4-ylmethyl)piperidin-4-yl)methoxy)phenyl)-4H-chromen-4-one | 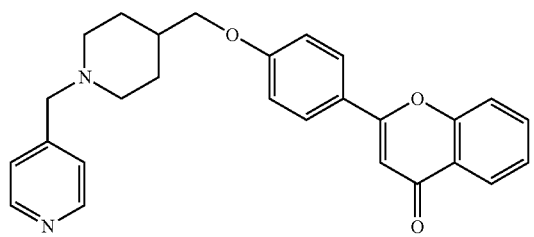<br>FM13<br>C$_{27}$H$_{26}$N$_2$O$_3$<br>427 |
| FM14 | 2-(4-(2-(4-(pyridin-4-ylmethyl)-1,4-diazepan-1-yl)ethoxy)phenyl)-4H-chromen-4-one | 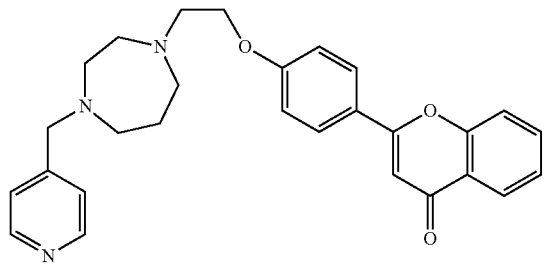<br>FM14<br>C$_{28}$H$_{29}$N$_3$O$_3$<br>456 |

-continued

| | | |
|---|---|---|
| FM15 | 2-(4-(2-oxo-2-(4-(pyridin-4-ylmethyl)-1,4-diazepan-1-yl)ethoxy)phenyl)-4H-chromen-4-one | 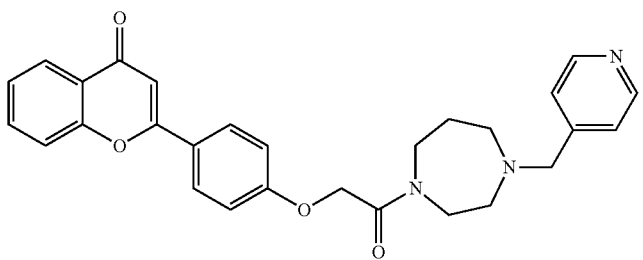<br>FM15<br>C$_{28}$H$_{27}$N$_3$O$_4$<br>470 |
| FM16 | 2-(4-(2-(4-isonicotinoyl-piperazin-1-yl)-2-oxoethoxy)phenyl)-4H-chromen-4-one | 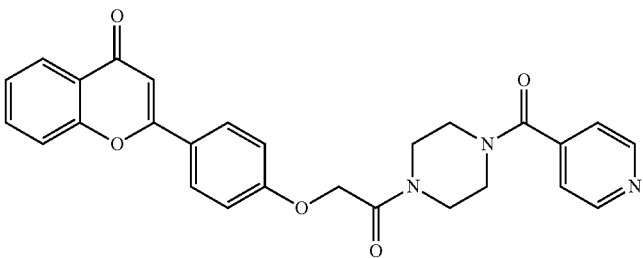<br>FM16<br>C$_{27}$H$_{23}$N$_3$O$_5$<br>469 |
| FM17 | 2-(4-(2-(1-(pyridin-4-ylmethyl)piperidin-2-yl)ethoxy)phenyl)-4H-chromen-4-one | 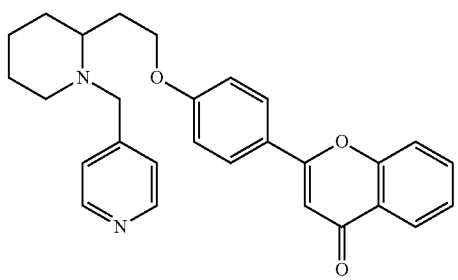<br>FM17<br>C$_{28}$H$_{28}$N$_2$O$_3$<br>441 |
| FM18 | (S)-2-(4-((1-(pyridin-4-ylmethyl)pyrrolidin-2-yl)methoxy)phenyl)-4H-chromen-4-one | 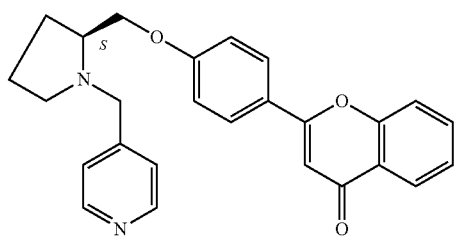<br>FM18<br>C$_{26}$H$_{24}$N$_2$O$_3$<br>412 |

-continued

| FM19 | 2-(4-(2-(2-(dibenzylamino)ethoxy)ethoxy)phenyl)-4H-chromen-4-one | 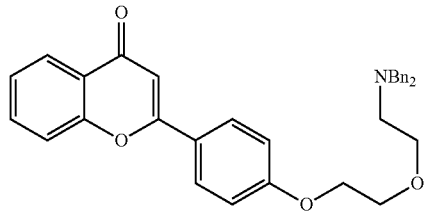 FM19<br>C₃₃H₃₁NO₄<br>506 |

| FM20 | 2-(4-(2-(2-(amino)ethoxy)ethoxy)phenyl)-4H-chromen-4-one | 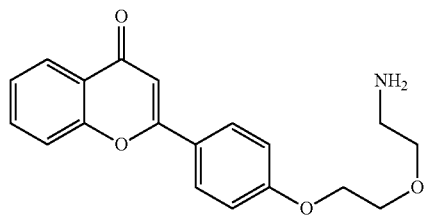 FM20<br>C₁₉H₁₉NO₄<br>Mol. Wt.: 325 |

| FM21 (monomeric form of dimer 39) | 2-(4-(2-(2-((pyridin-4-ylmethyl)(2-hydroxy-2-ethoxyethyl)amino)ethoxy)ethoxy)phenyl)-4H-chromen-4-one | 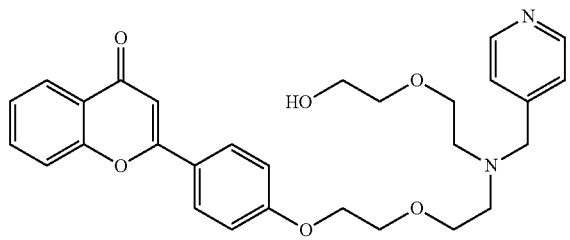 FM21<br>C₂₉H₃₂N₂O₆<br>Exact Mass: 504.23 |

| FM09a | 2-(4-(2-(2-(bis((3,4-dimethoxypyridin-2-yl)methyl)amino)ethoxy)ethoxy)phenyl)-4H-chromen-4-one | 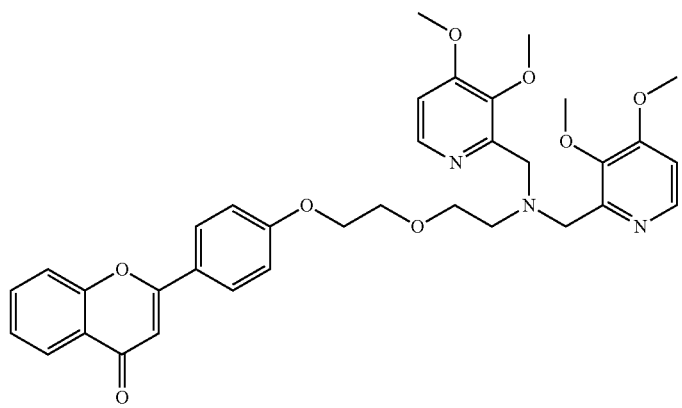 FM09a<br>C₃₅H₃₇N₃O₈<br>Exact Mass: 627.26 |

-continued
| FM09b | 2-(4-(2-(2-(bis(pyridin-3-ylmethyl)amino)ethoxy)ethoxy)phenyl)-4H-chromen-4-one | 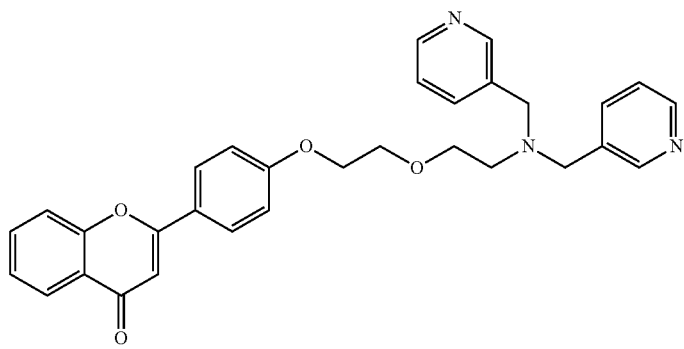 |
FM09b
C$_{31}$H$_{29}$N$_3$O$_4$
Exact Mass: 507.22
| FM09c | 2-(4-(2-(2-(bis((3-fluoropyridin-2-yl)methyl)amino)ethoxy)ethoxy)phenyl)-4H-chromen-4-one | 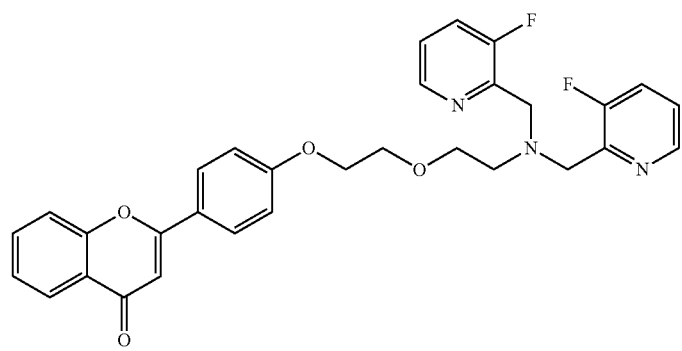 |
FM09c
C$_{31}$H$_{27}$F$_2$N$_3$O$_4$
Exact Mass: 543.20
| FM09d | 2-(4-(2-(2-(bis(pyrimidin-2-ylmethyl)amino)ethoxy)ethoxy)phenyl)-4H-chromen-4-one | 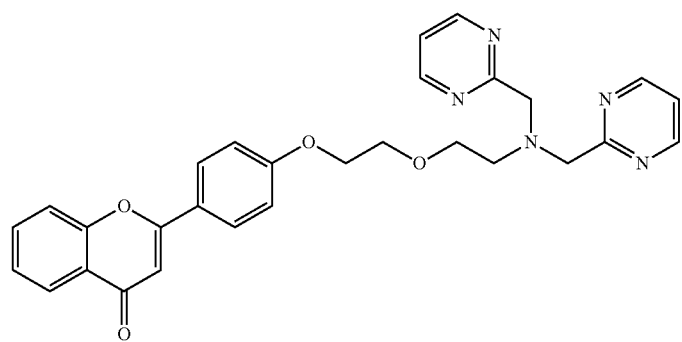 |
FM09d
C$_{29}$H$_{27}$N$_5$O$_4$
Exact Mass: 509.21

-continued

| | | |
|---|---|---|
| FM09e | 2-(4-(2-(2-(bis((6-methylpyridin-2-yl)methyl)amino)ethoxy)ethoxy)phenyl)-4H-chromen-4-one | 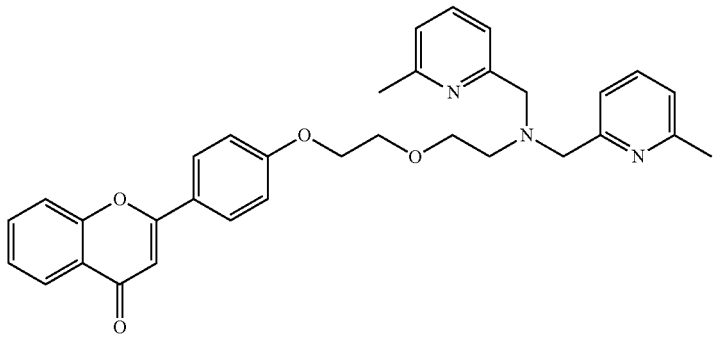<br>FM09e<br>C₃₃H₃₃N₃O₄<br>Exact Mass: 535.25 |
| FM09g | 2-(4-(2-(2-(bis((3-chloropyridin-2-yl)methyl)amino)ethoxy)ethoxy)phenyl)-4H-chromen-4-one | 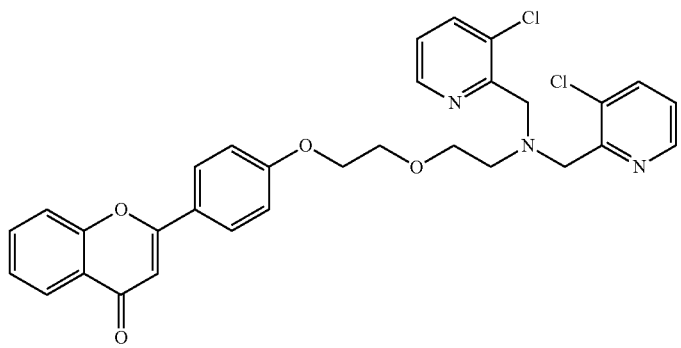<br>FM09g<br>C₃₁H₂₇Cl₂N₃O₄<br>Exact Mass: 575.14 |
| FM09h | 2-(4-(2-(2-(bis((3-methyl-4-(2,2,2-trifluoroethoxy)pyridin-2-yl)methyl)amino)ethoxy)ethoxy)phenyl)-4H-chromen-4-one | 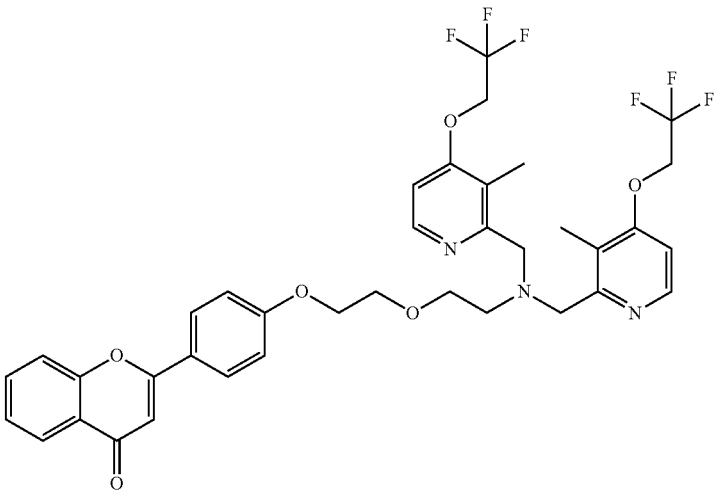<br>FM09h<br>C₃₇H₃₅F₆N₃O₆<br>Exact Mass: 731.24 |

| | | |
|---|---|---|
| FM09i | 2-(4-(2-(2-(bis((4-methoxy-3,5-dimethylpyridin-2-yl)methyl)amino)ethoxy)ethoxy)phenyl)-4H-chromen-4-one | 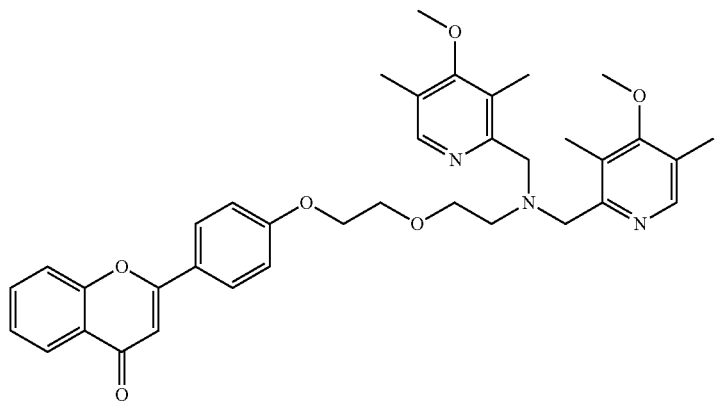 |
FM09i
$C_{37}H_{41}N_3O_6$
Exact Mass: 623.30
| | | |
|---|---|---|
| FM09k | 2-(4-(2-(2-(bis((4-(3-methoxypropoxy)-3-methylpyridin-2-yl)methyl)amino)ethoxy)ethoxy)phenyl)-4H-chromen-4-one | 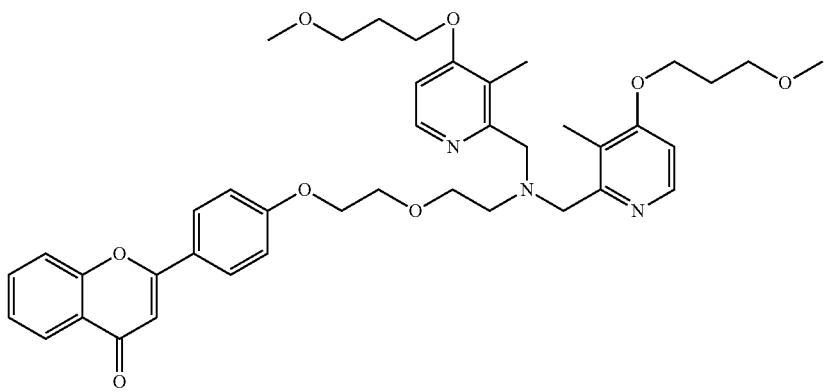 |
FM09k
$C_{41}H_{49}N_3O_8$
Exact Mass: 711.35
| | | |
|---|---|---|
| FM09l | 2-(4-(2-(2-(bis(quinolin-2-ylmethyl)amino)ethoxy)ethoxy)phenyl)-4H-chromen-4-one | 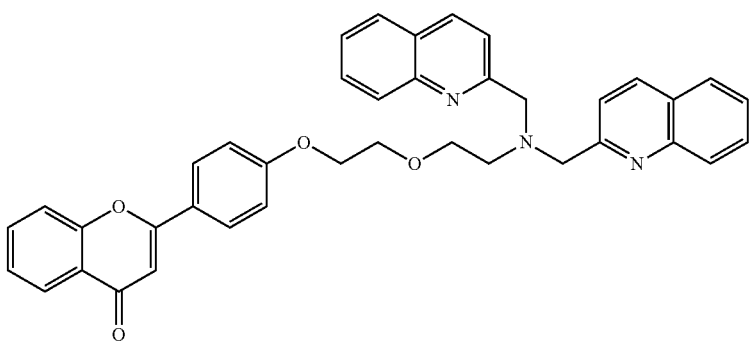 |
FM09l
$C_{39}H_{33}N_3O_4$
Exact Mass: 607.25

| | | |
|---|---|---|
| FM09m | 2-(4-(2-(2-((pyridin-2-ylmethyl)amino)ethoxy)ethoxy)phenyl)-4H-chromen-4-one | 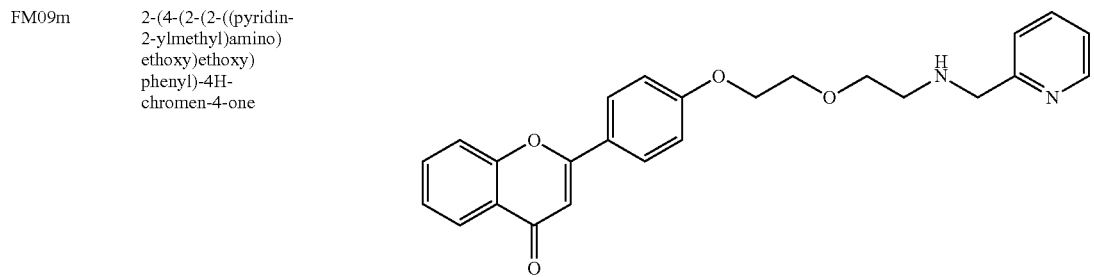<br>FM09m<br>C25H24N2O4<br>Exact Mass: 416.17 |
| FM09p | 2-(4-(2-(2-((di(pyridin-2-yl)methyl)amino)ethoxy)ethoxy)phenyl)-4H-chromen-4-one | 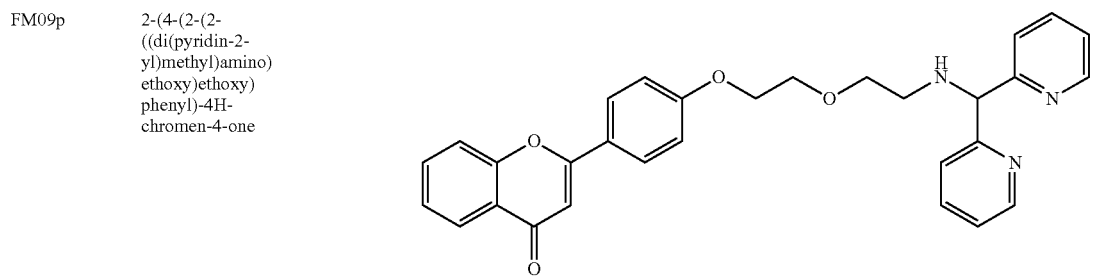<br>FM09p<br>C30H27N3O4<br>Exact Mass: 493.20 |
| FM09am | 2-(4-(2-(2-(((3,4-dimethoxypyridin-2-yl)methyl)amino)ethoxy)ethoxy)phenyl)-4H-chromen-4-one | 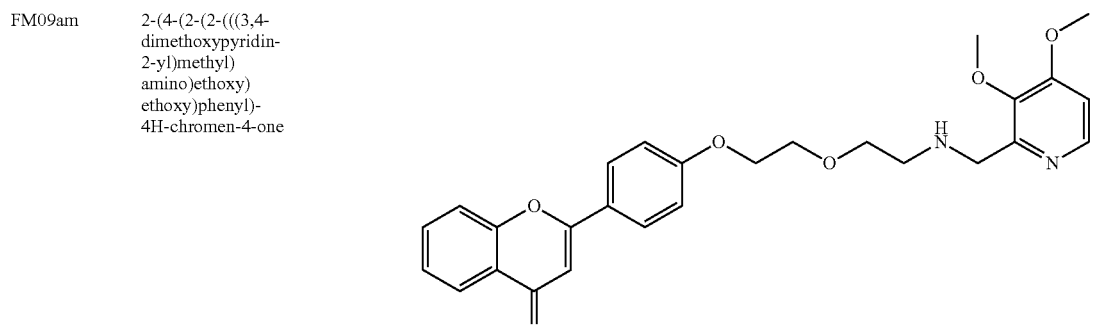<br>FM09am<br>C27H28N2O6<br>Exact Mass: 476.19 |
| FM01a | 2-(4-(2-(4-(pyridin-2-ylmethyl)piperazin-1-yl)ethoxy)phenyl)-4H-chromen-4-one | 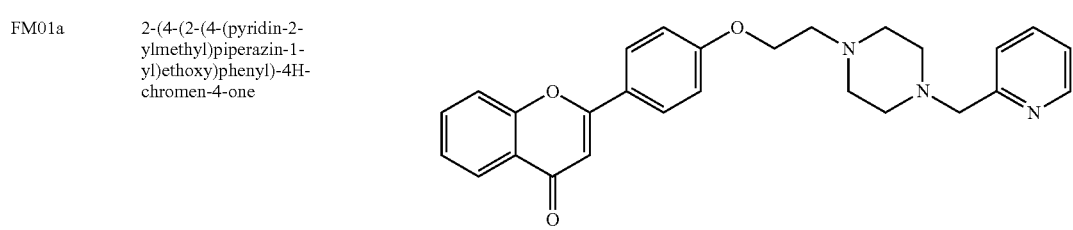<br>FM01a<br>C27H27N3O3<br>Exact Mass: 441.21 |

-continued

| | | |
|---|---|---|
| FM01b | 2-(4-(2-(4-((3,4-dimethoxypyridin-2-yl)methyl)piperazin-1-yl)ethoxy)phenyl)-4H-chromen-4-one | FM01b<br>$C_{29}H_{31}N_3O_5$<br>Exact Mass: 501.23 |
| FM05a | 2-(4-(2-(1-(pyridin-2-ylmethyl)piperidin-4-yl)ethoxy)phenyl)-4H-chromen-4-one | FM05a<br>$C_{28}H_{28}N_2O_3$<br>Exact Mass: 440.21 |
| FM05b | 2-(4-(2-(1-((3,4-dimethoxypyridin-2-yl)methyl)piperidin-4-yl)ethoxy)phenyl)-4H-chromen-4-one | FM05b<br>$C_{30}H_{32}N_2O_5$<br>Exact Mass: 500.23 |

For the purpose of the present invention the following terms are defined below:

The use of the word "a" or "an" when used in conjunction with the term "comprising" in the claims and/or the specification may mean "one", but it is also consistent with the meaning of "one or more", "at least one", and "one or more than one". Similarly, the word "another" may mean at least a second or more.

As used in this specification and claim(s), the words "comprising" (and any form of comprising, such as "comprise" and "comprises"), "having" (and any form of having, such as "have" and "has"), "including" (and any form of including, such as "include" and "includes") or "containing" (and any form of containing, such as "contain" and "contains"), are inclusive or open-ended and do not exclude additional, unrecited elements or process steps.

The terms "compound 39" or "dimer 39" or "39", as used herein, refer to amine-linked flavonoid dimer, compound 39, described in Wong I L K, et al., Journal of Medicinal Chemistry. 2012; 55, 8891-8902, having chemical structure shown below:

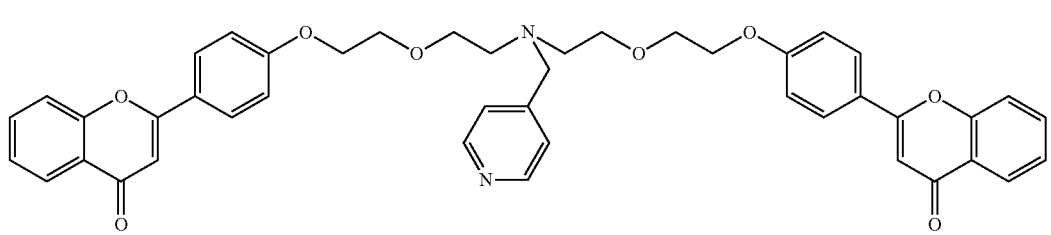

39

The terms "39 monomer" or "monomeric version of 39", as used herein, refer to 2-(4-(2-(2-((pyridin-4-ylmethyl)(2-hydroxy-2-ethoxyethyl) amino)ethoxy)ethoxy)phenyl)-4H-chromen-4-one, also named as compound FM21 herein.

The term "alkyl group", as used herein, is understood as referring to a saturated, monovalent unbranched or branched hydrocarbon chain. Examples of alkyl groups include, but are not limited to, C1-10 alkyl groups, preferably C1-6alkyl and most preferably C1-4alkyl. Examples of alkyl groups include, but are not limited to, methyl, ethyl, propyl, isopropyl, 2-methyl-1-propyl, 2-methyl-2-propyl, 2-methyl-1-butyl, 3-methyl-1-butyl, 2-methyl-3-butyl, 2,2-dimethyl-1-propyl, 2-methyl-1-pentyl, 3-methyl-1-pentyl, 4-methyl-1-pentyl, 2-methyl-2-pentyl, 3-methyl-2-pentyl, 4-methyl-2-pentyl, 2,2-dimethyl-1-butyl, 3,3-dimethyl-1-butyl, 2-ethyl-1-butyl, butyl, isobutyl, t-butyl, pentyl, isopentyl, neopentyl, hexyl, heptyl, octyl, nonyl and decyl. The term "alkyl" is also meant to include alkyls in which one or more hydrogen atom is replaced by a halogen, i.e., an alkylhalide, for example, but not exclusively, C1-C10-haloalkyl such as chloromethyl, dichloromethyl, trichloromethyl, fluoromethyl, difluoromethyl, trifluoromethyl, chlorofluoromethyl, dichlorofluoromethyl, chlorodifluoromethyl, 1-fluoroethyl, 2-fluoroethyl, 2,2-difluoroethyl, 2,2,2-trifluoroethyl, 2-chloro-2-fluoroethyl, 2-chloro-2,2-difluoroethyl, 2,2-dichloro-2-fluoroethyl, 2,2,2-trichloroethyl and pentafluoroethyl.

The term "aryl" represents a carbocyclic moiety containing at least one benzenoid-type ring (i.e., may be monocyclic or polycyclic). Preferably "aryl" has 6 to 10 carbon atoms. Examples include but are not limited to phenyl, tolyl, dimethylphenyl, aminophenyl, anilinyl, naphthyl, anthryl, phenanthryl or biphenyl.

The term "aryloxy" represents an aryl moiety, which is covalently bonded to the adjacent atom through an oxygen atom. Examples include but are not limited to phenoxy, dimethylphenoxy, aminophenoxy, anilinoxy, naphthoxy, anthroxy, phenanthroxy or biphenoxy.

The term "arylalkyl" represents an aryl group attached to the adjacent atom by an alkyl, alkenyl or alkynyl. Examples include but are not limited to benzyl, benzhydryl, trityl, phenethyl, 3-phenylpropyl, 2-phenylpropyl, 4-phenylbutyl and naphthylmethyl.

The term "heteroaryl" represents a 3 to 11 membered optionally substituted saturated, unsaturated, partially saturated or aromatic cyclic moiety wherein said cyclic moiety is interrupted by at least one heteroatom selected from oxygen (O), sulfur (S) or nitrogen (N). Heteroaryls may be monocyclic or polycyclic rings. Heteroaryls may be 3 to 6 membered monocyclic ring or 5 to 6 membered monocyclic ring. Heteroaryls may be 7 to 12 membered bicyclic ring or 9 to 10 membered bicyclic ring. Examples of heteroaryls include but are not limited to azepinyl, aziridinyl, azetyl, azetidinyl, diazepinyl, dithiadiazinyl, dioxazepinyl, dioxolanyl, dithiazolyl, furanyl, isooxazolyl, isothiazolyl, imidazolyl, morpholinyl, morpholino, oxetanyl, oxadiazolyl, oxiranyl, oxazinyl oxazolyl, piperazinyl, piperonyl, pyrazinyl, pyridazinyl, pyrimidinyl, piperidyl, piperidino, pyridyl, pyranyl, pyrazolyl, pyrrolyl, pyrrolidinyl, phthalimidyl, thiatriazolyl, tetrazolyl, thiadiazolyl, triazolyl, thiazolyl, thienyl, tetrazinyl, thiadiazinyl, triazinyl, thiazinyl and thiopyranyl, furoisoxazolyl, imidazothiazolyl, thienoisothiazolyl, thienothiazolyl, imidazopyrazolyl, cyclopentapyrazolyl, pyrrolopyrrolyl, thienothienyl, thiadiazolopyrimidinyl, thiazolothiazinyl, thiazolopyrimidinyl, thiazolopyridinyl, oxazolopyrimidinyl, oxazolopyridyl, benzoxazolyl, benzisothiazolyl, benzothiazolyl, imidazopyrazinyl, purinyl, pyrazolopyrimidinyl, imidazopyridinyl, benzimidazolyl, indazolyl, benzoxathiolyl, benzodioxolyl, benzodithiolyl, indolizinyl, indolinyl, isoindolinyl, furopyrimidinyl, furopyridyl, benzofuranyl, isobenzofuranyl, thienopyrimidinyl, thienopyridyl, benzothienyl, cyclopentaoxazinyl, cyclopentafuranyl, benzoxazinyl, benzothiazinyl, quinazolinyl, naphthyridinyl, quinolinyl, isoquinolinyl, benzopyranyl, pyridopyridazinyl and pyridopyrimidinyl.

The term "alkenyl" refers to a straight or branched chain alkyl moiety having two or more carbon atoms (e.g., two to six carbon atoms, $C_{2-6}$ alkenyl) and having in addition one double bond, of either E or Z stereochemistry where applicable. Examples of alkenyl, groups include but are not limited to, allyl, vinyl, acetylenyl, ethylenyl, propenyl, isopropenyl, butenyl, isobutenyl, hexenyl, butadienyl, pentenyl, pentadienyl, hexenyl, hexadienyl, hexatrienyl, heptenyl, heptadienyl, heptatrienyl, octenyl, octadienyl, octatrienyl, octatetraenyl.

The term "cycloalkyl" refers to a saturated alicyclic moiety having three or more carbon atoms (e.g., from three to six carbon atoms) and which may be optionally benzofused at any available position. This term includes, for example, cyclopropyl, cyclobutyl, cyclopentyl, cyclohexyl, indanyl and tetrahydronaphthyl.

The term "heterocycloalkyl" refers to a saturated heterocyclic moiety having three or more carbon atoms (e.g., from three to six carbon atoms) and one or more heteroatom from the group N, O, S (or oxidised versions thereof) and which may be optionally benzofused at any available position. This term includes, for example, azetidinyl, pyrrolidinyl, tetrahydrofuranyl, piperidinyl, indolinyl and tetrahydroquinolinyl.

The term "cycloalkenyl" refers to an alicyclic moiety having three or more carbon atoms (e.g., from three to six carbon atoms) and having in addition one double bond. This term includes, for example, cyclopentenyl or cyclohexenyl.

The term "heterocycloalkenyl" refers to an alicyclic moiety having from three to six carbon atoms and one or more heteroatoms from the group N, O, S (or oxides thereof) and having in addition one double bond. This term includes, for example, dihydropyranyl.

The term "alkoxy" refers to straight-chain or branched alkyl groups having 1 to 10 carbon atoms as mentioned above, which are attached to the skeleton via an oxygen atom (—O—), for example C1-C10 alkoxy such as methyloxy, ethyloxy, propyloxy, 1-methylethyloxy, butyloxy, 1-methylpropyloxy, 2-methylpropyloxy, 1,1-dimethylethyloxy, isopropoxy, butoxy, isobutoxy, sec-butoxy, tert-butoxy, pentyloxy, isopentyloxy, neopentyloxy, tert-pentyloxy, hexyloxy, isohexyloxy, trifluoromethoxy and neohexyloxy.

The term "optionally substituted" means optionally substituted with one or more of the aforementioned groups (e.g., nitro, amino, CN, —C(O)O-alkyl, alkyl, aryl, heteroaryl, acyl, alkenyl, cycloalkyl, heterocycloalkyl, cycloalkenyl, heterocycloalkenyl, or halogen), at any available position or positions. Examples of optionally substitutions include, but is not limited, to, nitro, amino, CN, C(O)O—C1-6alkyl, halogen.

One aspect of the invention relates to a pharmaceutical composition comprising a compound as defined herein or a pharmaceutically acceptable salt or solvate thereof, and one or more than one pharmaceutically acceptable carriers. Many pharmaceutically acceptable carriers are known in the art. It will be understood by those in the art that a pharmaceutically acceptable carrier must be compatible with the other ingredients of the formulation and tolerated by a subject in need thereof.

In another embodiment, the pharmaceutical composition comprises at least one additional active ingredient including, but are not limited to, antioxidants, free radical scavenging agents, peptides, growth factors, antibiotics, bacteriostatic agents, immunosuppressives, anticoagulants, buffering agents, anti-inflammatory agents, anti-pyretics, time-release binders, anesthetics, steroids and corticosteroids, or other active ingredient commonly used for treating protozoan infection including pentavalent antimonials (SbV) such as sodium stibogluconate and meglumine antimoniate, amphotericin B (with or without liposomal formulations), miltefosine, pentamidine and paromomycin.

In an embodiment, the pharmaceutical compositions comprise a compound as defined herein or a pharmaceutically acceptable salt or solvate thereof, and a pharmaceutically acceptable carrier, optionally in association with at least one additional active agent.

In another aspect, the compounds and compositions comprise a compound selected from the group consisting of the compounds described herein, pharmaceutically acceptable salts, analogs, and mixtures thereof. Pharmaceutically acceptable salts of known in the art and it should be understood that pharmaceutically acceptable salts of the compounds described herein are encompassed by the present invention.

Compositions and formulations of the invention include those suitable for oral, rectal, nasal, topical (including transdermal, buccal and sublingual), vaginal, parental (including subcutaneous, intramuscular, intravenous and intradermal) and pulmonary administration.

Compositions of the present invention suitable for oral administration can be presented for example as discrete units such as capsules, cachets or tablets, each containing a predetermined amount of the active ingredient; or as an oil-in-water liquid emulsion, water-in-oil liquid emulsion or as a supplement within an aqueous solution.

The active ingredient can also be presented as bolus, electuary, or paste. Formulations suitable for topical administration in the mouth include lozenges comprising the active ingredient, pastilles comprising the active ingredient in gelatin and glycerin, or sucrose and acacia.

Therapeutic amounts can be empirically determined and will vary with the pathology being treated, body mass of the subject being treated, and the efficacy and toxicity of the agent. Similarly, suitable dosage formulations and methods of administering the agents can be readily determined by those of skill in the art. For example, a daily dosage can be divided into one, two or more doses in a suitable form to be administered at one, two or more times throughout a time period.

Another aspect of the invention relates to method of treatment or prevention of inhibiting a parasitic disease e.g. in mammals including humans, comprising the step of administering an effective amount of a compound as defined in claim 1, or a pharmaceutically acceptable salt or solvate thereof. In an embodiment, the method relates to the treatment or prevention of a parasitic disease caused by genus *Leishmania*, for example, infestation of parasites selected from the group consisting of *L. donovani, L. amazonensis, L. tarentolae, L. tropica, L. enriettii, L. mexicana*, and *L. major.*

The terms "treatment" or "treating" are intended to mean obtaining a desired pharmacologic and/or physiologic effect, such as an improvement in a disease condition in a subject or improvement of a symptom associated with a disease or a medical condition in a subject. The effect may be prophylactic in terms of completely or partially preventing a disease or symptom associated therewith and/or may be therapeutic in terms of a partial or complete cure for a disease and/or the pathophysiologic effect attributable to the disease. "Treatment" as used herein covers any treatment of a disease in a mammal and includes: (a) preventing a disease or condition (such as preventing cancer) from occurring in an individual who may be predisposed to the disease but has not yet been diagnosed as having it; (b) inhibiting the disease, (e.g., arresting its development); or (c) relieving the disease (e.g., reducing symptoms associated with the disease).

The term "biological activity" is intended to mean having therapeutic efficacy and/or the ability to treat protozoan disease in a subject. It also means the ability to kill promastigotes and/or amastigotes, the ability to increase ROS level in parasites, the ability to reduce mitochondrial membrane potential of parasites, and/or to trigger oxidative stress in parasites.

The term "administering" and "administration" is intended to mean a mode of delivery including, without limitation, oral, rectal, parenteral, subcutaneous, intravenous, intramuscular, intraperitoneal, intraarterial, transdermally or via a mucus membrane; the preferred one being orally. One skilled in the art recognizes that suitable forms of oral formulation include, but are not limited to, a tablet, a pill, a capsule, a lozenge, a powder, a sustained release tablet, a liquid, a liquid suspension, a gel, a syrup, a slurry, a suspension, and the like. For example, a daily dosage can be divided into one, two or more doses in a suitable form to be administered at one, two or more times throughout a time period.

The term "therapeutically effective" is intended to mean an amount of a compound sufficient to substantially improve a symptom associated with a disease or a medical condition or to improve, ameliorate or reduce the underlying disease or medical condition. A therapeutically effective amount of a compound may provide a treatment for a disease such that the onset of the disease is delayed, hindered, or prevented, or the disease symptoms are ameliorated, or the term of the disease is altered.

When the compounds of this invention are administered in combination with other agents, they may be administered prior, sequentially or concurrently to an individual. Alternatively, pharmaceutical compositions according to the present invention may be comprised of a combination of analogs of the present invention, as described herein, and another therapeutic or prophylactic agent known in the art.

It will be understood that a specific "effective amount" for any particular in vivo or in vitro application will depend upon a variety of factors including the activity of the specific compound employed, the age, body weight, general health, sex, and/or diet of the individual, time of administration, route of administration, rate of excretion, drug combination and the severity of the particular disease being treated. For example, the "effective amount" may be the amount of the compounds of the invention necessary to inhibit promastigotes and amastigotes.

Pharmaceutically acceptable acid addition salts may be prepared from inorganic and organic acids. Salts derived from inorganic acids include hydrochloric acid, hydrobromic acid, sulfuric acid, nitric acid, phosphoric acid, and the like. Salts derived from organic acids include citric acid, lactic acid, tartaric acid, fatty acids, and the like. Pharmaceutically acceptable salts are known in the art.

Salts may also be formed with bases. Such salts include salts derived from inorganic or organic bases, for example alkali metal salts such as magnesium or calcium salts, and organic amine salts such as morpholine, piperidine, dimethylamine or diethylamine salts.

As used herein, the term "pharmaceutically acceptable carrier" includes any and all solvents such as phosphate buffered saline, water, saline, dispersion media, coatings, antibacterial and antifungal agents, isotonic and absorption delaying agents and the like. The use of such media and agents for pharmaceutically active substances is well known in the art. Supplementary active ingredients can also be incorporated into the compositions. The pharmaceutical compositions of the invention can be formulated according to known methods for preparing pharmaceutically useful compositions. Formulations are described in a number of sources which are well known and readily available to those skilled in the art. For example, Remington's Pharmaceutical Science (Martin E W (1995) Easton Pa., Mack Publishing Company, 19th ed.) describes formulations which can be used in connection with the subject invention.

The compounds of the present invention can be prepared using techniques known in the art, which would be apparent to a person of ordinary skilled in the art in view of the exemplary synthesis processes described in the Examples, such as the synthesis process described in the preparation of 2-(4-(2-(2-(benzylamino)ethoxy)ethoxy)phenyl)-4H-chromen-4-one (FM04) and -(dibenzylamino)ethoxy)ethoxy)phenyl)-4H-chromen-4-one (FM19). As shown in Scheme 3 in the Example section, the reaction from compound 6 to compound 7 follows a well-established method of forming an ether by the Mitsunobu reaction readily known to a person of ordinary skilled in the art. It would be apparent to a person skilled in the art that replacing compound 6 with similar hydroxyamines will provide new compounds similar to compound 7 but having different linker. Conversion of compound 7 to FM20 involves a simple acid hydrolysis to remove the protecting group. The reaction of FM20 with benzyl bromide (as shown in Scheme 4) to give FM04 and FM19 is a straightforward reaction of an amine with an alkyl halide. By using different alkyl halides, compounds of general structure of the present invention can be readily obtained.

EXAMPLES

The following examples are provided solely in order to assist understanding and are non-limiting.
Experimental Procedures
  Cell Lines and Cell Culture.
  Promastigotes of visceral *L. donovani* Ld39 and LdHU3, and cutaneous *L. amazonensis* LV78, *L. braziliensis* UA847 and *L. major* FV1 were employed in the study. All strains were cultured in Schneider's *Drosophila* Medium (Invitrogen), pH 6.9 supplemented with 10% (v/v) heat inactivated fetal bovine serum (Hyclone) with 4 mM glutamine (Sigma) and 25 µg/mL gentamicin solution (Invitrogen) at 27° C. for 4 days. RAW264.7 cells were cultured in supplemented DMEM media with 10% heat inactivated FBS and 100 U/mL penicillin and 100 µg/mL of streptomycin. They were maintained at 37° C. in a humidified atmosphere with 5% $CO_2$. The cells were split constantly after a confluent monolayer has been formed. The cells were harvested by a cell scraper.
  In Vitro Anti-Promastigote Activity.
  Anti-promastigote activity was determined according to previous procedures (1) by Cell Titer 96® Aqueous Assay (Promega) that employed a tetrazolium compound. Promastigotes were seeded into 96-well flat bottom microtiter plate at $1\times10^5$ cells per well in a final volume of 100 µL medium and incubated with a series of concentrations of synthetic FM. Parasites were incubated at 27° C. for 72 hours. After 72 hours of incubation, 10 µL of MTS:PMS mixture [MTS: 2-(4,5-Dimethylthiazol-2-yl-)-5-[3-(carboxymethoxy)phenyl]-2-(4-sulfophenyl)-2H-tetrazolium); PMS: phenazine methosulfate both purchased from Sigma] was added into each well of microtiter plate. The plate was then incubated at 27° C. for 4 hours for color development. After 4 hours of incubation, the OD values were determined at 490 nm using automatic microtiter plate reader (Bio-Rad).

In Vitro Anti-Amastigote Activity.
  Mouse peritoneal elicited macrophages (PEM) were obtained as previously described (2). A round cover slip (12 mm in diameter) was placed into each well of 24-well culture plate. Mouse PEM were resuspended in supplemented DMEM media containing 10% heat inactivated FBS (v/v), 100 U/mL penicillin and 100 µg/mL streptomycin and seeded into each well at a cell density of $1\times10^5$ cells per 500 µL. Macrophages were allowed to attach overnight. Non-adherent cells were removed by gentle washing with un-supplemented DMEM media twice. Adherent macrophages were infected with late-log promastigotes at a parasite-to-macrophage ratio of 20:1 overnight at 37° C. with 5% $CO_2$. Non-internalized promastigotes were removed by washing twice with un-supplemented DMEM media. Infected macrophages were further incubated in 500 µL of supplemented DMEM media in the presence or absence of FM for 72 hours at 37° C. After incubation, cover slips were stained with Giemsa and the percentage of macrophages infected and number of amastigotes per 100 macrophages was enumerated.

Reactive Oxygen Species (ROS) Level Determination.
  50,000 RAW264.7 were seeded in each well of black 96-well plates overnight. Next day, RAW264.7 cells were pre-loaded with 10 µM dichlorofluorescein diacetate (DCFDA) (Abcam) for 1 hr at 37° C. with 5% $CO_2$. A control of non-DCFDA stained cells was also included. The DCFDA-contained supplemented DMEM media was removed. The cells were re-suspended with 10 µM or 30 µM of respective tested compounds and positive control, tert-butyl hydroperoxide. In *Leishmania*, $1\times10^7$ promastigotes were also pre-loaded with 10 µM DCFDA at 27° C. for 1 hr. After removing the DCFDA-contained media, the promastigotes were seeded into black 96-well plate and incubated with 30 µM of respective compounds or positive control. The ROS level was determined at different periods of time including 2, 4, 6, 8, 20, 46 and 72 hr using microplate reader (excitation: 485 nm and emission: 820 nm).

Mitochondrial Membrane Potential Measurement.
  $1\times10^7$ promastigotes were seeded into each well of 6-well plate. The promastigotes were incubated with different concentrations (0, 1.25, 2.5, 5 and 10 µM) of FM09 for 24 and 48 hr, respectively. After incubation, promastigotes were washed two times with 1×PBS and resuspended with 1000 µL of supplemented Schneider's Insect media containing 10 µg/mL of rhodamine 123 in an Eppendorf. The promastigotes were incubated with rhodamine 123 at room temperature for 40 min with shaking. After incubation, promastigotes were washed one time with cold 1×PBS and then re-suspended with 100 µL of 1×PBS. The fluorescent level of rhodamine 123 was measured with a microplate reader (excitation: 485 nm and emission: 520 nm).

Synthesis of Amine-Containing Flavonoid Monomers
  The detailed chemical synthesis of flavonoid monomer FM01 is described as shown in the scheme 1.

Scheme 1.

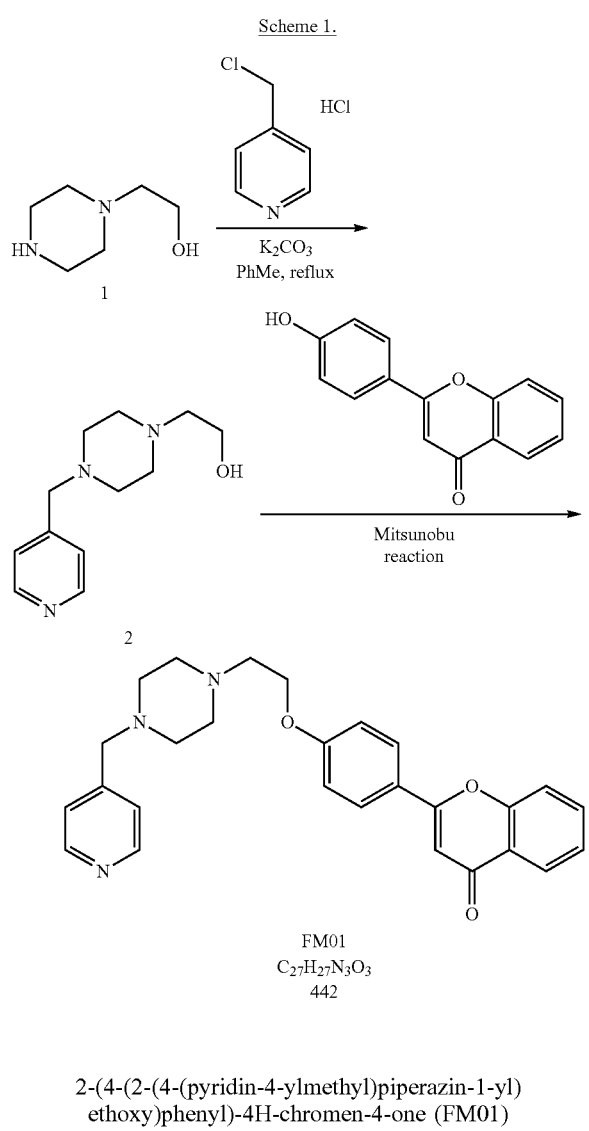

2-(4-(2-(4-(pyridin-4-ylmethyl)piperazin-1-yl)
ethoxy)phenyl)-4H-chromen-4-one (FM01)

To a well stirred mixture of hydroxylamine 1 (4.6 g, 35 mmol), 4-chloromethylpyridine hydrochloride (5.9 g, 36 mmol) and K$_2$CO$_3$ (10 g) in toluene (80 mL), the mixture was heated to reflux for 14 h. The reaction mixture was then filtered to remove excess K$_2$CO$_3$. The obtained filtrate was evaporated under reduced pressure to give oily crude mixture which was subjected vacuum distillation to furnish alcohol 2 (2.5 g) in 32% yield. $^1$H NMR (400 MHz, CHLOROFORM-d) δ 8.49 (d, J=5.87 Hz, 2H), 7.24 (d, J=5.38 Hz, 2H), 3.60 (t, J=5.62 Hz, 2H), 3.47 (s, 2H), 3.24 (br. s., 1H), 2.52 (t, J=5.38 Hz, 10H); $^{13}$C NMR (101 MHz, CHLOROFORM-d) δ 149.7, 147.6, 123.8, 61.6, 59.5, 57.9, 53.2, 52.9; Alcohol 2 was used for next step without further purification. To a well stirred mixture of alcohol 2 (0.45 g, 2.0 mmol), 4'-hydroxyflavone (0.49 g, 2.0 mmol) and PPh$_3$ (0.56 g, 2.1 mmol) in THF (20 mL), was added diisopropyl azodicarboxylate (DIAD) (0.43 g, 2.1 mmol) dropwise. The reaction mixture was further heated to reflux for 12 h. The reaction mixture was evaporated under reduced pressure to give brown oil which was subjected flash column chromatography on silica gel with gradient elution (20% acetone in DCM to 80% acetone to DCM) to furnish the desired product FM01 (0.32 g, 0.72 mmol) in 36% yield: $^1$H NMR (400 MHz, CHLOROFORM-d) δ 8.45 (d, J=5.38 Hz, 2H), 8.08-8.11 (m, 1H), 7.73 (d, J=8.80 Hz, 2H), 7.53-7.57 (m, 1H), 7.41 (d, J=8.31 Hz, 1H), 7.27 (t, J=7.34 Hz, 1H), 7.18 (d, J=5.38 Hz, 2H), 6.90 (d, J=8.80 Hz, 2H), 6.61 (s, 1H), 4.06 (t, J=5.62 Hz, 2H), 3.41 (s, 2H), 2.75 (t, J=5.62 Hz, 2H), 2.55 (br. s., 4H), 2.42 (br. s., 4H); $^{13}$C NMR (101 MHz, CHLOROFORM-d) δ 178.1, 163.2, 161.5, 156.0, 149.7, 147.5, 133.5, 127.9, 125.5, 125.0, 123.9, 123.8, 123.8, 117.9, 114.9, 106.0, 66.2, 61.6, 56.9, 53.5, 53.0; LRMS (ESI) m/z 442 (M$^+$+H, 100), 464 (M$^+$+Na, 10); HRMS (ESI) calcd for C$_{27}$H$_{28}$N$_3$O$_3$ (M$^+$+H) 442.2131, Found 442.2138.

The detailed chemical synthesis of flavonoid monomer FM02 is described as shown in the scheme 2.

Scheme 2.

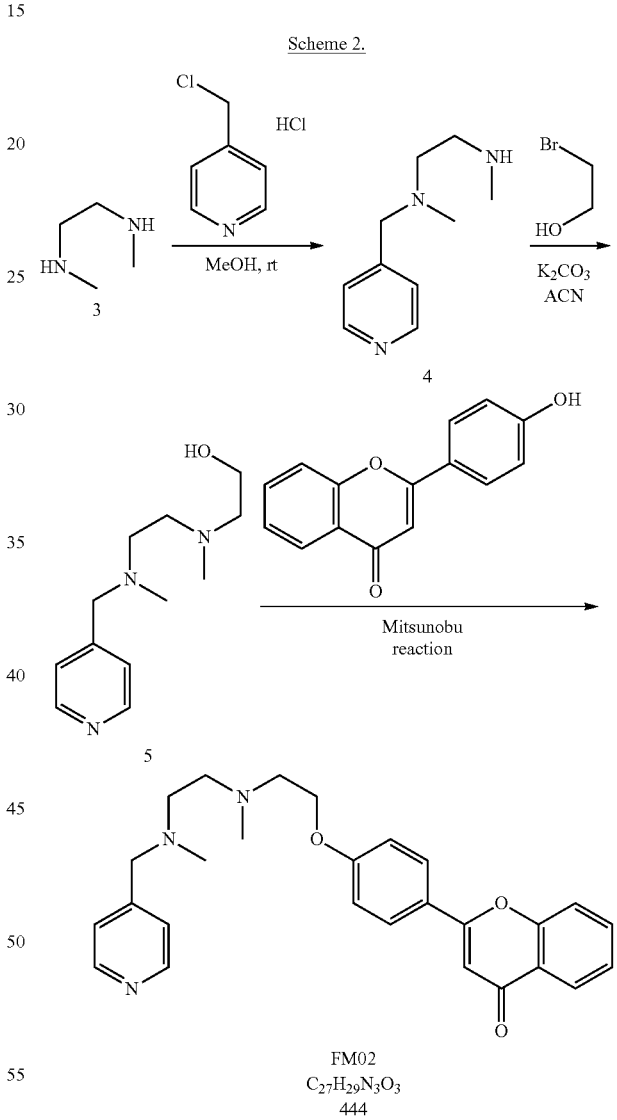

2-(4-(2-(methyl(2-(methyl(pyridin-4-ylmethyl)
amino)ethyl)amino)ethoxy) phenyl)-4H-chromen-4-
one (FM02)

To a well stirred mixture of diamine 3 (9.0 g, 102 mmol), 4-chloromethylpyridine hydrochloride (8.0 g, 49 mmol) and K$_2$CO$_3$ (7.0 g, 51 mmol) in MeOH (100 mL) at room temperature, was stirred for 16 h. After that, the mixture was poured into separating funnel containing 5% NaOH solution (200 mL) and extracted with DCM (50 mL×3). The combined organic layers were dried over MgSO₄, filtered and evaporated to crude brown oil which was subjected to flash column chromatography on silica gel with gradient elution (3% MeOH in DCM to 8% MeOH in DCM) to furnish diamine 4 (2.8 g) in 32% yield: $^1$H NMR (400 MHz, CHLOROFORM-d) δ 8.53 (d, J=5.87 Hz, 2H), 7.25 (d, J=5.87 Hz, 2H), 3.51 (s, 2H), 2.69 (t, J=5.87 Hz, 2H), 2.54 (t, J=6.11 Hz, 2H), 2.43 (s, 3H), 2.20 (s, 3H), 1.71 (br. s., 1H); $^{13}$C NMR (101 MHz, CHLOROFORM-d) δ 149.6, 148.3, 123.6, 61.5, 57.0, 49.3, 42.1, 36.4; To a well stirred mixture of diamine 4 (1.9 g, 11 mmol), 2-bromoethanol (1.4 g, 11 mmol) and K₂CO₃ (1.6 g, 12 mmol) in ACN (30 mL), was heated to reflux for 14 h. The mixture was filtered and evaporated under reduced pressure to give brown oil which was subjected flash column chromatography on silica gel with gradient elution (3% MeOH in DCM to 8% MeOH in DCM) to furnish alcohol 5 (1.5 g) in 63% yield: $^1$H NMR (400 MHz, CHLOROFORM-d) δ 8.52 (d, J=5.38 Hz, 2H), 7.17-7.34 (m, 2H), 3.87 (br. s., 1H), 3.57 (t, J=5.14 Hz, 2H), 3.50 (s, 2H), 2.45-2.61 (m, 6H), 2.27 (s, 3H), 2.19 (s, 3H); $^{13}$C NMR (101 MHz, CHLOROFORM-d) δ 149.8, 148.0, 123.9, 61.5, 59.1, 58.4, 55.6, 54.7, 42.8, 42.2; To a well stirred mixture of alcohol 5 (0.49 g, 2.2 mmol), 4'-hydroxyflavone (0.52 g, 2.2 mmol) and PPh₃ (0.60 g, 2.3 mmol) in THF (20 mL), was added DIAD (0.45 g, 2.2 mmol) dropwise. The reaction mixture was further heaed to reflux for 12 h. The reaction mixture was evaporated under reduced pressure to give brown oil which was subjected flash column chromatography on silica gel with gradient elution (20% acetone in DCM to 80% acetone to DCM) to furnish the desired product FM02 (0.27 g, 0.61 mmol) in 28% yield: $^1$H NMR (400 MHz, CHLOROFORM-d) δ 8.52 (d, J=5.38 Hz, 2H), 8.17-8.23 (m, 1H), 7.85 (d, J=9.29 Hz, 2H), 7.63-7.70 (m, 1H), 7.53 (d, J=8.80 Hz, 1H), 7.39 (t, J=7.58 Hz, 1H), 7.21-7.28 (m, 2H), 6.99 (d, J=8.80 Hz, 2H), 6.72 (s, 1H), 4.13 (t, J=5.62 Hz, 2H), 3.53 (s, 2H), 2.86 (t, J=5.87 Hz, 2H), 2.63-2.70 (m, 2H), 2.52-2.58 (m, 2H), 2.36 (s, 3H), 2.24 (s, 3H); $^{13}$C NMR (101 MHz, CHLOROFORM-d) δ 178.3, 163.3, 161.6, 156.2, 149.8, 148.4, 133.5, 128.0, 125.6, 125.0, 124.1, 123.9, 123.7, 123.7, 118.0, 115.0, 106.2, 66.5, 61.6, 56.5, 56.0, 55.4, 43.3, 42.8; LRMS (ESI) m/z 444 (M⁺+H, 100), 466 (M⁺+Na, 8); HRMS (ESI) calcd for C₂₇H₃₀N₃O₃ (M⁺+H) 444.2287, Found 444.2302.

The detailed chemical synthesis of flavonoid monomers FM03 and FM20 are described as shown in the scheme 3.

Scheme 3.

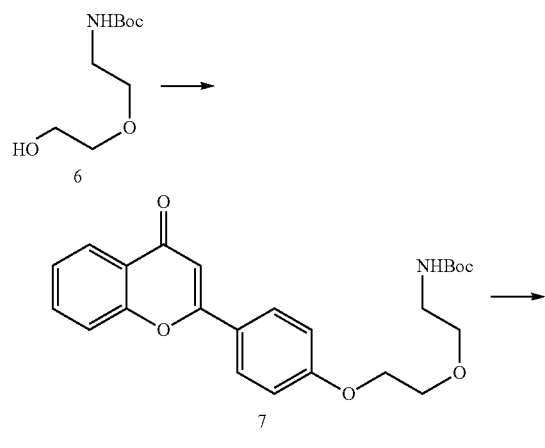

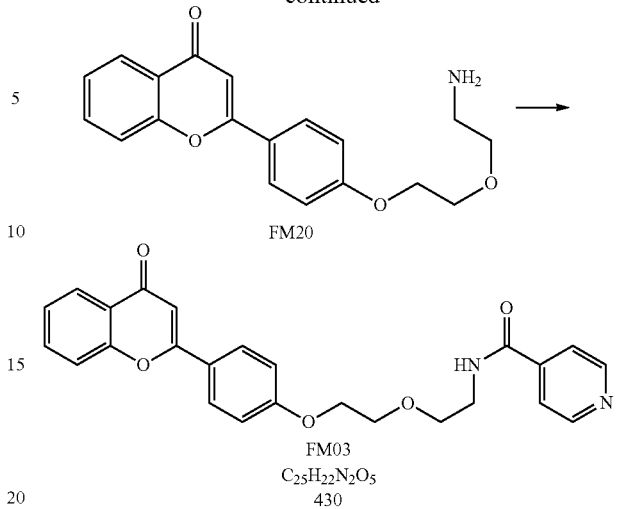

N-(2-(2-(4-(4-oxo-4H-chromen-2-yl)phenoxy) ethoxy)ethyl)isonicotinamide (FM03)

To a well stirred mixture of alcohol 6 (2.1 g, 10 mmol), 4'-hydroxyflavone (2.4 g, 10 mmol) and PPh₃ (3.0 g, 11 mmol) in THF (50 mL), was added DIAD (2.3 g, 11 mmol) dropwise. The reaction mixture was further heaed to reflux for 12 h. The reaction mixture was evaporated under reduced pressure to give brown oil which was subjected flash column chromatography on silica gel with gradient elution (20% EA in Hex to 70% EA in Hex) to furnish compound 7 (1.5 g) in 35% yield. To a well stirred compound 7 (1.0 g, mmol) in DCM (30 mL) at 0° C., was added excess trifluoroacetic acid (TFA) (5 mL). The mixture was stirred at room temperature for 3 h. After that, the mixture was poured into separating funnel containing water (100 mL), basified to pH10 with NaOH solution and extracted with DCM (30 mL×3). The combined organic layers were dried over MgSO₄, filtered and evaporated to FM20 (0.7 g) in 92% yield: $^1$H NMR (400 MHz, CHLOROFORM-d) δ 8.12 (dd, J=1.22, 8.07 Hz, 1H), 7.76 (d, J=9.29 Hz, 2H), 7.56-7.61 (m, 1H), 7.44 (d, J=8.31 Hz, 1H), 7.31 (t, J=7.34 Hz, 1H), 6.94 (d, J=8.80 Hz, 2H), 6.63 (s, 1H), 4.10-4.14 (m, 2H), 3.77-3.81 (m, 2H), 3.53 (t, J=5.14 Hz, 2H), 2.84 (t, J=5.14 Hz, 2H), 1.64 (s, 2H); $^{13}$C NMR (101 MHz, CHLOROFORM-d) δ 178.2, 163.2, 161.6, 156.0, 133.5, 127.9, 125.5, 125.0, 124.0, 123.8, 117.9, 115.0, 106.0, 73.6, 69.2, 67.6, 41.7; LRMS (ESI) m/z 326 (M⁺+H, 100); HRMS (ESI) calcd for C₁₉H₂₀NO₄ (M⁺+H) 326.1392, Found 326.1397. To well stirred solution of FM20 (0.30 g, 0.92 mmol) in pyridine (10 mL) at 00° C., was added isonicotinoyl chloride (0.20 g, 1.4 mmol) at once. The mixture was stirred further for 4 h. After that, the reaction mixture was washed with 1 M HCl solution and saturated NaHCO₃ solution. The organic layer was dried over MgSO₄, filtered and evaporated under reduced pressure to give pale brown oil which was subjected to flash column chromatography on silica gel with gradient elution (20% acetone in DCM to 70% acetone in DCM) to furnish the desired product FM03 (0.24 g, 0.56 mmol) in 60% yield: $^1$H NMR (400 MHz, CHLOROFORM-d) δ 8.72 (d, J=5.87 Hz, 2H), 8.24 (dd, J=0.98, 7.82 Hz, 1H), 7.89 (d, J=9.29 Hz, 2H), 7.67-7.75 (m, 1H), 7.54-7.65 (m, 3H), 7.44 (t, J=7.58 Hz, 1H), 7.03 (d, J=8.80 Hz, 2H), 6.70-6.85 (m, 2H), 4.20-4.30 (m, 2H), 3.88-3.99 (m, 2H), 3.69-3.83 (m, 4H); $^{13}$C NMR (101 MHz, CHLOROFORM-d) δ 178.3, 165.5, 163.2, 161.4, 156.2, 150.6, 141.5, 133.6, 128.1, 125.7, 125.2, 124.6, 124.0, 120.9, 118.0, 115.0, 106.4, 69.7, 69.4, 67.6, 39.8; LRMS (ESI) m/z 431 (M$^+$+H, 100), 453 (M$^+$+Na, 28); HRMS (ESI) calcd for $C_{25}H_{23}N_2O_5$ (M$^+$+H) 431.1607, Found 431.1623.

The detailed chemical synthesis of flavonoid monomers FM04 and FM19 are described as shown in the scheme 4.

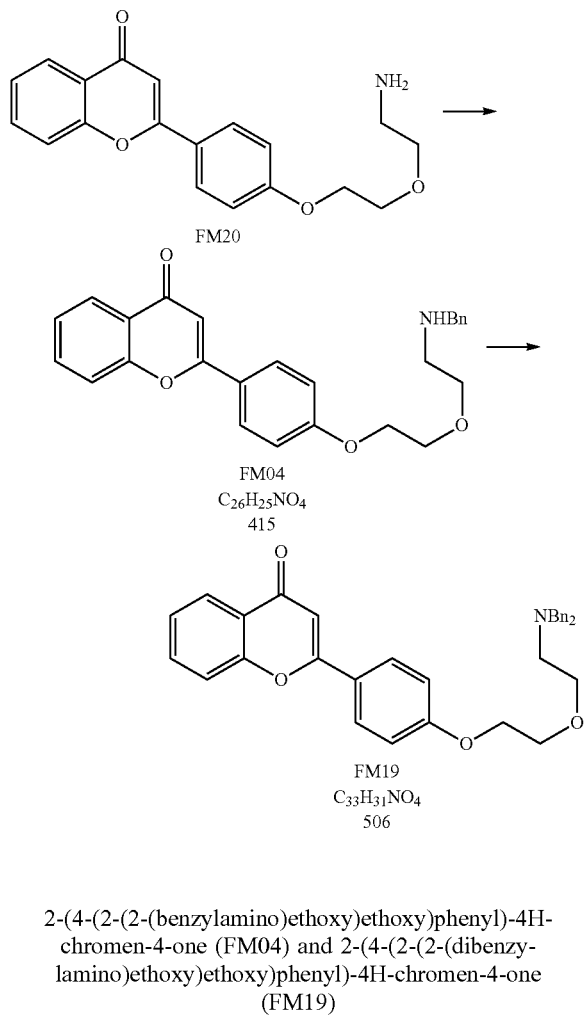

Scheme 4.

FM20

FM04
$C_{26}H_{25}NO_4$
415

FM19
$C_{33}H_{31}NO_4$
506

2-(4-(2-(2-(benzylamino)ethoxy)ethoxy)phenyl)-4H-chromen-4-one (FM04) and 2-(4-(2-(2-(dibenzylamino)ethoxy)ethoxy)phenyl)-4H-chromen-4-one (FM19)

To a well stirred mixture of FM20 (0.33 g, 1.0 mmol), benzyl bromide (0.25 g, 1.5 mmol) and $K_2CO_3$ (0.20 g, 1.4 mmol) in ACN (20 mL), was heated to reflux for 4 h. After that, the reaction mixture was filtered and the obtained filtrate was evaporated under reduced pressure to give pale brown oil which was subjected to flash chromatography on silica gel with gradient elution (10% acetone in DCM to 40% acetone in DCM) to furnish FM19 (0.24 g, 0.47 mmol) first in 47% yield and then FM04 (0.05 g, 0.12 mmol) in 12% yield. For FM19: $^1$H NMR (400 MHz, CHLOROFORM-d) δ 8.26 (d, J=6.85 Hz, 1H), 7.88 (d, J=8.80 Hz, 2H), 7.68-7.73 (m, 1H), 7.57 (d, J=8.31 Hz, 1H), 7.23-7.45 (m, 11H), 7.03 (d, J=8.80 Hz, 2H), 6.77 (s, 1H), 4.16-4.21 (m, 2H), 3.76-3.84 (m, 2H), 3.66-3.72 (m, 6H), 2.76 (t, J=6.11 Hz, 2H); $^{13}$C NMR (101 MHz, CHLOROFORM-d) δ 178.4, 163.4, 161.7, 156.2, 139.8, 133.6, 128.8, 128.2, 128.0, 126.9, 125.7, 125.1, 124.0, 118.0, 115.1, 106.2, 90.6, 70.4, 69.2, 67.7, 59.0, 52.8; LRMS (ESI) m/z 506 (M$^+$+H, 100); HRMS (ESI) calcd for $C_{33}H_{32}NO_4$ (M$^+$+H) 506.2331, Found 506.2332. For FM04: $^1$H NMR (400 MHz, CHLOROFORM-d) δ 8.25 (d, J=8.31 Hz, 1H), 7.89 (d, J=8.80 Hz, 2H), 7.65-7.79 (m, 1H), 7.57 (d, J=8.31 Hz, 1H), 7.43 (t, J=7.58 Hz, 1H), 7.23-7.38 (m, 5H), 7.05 (d, J=8.80 Hz, 2H), 6.77 (s, 1H), 4.06-4.26 (m, 2H), 3.80-3.90 (m, 4H), 3.73 (t, J=5.14 Hz, 2H), 2.88 (t, J=5.14 Hz, 2H); $^{13}$C NMR (101 MHz, CHLOROFORM-d) δ 178.4, 163.4, 161.7, 156.2, 140.1, 133.6, 128.4, 128.2, 128.0, 127.0, 125.7, 125.1, 124.3, 124.0, 118.0, 115.1, 106.3, 70.9, 69.4, 67.6, 53.9, 48.7; LRMS (ESI) m/z 416 (M$^+$+H, 100); HRMS (ESI) calcd for $C_{26}H_{26}NO_4$ (M$^+$+H) 416.1862, Found 416.1871.

The detailed chemical synthesis of flavonoid monomer FM05 is described as shown in the scheme 5.

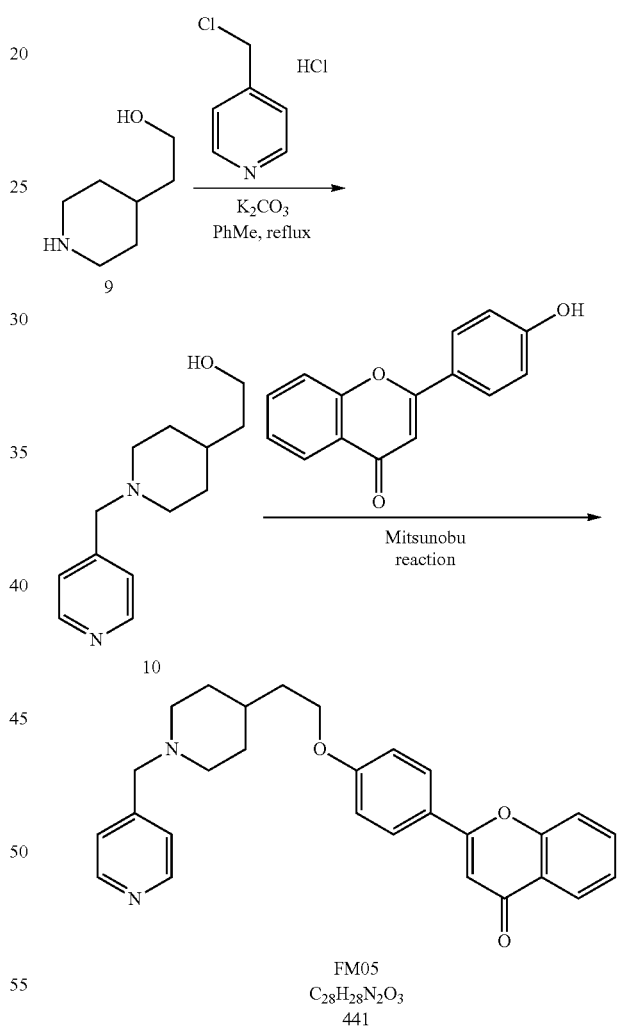

FM05
$C_{28}H_{28}N_2O_3$
441

2-(4-(2-(1-(pyridin-4-ylmethyl)piperidin-4-yl)ethoxy)phenyl)-4H-chromen-4-one (FM05)

To a well stirred mixture of hydroxylamine 9 (2.6 g, 20 mmol), 4-chloromethylpyridine hydrochloride (3.6 g, 22 mmol) and $K_2CO_3$ (3.2 g) in toluene (60 mL), the mixture was heated to reflux for 14 h. The reaction mixture was then filtered to remove excess $K_2CO_3$. The obtained filtrate was evaporated under reduced pressure to give oily crude mixture which was subjected vacuum distillation to furnish alcohol 10 (1.8 g) in 41% yield: $^1$H NMR (400 MHz, CHLOROFORM-d) δ 8.42-8.62 (m, 2H), 7.19-7.36 (m, 2H), 3.70 (dt, J=2.20, 6.48 Hz, 2H), 3.48 (s, 2H), 2.82 (s, 2H), 1.99 (t, J=11.49 Hz, 2H), 1.67 (s, 2H), 1.41-1.60 (m, 3H), 1.19-1.38 (m, 2H); $^{13}$C NMR (101 MHz, CHLOROFORM-d) δ 149.6, 148.2, 123.9, 62.2, 60.3, 54.0, 39.4, 32.3, 32.2; Alcohol 10 was used for next step without further purification. To a well stirred mixture of alcohol 10 (0.54 g, 2.5 mmol), 4'-hydroxyflavone (0.60 g, 2.5 mmol) and PPh$_3$ (0.71 g, 2.7 mmol) in THF (20 mL), was added DIAD (0.55 g, 2.7 mmol) dropwise. The reaction mixture was further headed to reflux for 12 h. The reaction mixture was evaporated under reduced pressure to give brown oil which was subjected flash column chromatography on silica gel with gradient elution (20% acetone in DCM to 80% acetone in DCM) to furnish the desired product FM05 (0.39 g) in 36% yield: $^1$H NMR (400 MHz, CHLOROFORM-d) δ 8.49 (d, J=5.87 Hz, 2H), 8.15-8.18 (m, 1H), 7.80 (d, J=8.80 Hz, 2H), 7.59-7.64 (m, 1H), 7.48 (d, J=8.31 Hz, 1H), 7.34 (t, J=7.58 Hz, 1H), 7.23 (d, J=5.87 Hz, 2H), 6.94 (d, J=8.80 Hz, 2H), 6.68 (s, 1H), 4.02 (t, J=6.60 Hz, 2H), 3.44 (s, 2H), 2.81 (d, J=11.25 Hz, 2H), 1.94-2.01 (m, 2H), 1.66-1.76 (m, 4H), 1.51 (dd, J=3.91, 7.34 Hz, 1H), 1.27-1.37 (m, 2H); $^{13}$C NMR (101 MHz, CHLOROFORM-d) δ 178.2, 163.3, 161.8, 156.1, 149.7, 149.6, 148.1, 133.5, 127.9, 125.6, 125.0, 123.9, 123.8, 123.7, 117.9, 114.9, 106.0, 65.9, 62.1, 53.9, 35.6, 32.5, 32.3; LRMS (ESI) m/z 441 (M$^+$+H, 100), 463 (M$^+$+Na, 15); HRMS (ESI) calcd for C$_{28}$H$_{29}$N$_2$O$_3$ (M$^+$+H) 441.2178, Found 441.2176.

The detailed chemical synthesis of flavonoid monomer FM06 is described as shown in the scheme 6.

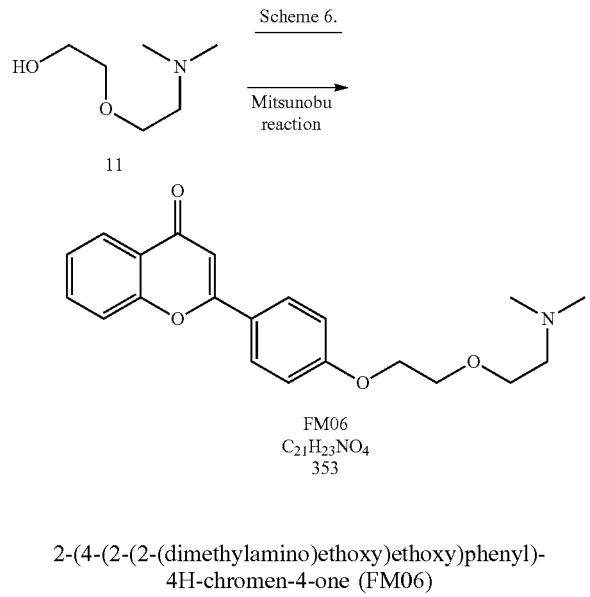

2-(4-(2-(2-(dimethylamino)ethoxy)ethoxy)phenyl)-4H-chromen-4-one (FM06)

To a well stirred solution of alcohol 11 (0.32 g, 2.4 mmol), 4'-hydroxyflavone (0.60 g, 2.5 mmol) and PPh$_3$ (0.71 g, 2.7 mmol) in THF (20 mL), was added DIAD (0.55 g, 2.7 mmol) dropwise. The reaction mixture was further headed to reflux for 12 h. The reaction mixture was evaporated under reduced pressure to give brown oil which was subjected flash column chromatography on silica gel with gradient elution (20% acetone in DCM to 80% acetone to DCM) to furnish the desired product FM06 (0.08 g, 0.2 mmol) in 9% yield: $^1$H NMR (400 MHz, CHLOROFORM-d) δ 8.24 (d, J=7.34 Hz, 1H), 7.90 (d, J=8.80 Hz, 2H), 7.66-7.76 (m, 1H), 7.57 (d, J=8.31 Hz, 1H), 7.43 (t, J=7.58 Hz, 1H), 7.06 (d, J=8.80 Hz, 2H), 6.76 (s, 1H), 4.18-4.33 (m, 2H), 3.84-3.92 (m, 2H), 3.70 (t, J=5.87 Hz, 2H), 2.59 (t, J=5.62 Hz, 2H), 2.32 (s, 6H); $^{13}$C NMR (101 MHz, CHLOROFORM-d) δ 178.4, 163.4, 161.7, 156.2, 133.6, 128.0, 125.7, 125.1, 124.2, 124.0, 118.0, 115.1, 106.2, 69.6, 69.4, 67.7, 58.8, 45.8; LRMS (ESI) m/z 354 (M$^+$+H, 100); HRMS (ESI) calcd for C$_{21}$H$_{24}$NO$_4$ (M$^+$+H) 354.1705, Found 354.1714.

The detailed chemical synthesis of flavonoid monomer FM07 is described as shown in the scheme 7.

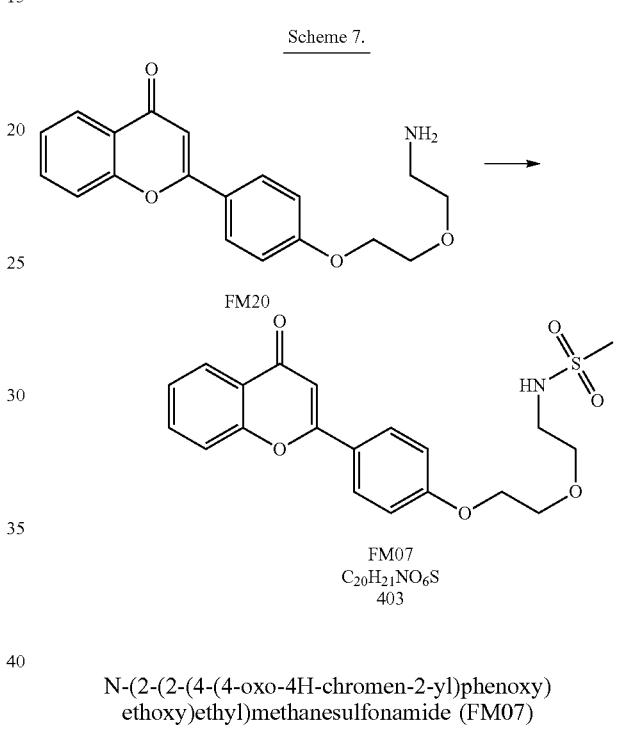

N-(2-(2-(4-(4-oxo-4H-chromen-2-yl)phenoxy)ethoxy)ethyl)methanesulfonamide (FM07)

To a well stirred solution of FM20 (0.13 g, 0.40 mmol) and excess NEt$_3$ (5 mL) in DCM (5 mL) at 0° C., was added methanesulfonyl chloride (MsCl) (0.10 g, 0.87 mmol) dropwise. The reaction mixture was stirred further for 4 h. After that, the reaction mixture was washed with 1 M HCl solution and saturated NaHCO$_3$ solution. The organic layer was dried over MgSO$_4$, filtered and evaporated under reduced pressure to give pale brown oil which was subjected to flash column chromatography on silica gel with gradient elution (20% acetone in DCM to 70% acetone in DCM) to furnish the desired product FM07 (0.09 g, 0.22 mmol) in 56% yield: $^1$H NMR (400 MHz, CHLOROFORM-d) δ 8.21 (dd, J=1.22, 8.07 Hz, 1H), 7.86 (d, J=8.80 Hz, 2H), 7.65-7.71 (m, 1H), 7.54 (d, J=8.31 Hz, 1H), 7.41 (t, J=7.34 Hz, 1H), 7.02 (d, J=8.80 Hz, 2H), 6.74 (s, 1H), 5.13 (t, J=5.62 Hz, 1H), 4.16-4.22 (m, 2H), 3.83-3.92 (m, 2H), 3.73 (t, J=5.14 Hz, 2H), 3.38 (q, J=5.38 Hz, 2H), 3.00 (s, 3H); $^{13}$C NMR (101 MHz, CHLOROFORM-d) δ 178.4, 163.3, 161.4, 156.2, 133.6, 128.0, 125.6, 125.1, 124.4, 123.9, 118.0, 115.0, 106.2, 70.3, 69.5, 67.5, 43.1, 40.5; LRMS (ESI) m/z 404 (M$^+$+H, 100), 426 (M$^+$+Na, 53); HRMS (ESI) calcd for C$_{20}$H$_{22}$NO$_6$S (M++H) 404.1168, Found 404.1181.

The detailed chemical synthesis of flavonoid monomer FM08 is described as shown in the scheme 8.

Scheme 8.

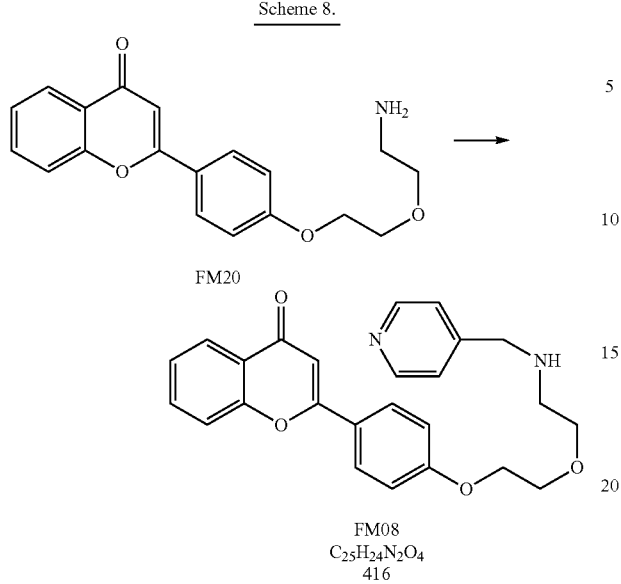

2-(4-(2-(2-((pyridin-4-ylmethyl)amino)ethoxy)ethoxy)phenyl)-4H-chromen-4-one (FM08)

To a well stirred mixture of FM20 (0.16 g, 0.49 mmol), 4-chloromethylpyridine hydrochloride (0.19 g, 1.2 mmol) and $K_2CO_3$ (0.20 g, 1.4 mmol) in MeOH (10 mL), was stirred at room temperature for 14 h. After that, the reaction mixture was filtered and the obtained filtrate was evaporated under reduced pressure to give pale brown oil which was subjected to flash chromatography on silica gel with gradient elution (20% acetone in DCM to 70% acetone in DCM) to furnish FM08 (0.04 g, 0.10 mmol) in 20% yield: $^1$H NMR (400 MHz, CHLOROFORM-d) δ 8.51 (d, J=5.87 Hz, 2H), 8.19 (d, J=7.82 Hz, 1H), 7.83 (d, J=8.80 Hz, 2H), 7.63-7.68 (m, 1H), 7.52 (d, J=8.31 Hz, 1H), 7.37 (t, J=7.58 Hz, 1H), 7.24 (d, J=5.38 Hz, 2H), 7.00 (d, J=8.80 Hz, 2H), 6.70 (s, 1H), 4.16-4.20 (m, 2H), 3.80-3.87 (m, 4H), 3.68 (t, J=4.89 Hz, 2H), 2.82 (t, J=5.14 Hz, 2H), 2.08 (br. s., 1H); $^{13}$C NMR (101 MHz, CHLOROFORM-d) δ 178.3, 163.3, 161.6, 156.1, 149.8, 149.3, 133.6, 128.0, 125.6, 125.1, 124.2, 123.9, 122.9, 118.0, 115.0, 106.2, 70.8, 69.4, 67.6, 52.5, 48.7; LRMS (ESI) m/z 417 (M++H, 100); HRMS (ESI) calcd for $C_{25}H_{25}N_2O_4$ (M$^+$+H) 417.1814, Found 417.1812.

The detailed chemical synthesis of flavonoid monomer FM09 is described as shown in the scheme 9.

Scheme 9.

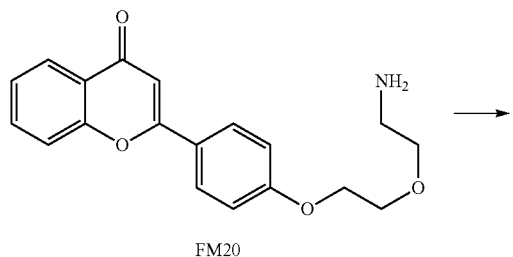

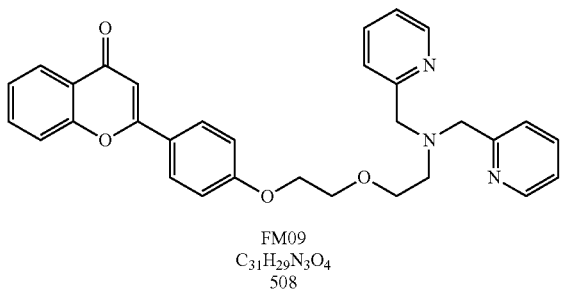

2-(4-(2-(2-(bis(pyridin-2-ylmethyl)amino)ethoxy)ethoxy)phenyl)-4H-chromen-4-one (FM09)

To a well stirred mixture of FM20 (0.15 g, 0.46 mmol), 2-chloromethylpyridine hydrochloride (0.21 g, 1.3 mmol) and $K_2CO_3$ (0.20 g, 1.4 mmol) in ACN (20 mL), was heated to reflux for 4 h. After that, the reaction mixture was filtered and the obtained filtrate was evaporated under reduced pressure to give pale brown oil which was subjected to flash chromatography on silica gel with gradient elution (20% acetone in DCM to 70% acetone in DCM) to furnish FM09 (0.12 g, 0.24 mmol) in 51% yield: $^1$H NMR (400 MHz, CHLOROFORM-d) δ 8.50 (d, J=4.40 Hz, 2H), 8.20 (d, J=7.82 Hz, 2H), 7.83 (d, J=8.80 Hz, 2H), 7.51-7.68 (m, 6H), 7.38 (t, J=7.34 Hz, 1H), 7.09-7.13 (m, 2H), 6.99 (d, J=8.80 Hz, 2H), 6.71 (s, 1H), 4.13-4.17 (m, 2H), 3.91 (s, 4H), 3.76-3.80 (m, 2H), 3.70 (t, J=5.87 Hz, 2H), 2.86 (t, J=5.87 Hz, 2H); $^{13}$C NMR (101 MHz, CHLOROFORM-d) δ 178.3, 163.3, 161.7, 159.8, 156.2, 149.0, 136.4, 133.6, 127.9, 125.6, 125.1, 124.1, 123.9, 123.0, 121.9, 118.0, 115.1, 106.2, 69.9, 69.2, 67.7, 60.9, 53.6; LRMS (ESI) m/z 508 (M++H, 100), 530 (M++Na, 19); HRMS (ESI) calcd for $C_{31}H_{30}N_3O_4$ (M$^+$+H) 508.2236, Found 508.2239.

The detailed chemical synthesis of flavonoid monomer FM10 is described as shown in the scheme 10.

Scheme 10.

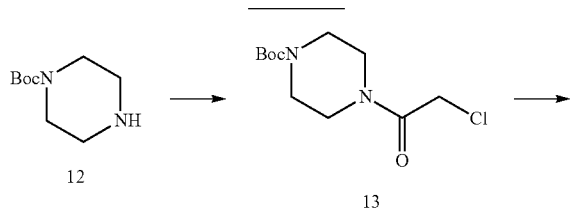

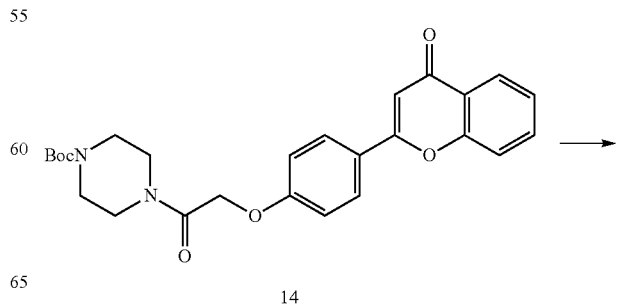

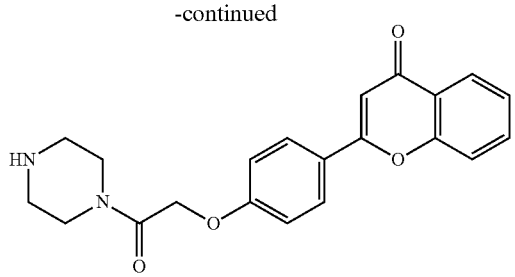

FM10
C₂₁H₂₀N₂O₄
364

2-(4-(2-oxo-2-(piperazin-1-yl)ethoxy)phenyl)-4H-chromen-4-one (FM10)

To well stirred solution of amine 12 (4.0 g, 22 mmol) in pyridine (3 mL) and DCM (50 mL) at 0° C., was added chloroacetyl chloride (3.0 g, 26 mmol) dropwise. The mixture was stirred further for 4 h. After that, the reaction mixture was washed with 1 M HCl solution and saturated NaHCO₃ solution. The organic layer was dried over MgSO₄, filtered and evaporated under reduced pressure to give chloride 13 (5.0 g, 88%) which was proceeded to next step without further purification. To a well stirred mixture of chloride 13 (5.0 g, 19 mmol), 4-hydroxyflavone (5.0 g, 21 mmol) and K₂CO₃ (3.5 g, 25 mmol) in DMF (50 mL), was heated to reflux for 4 h. The reaction mixture was then poured into a separating funnel containing water (200 mL) and extracted with DCM (40 mL×3). The combined organic layers were dried over MgSO₄, filtered and evaporated to give a pale brown oil which was subjected to flash column chromatography on silica gel with gradient elution (30% EA in Hex to 80% EA in Hex) to afford compound 14 (6.1 g, 13 mmol) in 69% yield: ¹H NMR (400 MHz, CHLOROFORM-d) δ 8.24 (dd, J=1.22, 8.07 Hz, 1H), 7.91 (d, J=9.29 Hz, 2H), 7.66-7.74 (m, 1H), 7.57 (d, J=8.31 Hz, 1H), 7.43 (t, J=7.34 Hz, 1H), 7.10 (d, J=8.80 Hz, 2H), 6.76 (s, 1H), 4.82 (s, 2H), 3.54-3.67 (m, 4H), 3.38-3.53 (m, 4H), 1.48 (s, 9H); ¹³C NMR (101 MHz, CHLOROFORM-d) δ 178.4, 166.0, 163.1, 160.4, 156.2, 133.7, 128.2, 125.7, 125.3, 125.2, 123.9, 118.0, 115.1, 106.6, 80.5, 67.7, 45.3, 28.4; To a well stirred solution of compound 14 (5.0 g, 11 mmol) in chloroform (20 mL) at 0° C., was added excess TFA (10 mL). The mixture was stirred at room temperature for 3 h. After that, the mixture was poured into separating funnel containing water (200 mL), basified to pH10 with NaOH solution and extracted with DCM (40 mL×3). The combined organic layers were dried over MgSO₄, filtered and evaporated to the desired product FM10 (3.2 g, 8.8 mmol) in 82% yield: ¹H NMR (400 MHz, CHLOROFORM-d) δ 8.08-8.17 (m, 1H), 7.78 (d, J=8.80 Hz, 2H), 7.53-7.67 (m, 1H), 7.45 (d, J=8.31 Hz, 1H), 7.32 (t, J=7.34 Hz, 1H), 7.00 (d, J=8.80 Hz, 2H), 6.63 (s, 1H), 4.73 (s, 2H), 3.44-3.68 (m, 4H), 2.73-2.94 (m, 4H), 1.96 (br. s., 1H); ¹³C NMR (101 MHz, CHLOROFORM-d) δ 178.2, 165.7, 163.1, 160.7, 156.1, 133.6, 128.0, 125.5, 125.1, 124.8, 123.8, 118.0, 115.1, 106.2, 67.2, 46.5, 46.3, 45.8, 43.2; LRMS (ESI) m/z 365 (M⁺+H, 100); HRMS (ESI) calcd for C₂₁H₂₁N₂O₄ (M⁺+H) 365.1501, Found 365.1509.

The detailed chemical synthesis of flavonoid monomer FM11 is described as shown in the scheme 11.

Scheme 11.

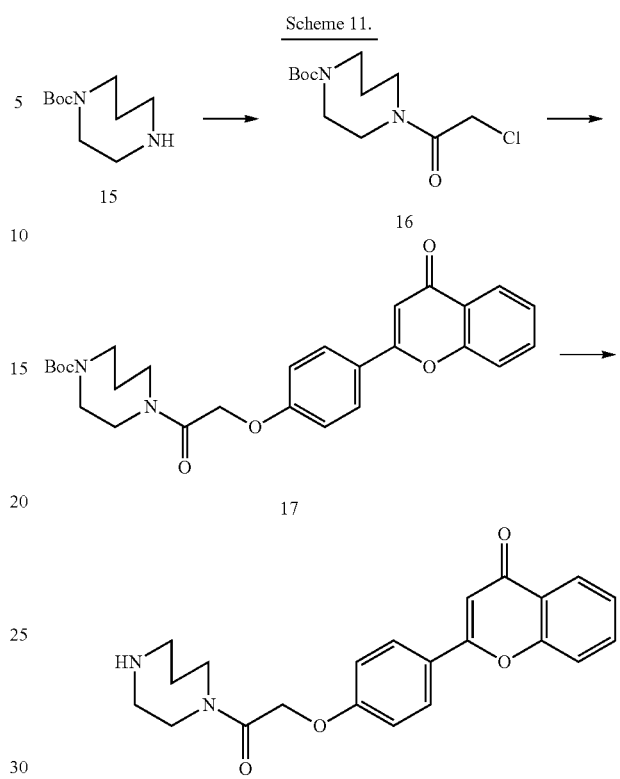

FM11
C₂₂H₂₂N₂O₄
378

2-(4-(2-(1,4-diazepan-1-yl)-2-oxoethoxy)phenyl)-4H-chromen-4-one (FM11)

To well stirred solution of amine 15 (4.0 g, 20 mmol) in pyridine (3 mL) and DCM (50 mL) at 0° C., was added chloroacetyl chloride (3.0 g, 26 mmol) dropwise. The mixture was stirred further for 4 h. After that, the reaction mixture was washed with 1 M HCl solution and saturated NaHCO₃ solution. The organic layer was dried over MgSO₄, filtered and evaporated under reduced pressure to give chloride 16 (4.1 g, 74%) which was proceeded to next step without further purification. To a well stirred mixture of chloride 16 (4.1 g, 15 mmol), 4-hydroxyflavone (3.7 g, 15 mmol) and K₂CO₃ (3.0 g, 22 mmol) in DMF (40 mL), was heated to reflux for 4 h. The reaction mixture was then poured into a separating funnel containing water (200 mL) and extracted with DCM (40 mL×3). The combined organic layers were dried over MgSO₄, filtered and evaporated to give a pale brown oil which was subjected to flash column chromatography on silica gel with gradient elution (30% EA in Hex to 80% EA in Hex) to afford compound 17 (5.0 g, 10 mmol) in 71% yield. To a well stirred solution of compound 17 (5.0 g, 10 mmol) in chloroform (20 mL) at 00° C., was added excess TFA (10 mL). The mixture was stirred at room temperature for 3 h. After that, the mixture was poured into separating funnel containing water (200 mL), basified to pH10 with NaOH solution and extracted with DCM (40 mL×3). The combined organic layers were dried over MgSO₄, filtered and evaporated to the desired product FM11 (3.1 g, 8.5 mmol) in 79% yield: ¹H NMR (400 MHz, CHLOROFORM-d) δ 8.18 (d, J=7.83 Hz, 1H), 7.85 (d, J=8.80 Hz, 2H), 7.66 (t, J=7.83 Hz, 1H), 7.51 (d, J=8.31 Hz, 1H), 7.38 (t, J=7.58 Hz, 1H), 7.06 (d, J=8.80 Hz, 2H), 6.71 (s, 1H), 4.79 (d, J=7.34 Hz, 2H), 3.55-3.68 (m, 4H), 2.83-3.03 (m, 4H), 2.14 (br. s., 1H), 1.77-1.91 (m, 2H); $^{13}$C NMR (101 MHz, CHLOROFORM-d) δ 178.3, 167.0, 166.9, 163.2, 160.8, 160.8, 156.1, 133.6, 128.1, 125.6, 125.1, 124.8, 123.9, 118.0, 115.2, 106.3, 67.4, 67.2, 50.2, 50.2, 49.2, 48.9, 48.4, 47.6, 46.5, 45.2, 31.1, 29.1; LRMS (ESI) m/z 379 (M$^+$+H, 100); HRMS (ESI) calcd for $C_{22}H_{23}N_2O_4$ (M$^+$+H) 379.1658, Found 379.1672.

The detailed chemical synthesis of flavonoid monomer FM12 is described as shown in the scheme 12.

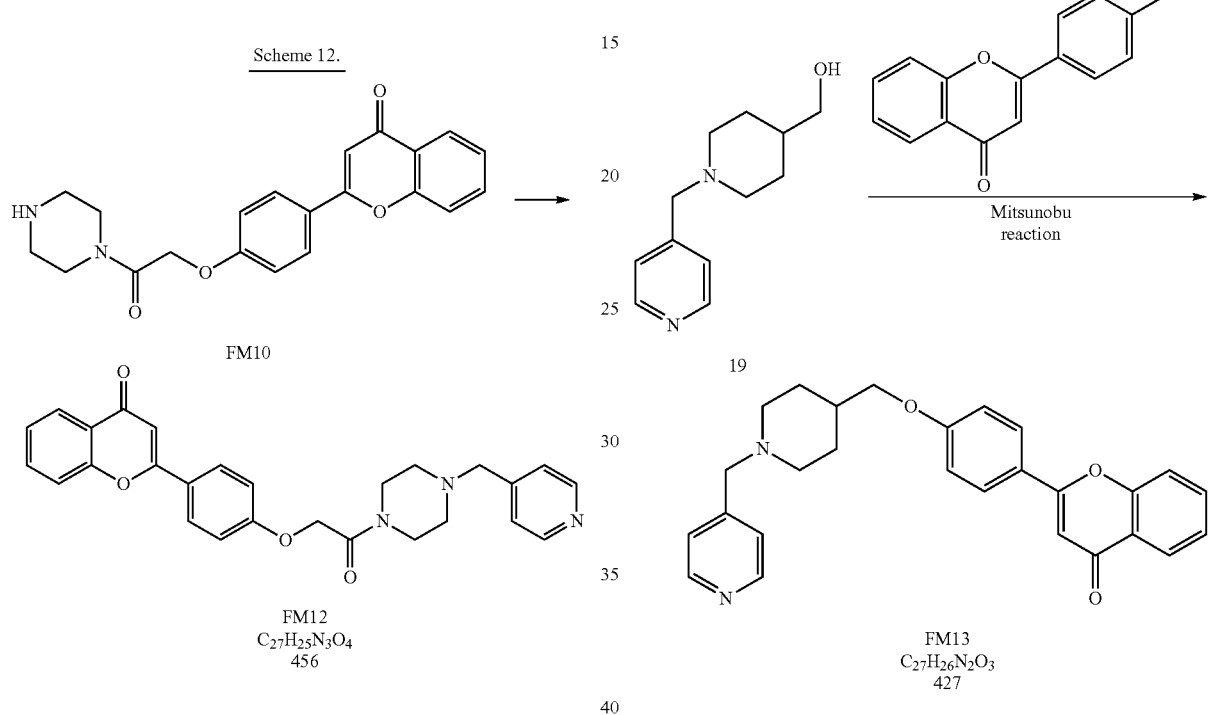

2-(4-(2-oxo-2-(4-(pyridin-4-ylmethyl)piperazin-1-yl) ethoxy)phenyl)-4H-chromen-4-one (FM12)

To a well stirred mixture of FM10 (0.59 g, 1.6 mmol), 4-chloromethylpyridine hydrochloride (0.30 g, 1.8 mmol) and $K_2CO_3$ (0.60 g) in toluene (30 mL), the mixture was heated to reflux for 4 h. The reaction mixture was then filtered to remove excess $K_2CO_3$. The obtained filtrate was evaporated under reduced pressure to give oily crude mixture which was subjected to flash column chromatography on silica gel with gradient elution (20% acetone in DCM to 80% acetone to DCM) to furnish the desired product FM12 (0.30 g, 0.66 mmol) in 36% yield: $^1$H NMR (400 MHz, CHLOROFORM-d) δ 8.55 (d, J=5.38 Hz, 2H), 8.20-8.23 (m, 1H), 7.88 (d, J=8.80 Hz, 2H), 7.66-7.71 (m, 1H), 7.54 (d, J=8.80 Hz, 1H), 7.41 (t, J=7.58 Hz, 1H), 7.27 (d, J=5.38 Hz, 2H), 7.08 (d, J=8.80 Hz, 2H), 6.74 (s, 1H), 4.79 (s, 2H), 3.59-3.70 (m, 4H), 3.52 (s, 2H), 2.43-2.49 (m, 4H); $^{13}$C NMR (101 MHz, CHLOROFORM-d) δ 178.3, 165.7, 163.1, 160.6, 156.2, 149.9, 146.9, 133.7, 128.1, 125.7, 125.1, 125.1, 123.9, 123.7, 118.0, 115.2, 106.5, 77.3, 67.5, 61.5, 53.2, 52.8, 45.3, 42.1; LRMS (ESI) m/z 456 (M$^+$+H, 100); HRMS (ESI) calcd for $C_{27}H_{26}N_3O_4$ (M$^+$+H) 456.1923, Found 456.1926.

The detailed chemical synthesis of flavonoid monomer FM13 is described as shown in the scheme 13.

2-(4-((1-(pyridin-4-ylmethyl)piperidin-4-yl) methoxy)phenyl)-4H-chromen-4-one (FM13)

To a well stirred mixture of hydroxylamine 18 (4.6 g, 40 mmol), 4-chloromethylpyridine hydrochloride (6.6 g, 40 mmol) and $K_2CO_3$ (12 g, 87 mmol) in MeOH (60 mL), the mixture was heated to reflux for 14 h. The reaction mixture was then filtered to remove excess $K_2CO_3$. The obtained filtrate was evaporated under reduced pressure to give oily crude mixture which was subjected vacuum distillation to furnish alcohol 19 (3.6 g, 17 mmol) in 44% yield: $^1$H NMR (400 MHz, CHLOROFORM-d) δ 8.48 (br. s., 2H), 7.19-7.31 (m, 2H), 3.36-3.58 (m, 4H), 2.84 (br. s., 2H), 1.91-2.06 (m, 2H), 1.70 (s, 2H), 1.41-1.58 (m, 1H), 1.26-1.28 (m, 2H); $^{13}$C NMR (101 MHz, CHLOROFORM-d) δ 149.4, 148.3, 123.9, 67.4, 62.1, 53.7, 38.5, 28.9; Alcohol 19 was used for next step without further purification. To a well stirred mixture of alcohol 19 (0.47 g, 2.3 mmol), 4'-hydroxyflavone (0.54 g, 2.3 mmol) and PPh$_3$ (0.66 g, 2.5 mmol) in THF (20 mL), was added DIAD (0.51 g, 2.5 mmol) dropwise. The reaction mixture was further headed to reflux for 12 h. The reaction mixture was evaporated under reduced pressure to give brown oil which was subjected flash column chromatography on silica gel with gradient elution (20% acetone in DCM to 80% acetone to DCM) to furnish the desired product FM13 (0.32 g) in 33% yield: $^1$H NMR (400 MHz, CHLOROFORM-d) δ 8.55 (d, J=5.38 Hz, 2H), 8.22 (d, J=7.82 Hz, 1H), 7.87 (d, J=8.80 Hz, 2H), 7.66-7.70 (m, 1H), 7.55 (d, J=8.31 Hz, 1H), 7.41 (t, J=7.34 Hz, 1H), 7.29 (d, J=4.89 Hz, 2H), 7.01 (d, J=8.80 Hz, 2H), 6.74 (s, 1H), 3.89 (d, J=5.87 Hz, 2H), 3.52 (s, 2H), 2.91 (d, J=11.25 Hz, 2H), 2.07 (t, J=10.76 Hz, 2H), 1.85 (d, J=8.80 Hz, 3H), 1.41-1.52 (m, 2H); $^{13}$C NMR (101 MHz, CHLOROFORM-d) δ 178.4, 163.4, 162.0, 156.2, 149.7, 148.1, 133.6, 128.0, 125.7, 125.1, 123.9, 123.9, 123.9, 118.0, 114.9, 106.1, 72.8, 62.1, 53.5, 35.7, 29.1; LRMS (ESI) m/z 427 (M$^+$+H, 100); HRMS (ESI) calcd for $C_{27}H_{27}N_2O_3$ (M$^+$+H) 427.2022, Found 427.2009.

The detailed chemical synthesis of flavonoid monomer FM14 is described as shown in the scheme 14.

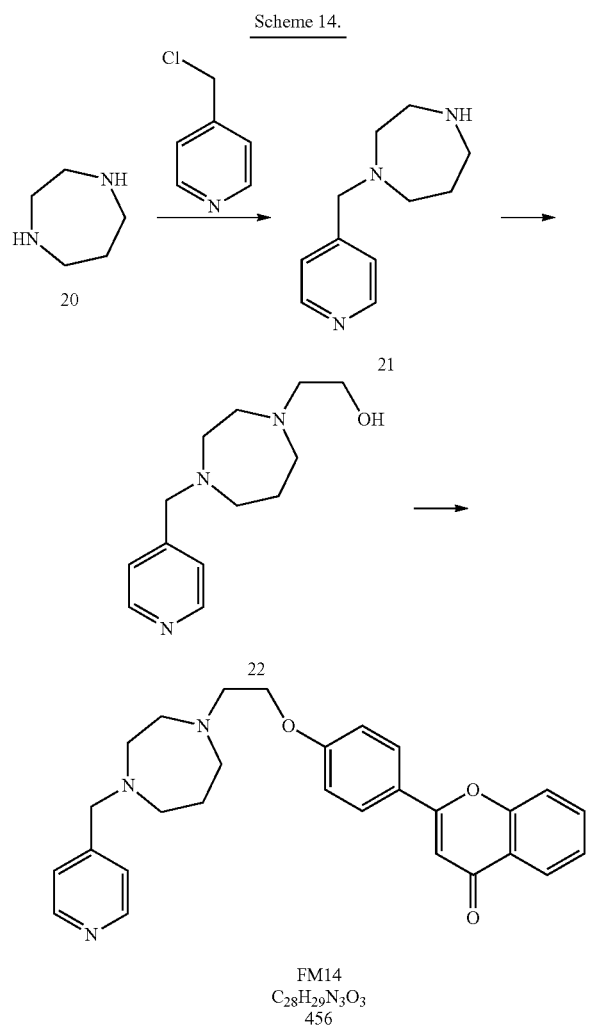

2-(4-(2-(4-(pyridin-4-ylmethyl)-1,4-diazepan-1-yl)ethoxy)phenyl)-4H-chromen-4-one (FM14)

To a well stirred mixture of diamine 20 (17 g, 170 mmol) and 4-chloromethylpyridine hydrochloride (12 g, 73 mmol) and $K_2CO_3$ (11 g, 80 mmol) in MeOH (100 mL) at room temperature, was stirred for 16 h. After that, the mixture was poured into separating funnel containing 5% NaOH solution (200 mL) and extracted with DCM (50 mL×3). The combined organic layers were dried over $MgSO_4$, filtered and evaporated to crude brown oil which was subjected to vacuum distillation to furnish diamine 21 (5.4 g, 28 mmol) in 39% yield. To a well stirred mixture of diamine 21 (5.0 g, 26 mmol), 2-bromoethanol (3.6 g, 29 mmol) and $K_2CO_3$ (4.0 g, 29 mmol) in ACN (60 mL), was heated to reflux for 14 h. The mixture was filtered and evaporated under reduced pressure to give brown oil which was subjected flash column chromatography on silica gel with gradient elution (3% MeOH in DCM to 8% MeOH in DCM) to furnish alcohol 22 (3.1 g, 13 mmol) in 50% yield. To a well stirred mixture of alcohol 22 (0.64 g, 2.7 mmol), 4'-hydroxyflavone (0.64 g, 2.7 mmol) and PPh$_3$ (0.80 g, 3.1 mmol) in THF (30 mL), was added DIAD (0.61 g, 3.0 mmol) dropwise. The reaction mixture was further heated to reflux for 12 h. The reaction mixture was evaporated under reduced pressure to give brown oil which was subjected flash column chromatography on silica gel with gradient elution (20% acetone in DCM to 80% acetone to DCM) to furnish the desired product FM14 (0.36 g, 0.79 mmol) in 29% yield: $^1$H NMR (400 MHz, CHLOROFORM-d) δ 8.51 (d, J=5.38 Hz, 2H), 8.19 (d, J=7.82 Hz, 1H), 7.84 (d, J=8.80 Hz, 2H), 7.63-7.67 (m, 1H), 7.52 (d, J=8.31 Hz, 1H), 7.37 (t, J=7.34 Hz, 1H), 7.26 (d, J=5.87 Hz, 4H), 7.00 (d, J=8.80 Hz, 2H), 6.71 (s, 1H), 4.12 (t, J=5.87 Hz, 2H), 3.58-3.69 (m, 2H), 3.00 (t, J=5.87 Hz, 2H), 2.82-2.90 (m, 4H), 2.62-2.75 (m, 6H), 1.74-1.85 (m, 2H), 1.20-1.25 (m, 2H); $^{13}$C NMR (101 MHz, CHLOROFORM-d) δ 178.3, 163.3, 161.7, 156.1, 149.7, 148.9, 133.5, 128.0, 125.6, 125.0, 124.0, 123.9, 123.6, 117.9, 115.0, 106.1, 66.8, 61.7, 56.4, 55.7, 55.3, 54.6, 54.5, 27.8, 22.0; LRMS (ESI) m/z 456 (M$^+$+H, 100); HRMS (ESI) calcd for $C_{28}H_{30}N_3O_3$ (M$^+$+H) 456.2287, Found 456.2277.

The detailed chemical synthesis of flavonoid monomer FM15 is described as shown in the scheme 15.

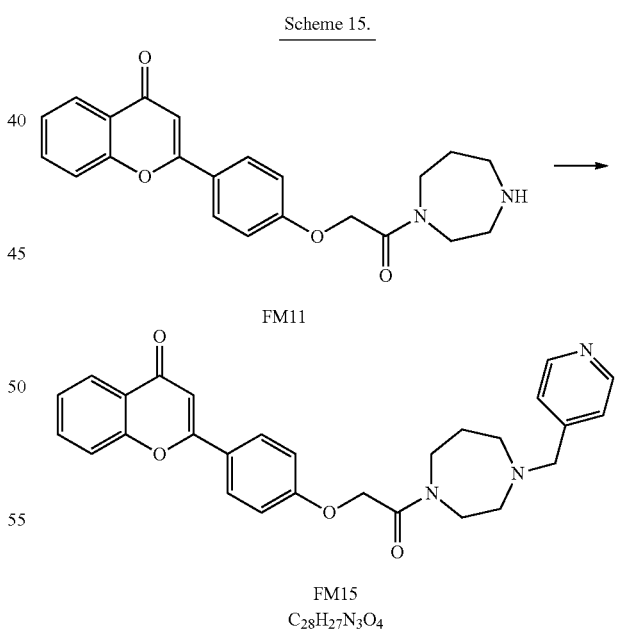

2-(4-(2-oxo-2-(4-(pyridin-4-ylmethyl)-1,4-diazepan-1-yl)ethoxy)phenyl)-4H-chromen-4-one (FM15)

To a well stirred mixture of FM11 (0.50 g, 1.3 mmol), 4-chloromethylpyridine hydrochloride (0.30 g, 1.8 mmol)

and K$_2$CO$_3$ (0.50 g) in MeOH (30 mL), the mixture was heated to reflux for 4 h. The reaction mixture was then filtered to remove excess K$_2$CO$_3$. The obtained filtrate was evaporated under reduced pressure to give oily crude mixture which was subjected to flash column chromatography on silica gel with gradient elution (20% acetone in DCM to 80% acetone to DCM) to furnish the desired product FM15 (0.35 g, 0.74 mmol) in 41% yield: $^1$H NMR (400 MHz, CHLOROFORM-d) 8.54 (dd, J=5.87, 7.34 Hz, 2H), 8.22 (d, J=7.82 Hz, 1H), 7.89 (dd, J=2.93, 8.80 Hz, 2H), 7.67-7.72 (m, 1H), 7.55 (d, J=8.31 Hz, 1H), 7.41 (t, J=7.58 Hz, 1H), 7.26 (dd, J=5.62, 9.05 Hz, 3H), 7.09 (dd, J=5.38, 8.80 Hz, 2H), 6.75 (s, 1H), 4.81 (d, J=11.74 Hz, 2H), 3.55-3.74 (m, 6H), 2.55-2.81 (m, 4H), 1.86-1.98 (m, 2H); $^{13}$C NMR (101 MHz, CHLOROFORM-d) δ 178.3, 167.0, 166.9, 163.1, 160.8, 160.7, 156.2, 149.9, 149.9, 148.1, 133.7, 128.1, 125.7, 125.1, 125.0, 123.9, 123.5, 123.4, 118.0, 115.2, 106.5, 77.3, 67.6, 67.5, 61.5, 61.2, 55.6, 55.3, 54.1, 47.7, 46.4, 46.0, 45.3, 28.7, 27.1; LRMS (ESI) m/z 470 (M$^+$+H, 100); HRMS (ESI) calcd for C$_{28}$H$_{28}$N$_3$O$_4$ (M$^+$+H) 470.2080, Found 470.2063.

The detailed chemical synthesis of flavonoid monomer FM16 is described as shown in the scheme 16.

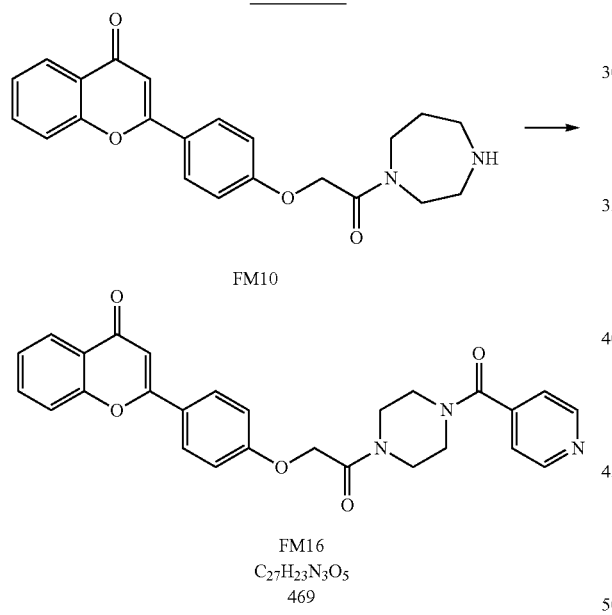

Scheme 16.

FM10

FM16
C$_{27}$H$_{23}$N$_3$O$_5$
469

2-(4-(2-(4-isonicotinoylpiperazin-1-yl)-2-oxoethoxy)phenyl)-4H-chromen-4-one (FM16)

To well stirred solution of FM10 (0.31 g, 0.85 mmol) in pyridine (10 mL) at 0° C., was added isonicotinoyl chloride (0.20 g, 1.4 mmol) at once. The mixture was stirred further for 4 h. After that, the reaction mixture was washed with 1 M HCl solution and saturated NaHCO$_3$ solution. The organic layer was dried over MgSO$_4$, filtered and evaporated under reduced pressure to give pale brown oil which was subjected to flash column chromatography on silica gel with gradient elution (20% acetone in DCM to 70% acetone in DCM) to furnish the desired product FM16 (0.32 g, 0.68 mmol) in 56% yield: $^1$H NMR (400 MHz, CHLOROFORM-d) δ 8.73 (d, J=5.87 Hz, 2H), 8.20-8.29 (m, 1H), 7.84-8.04 (m, 2H), 7.63-7.78 (m, 1H), 7.56 (d, J=8.31 Hz, 1H), 7.43 (t, J=7.34 Hz, 1H), 7.30 (s, 2H), 7.10 (br. s., 2H), 6.76 (s, 1H), 4.85 (br. s., 2H), 3.69-3.94 (m, 4H), 3.63 (br. s., 2H), 3.40 (br. s., 2H); $^{13}$C NMR (101 MHz, CHLOROFORM-d) δ 178.3, 166.2, 162.9, 160.2, 156.2, 150.5, 149.9, 133.7, 128.3, 125.7, 125.5, 125.2, 123.9, 123.4, 121.1, 118.0, 115.1, 106.6, 77.2, 67.8, 60.2, 45.4, 45.1; LRMS (ESI) m/z 470 (M$^+$+H, 100), 492 (M$^+$+Na, 10); HRMS (ESI) calcd for C$_{27}$H$_{24}$N$_3$O$_5$ (M$^+$+H) 470.1716, Found 470.1694.

The detailed chemical synthesis of flavonoid monomer FM17 is described as shown in the scheme 17.

Scheme 17.

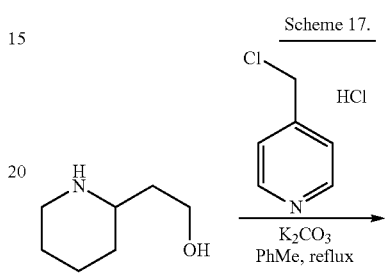

23

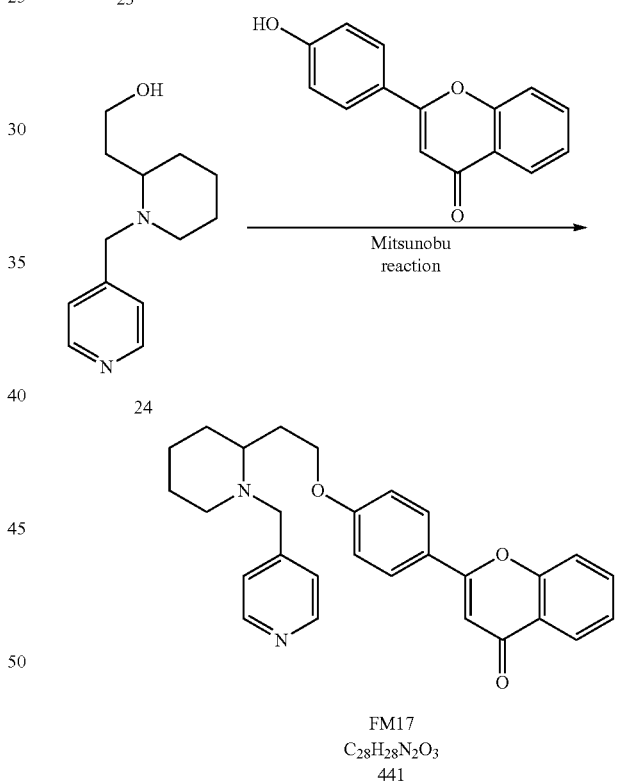

24

Mitsunobu reaction

FM17
C$_{28}$H$_{28}$N$_2$O$_3$
441

2-(4-(2-(1-(pyridin-4-ylmethyl)piperidin-2-yl)ethoxy)phenyl)-4H-chromen-4-one (FM17)

To a well stirred mixture of hydroxylamine 23 (5.3 g, 41 mmol), 4-chloromethylpyridine hydrochloride (7.0 g, 42 mmol) and K$_2$CO$_3$ (12.3 g) in toluene (80 mL), the mixture was heated to reflux for 14 h. The reaction mixture was then filtered to remove excess K$_2$CO$_3$. The obtained filtrate was evaporated under reduced pressure to give oily crude mixture which was subjected vacuum distillation to furnish alcohol 24 (3.7 g, 17 mmol) in 41% yield: $^1$H NMR (400 MHz, CHLOROFORM-d) δ 8.47 (d, J=4.89 Hz, 2H), 7.22 (d, J=4.89 Hz, 2H), 4.67 (br. s., 1H), 4.05 (s, 1H), 3.84 (br. s., 1H), 3.71 (br. s., 1H), 3.34 (s, 1H), 2.74-2.90 (m, 1H), 2.63 (br. s., 1H), 2.04-2.15 (m, 1H), 1.63-1.92 (m, 4H), 1.32-1.59 (m, 4H); $^{13}$C NMR (101 MHz, CHLOROFORM-d) δ 149.7, 148.6, 123.7, 61.1, 59.5, 56.6, 50.4, 32.5, 28.3, 23.3, 22.7; Alcohol 24 was used for next step without further purification. To a well stirred mixture of alcohol 24 (0.54 g, 2.5 mmol), 4'-hydroxyflavone (0.60 g, 2.5 mmol) and PPh$_3$ (0.71 g, 2.7 mmol) in THF (20 mL), was added DIAD (0.55 g, 2.7 mmol) dropwise. The reaction mixture was further headed to reflux for 12 h. The reaction mixture was evaporated under reduced pressure to give brown oil which was subjected flash column chromatography on silica gel with gradient elution (20% acetone in DCM to 80% acetone to DCM) to furnish the desired product FM17 (0.34 g, 0.77 mmol) in 31% yield: $^1$H NMR (400 MHz, CHLOROFORM-d) δ 8.44 (d, J=5.87 Hz, 2H), 8.12 (dd, J=0.98, 7.83 Hz, 1H), 7.75 (d, J=8.80 Hz, 2H), 7.55-7.60 (m, 1H), 7.44 (d, J=8.31 Hz, 1H), 7.29 (t, J=7.34 Hz, 1H), 7.21 (d, J=5.38 Hz, 2H), 6.87 (d, J=8.80 Hz, 2H), 6.63 (s, 1H), 3.97-4.07 (m, 2H), 3.88 (d, J=14.67 Hz, 1H), 3.30 (d, J=15.16 Hz, 1H), 2.56-2.69 (m, 2H), 2.03-2.15 (m, 2H), 1.89-1.96 (m, 1H), 1.59-1.74 (m, 2H), 1.31-1.50 (m, 4H); $^{13}$C NMR (101 MHz, CHLOROFORM-d) δ 178.1, 163.2, 161.7, 156.0, 149.6, 149.4, 133.5, 127.9, 125.5, 125.0, 123.8, 123.7, 123.4, 117.9, 114.8, 106.0, 77.5, 65.4, 57.4, 56.7, 51.1, 30.3, 29.7, 24.5, 22.7; LRMS (ESI) m/z 441 (M$^+$+H, 100), 463 (M++Na, 21); HRMS (ESI) calcd for C$_{28}$H$_{29}$N$_2$O$_3$ (M$^+$+H) 441.2178, Found 441.2166.

The detailed chemical synthesis of flavonoid monomer FM18 is described as shown in the scheme 18.

Scheme 18.

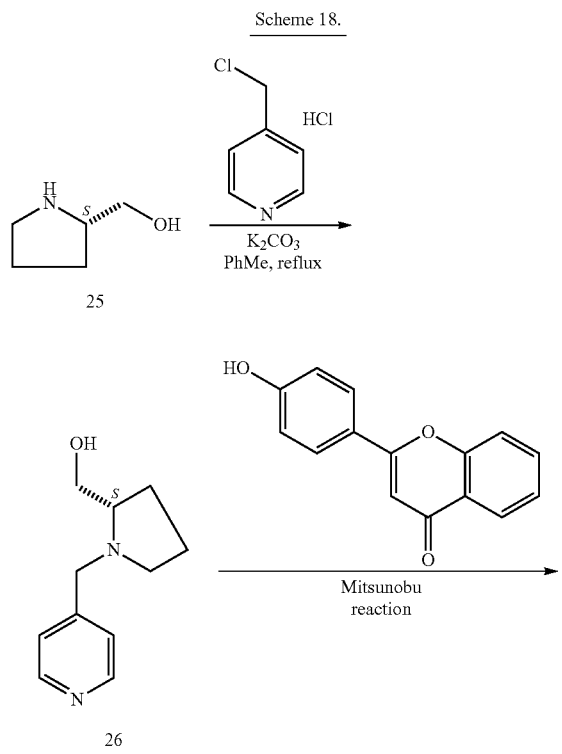

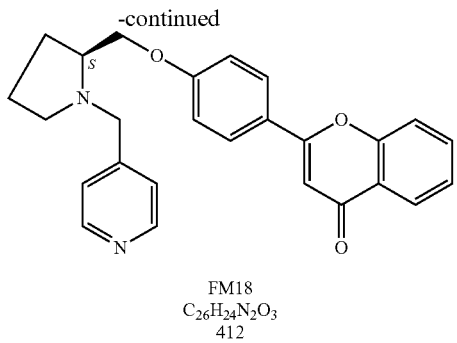

FM18
C$_{26}$H$_{24}$N$_2$O$_3$
412

(S)-2-(4-((1-(pyridin-4-ylmethyl)pyrrolidin-2-yl)methoxy)phenyl)-4H-chromen-4-one (FM18)

To a well stirred mixture of hydroxylamine 25 (3.0 g, 30 mmol), 4-chloromethylpyridine hydrochloride (5.3 g, 32 mmol) and K$_2$CO$_3$ (8.5 g) in toluene (60 mL), the mixture was heated to reflux for 14 h. The reaction mixture was then filtered to remove excess K$_2$CO$_3$. The obtained filtrate was evaporated under reduced pressure to give oily crude mixture which was subjected vacuum distillation to furnish alcohol 26 (2.4 g) in 42% yield: $^1$H NMR (400 MHz, CHLOROFORM-d) δ 8.43-8.59 (m, 2H), 7.22 (d, J=4.40 Hz, 2H), 3.98 (s, 1H), 3.58-3.71 (m, 1H), 3.46 (s, 1H), 3.26-3.42 (m, 1H), 3.07 (br. s., 2H), 2.94 (dd, J=4.65, 8.56 Hz, 1H), 2.66-2.80 (m, 1H), 2.15-2.29 (m, 1H), 1.85-2.00 (m, 1H), 1.63-1.85 (m, 3H); $^{13}$C NMR (101 MHz, CHLOROFORM-d) δ 149.7, 148.8, 123.5, 64.8, 62.5, 57.8, 54.6, 27.6, 23.4; Alcohol 26 was used for next step without further purification. To a well stirred mixture of alcohol 26 (0.45 g, 2.3 mmol), 4'-hydroxyflavone (0.56 g, 2.4 mmol) and PPh$_3$ (0.71 g, 2.7 mmol) in THF (20 mL), was added DIAD (0.55 g, 2.7 mmol) dropwise. The reaction mixture was further headed to reflux for 12 h. The reaction mixture was evaporated under reduced pressure to give brown oil which was subjected flash column chromatography on silica gel with gradient elution (20% acetone in DCM to 80% acetone to DCM) to furnish the desired product FM18 (0.34 g, 0.82 mmol) in 36% yield: $^1$H NMR (400 MHz, CHLOROFORM-d) δ 8.52-8.57 (m, 2H), 8.23 (d, J=7.82 Hz, 1H), 7.84-7.90 (m, 2H), 7.66-7.71 (m, 1H), 7.56 (d, J=8.31 Hz, 1H), 7.41 (t, J=7.58 Hz, 1H), 7.27-7.32 (m, 2H), 6.97-7.04 (m, 2H), 6.75 (d, J=2.93 Hz, 1H), 3.89-4.09 (m, 2H), 3.54-3.61 (m, 1H), 2.96-3.15 (m, 1H), 2.28-2.37 (m, 1H), 2.05-2.23 (m, 3H), 1.66-1.90 (m, 3H); $^{13}$C NMR (101 MHz, CHLOROFORM-d) δ 178.4, 163.4, 163.3, 161.7, 160.5, 156.2, 149.8, 149.8, 149.1, 147.5, 133.6, 128.1, 128.0, 125.7, 125.1, 124.1, 124.0, 124.0, 123.7, 123.6, 118.0, 115.9, 114.9, 106.2, 106.2, 77.3, 73.0, 71.9, 62.6, 61.6, 58.8, 57.5, 54.9, 53.3; 29.7, 28.6, 23.3, 23.0; LRMS (ESI) m/z 413 (M++H, 100), 435 (M$^+$+Na, 11); HRMS (ESI) calcd for C$_{26}$H$_{25}$N$_2$O$_3$ (M++H) 413.1865, Found 413.1870.

The detailed chemical synthesis of flavonoid monomer FM21 is described as shown in the scheme 19.

Scheme 19.

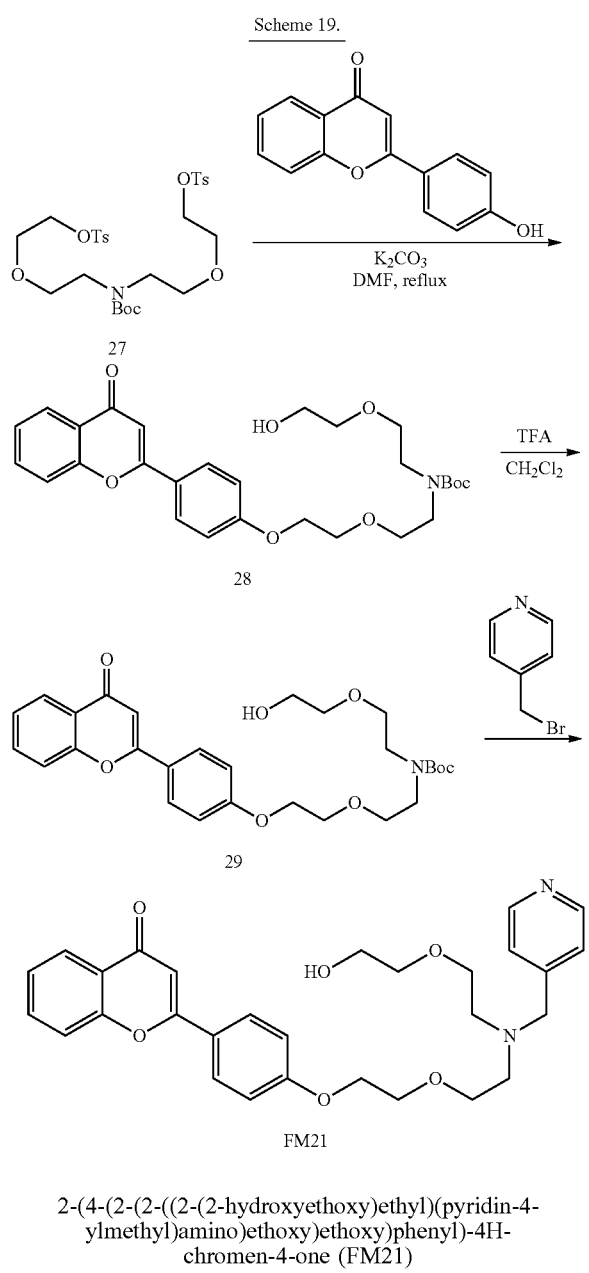

2-(4-(2-(2-((2-(2-hydroxyethoxy)ethyl)(pyridin-4-ylmethyl)amino)ethoxy)ethoxy)phenyl)-4H-chromen-4-one (FM21)

To a well stirred mixture of ditosylate 27 (6.0 g, 10 mmol), 4'-hydroxyflavone (2.3 g, 10 mmol) and $K_2CO_3$ (3.0 g) in DMF (50 mL) was heated to reflux for 4 h. After cooling to room temperature, the reaction was quenched by pouring into a separating funnel containing 200 mL water and extracted with DCM (30 mL×3). The combined organic layers were dried over $MgSO_4$, filtered and evaporated under reduced pressure to give oily crude mixture which was subjected flash column chromatography on silica gel with gradient elution (20% acetone in DCM to 60% acetone in DCM) to furnish pale brown oil of alcohol 28 (2.3 g) in 45% yield: $^1H$ NMR (400 MHz, CHLOROFORM-d) δ 8.21 (d, J=7.2 Hz, 1H), 7.87 (d, J=8.4 Hz, 2H), 7.67 (d, J=6.4 Hz, 1H), 7.54 (d, J=8.0 Hz, 1H), 7.38 (d, J=6.4 Hz, 1H), 7.03 (d, J=8.4 Hz, 2H), 6.76 (s, 1H), 4.18 (t, J=4.2 Hz, 2H), 3.84 (s, 2H), 3.45-3.69 (m, 12H), 2.26 (br, 1H), 1.45 (s, 9H);

To a well stirred solution of alcohol 28 (1.2 g, 2.3 mmol) in DCM (30 mL) at 0° C., was added excess trifluoroacetic acid (10 mL). The reaction mixture turned clear yellow and stirred at room temperature for 2 h. After that, the reaction was quenched by pouring into a conical flask containing 100 mL water and basified with NaOH solution to pH 10. The mixture was extracted with DCM (30 mL×3). The combined organic layers were dried over $MgSO4$, filtered and evaporated to give the desired hydroxylamine 29 (0.90 g, 93%): $^1H$ NMR (400 MHz, CHLOROFORM-d) δ 8.19 (d, J=7.2 Hz, 1H), 7.85 (d, J=8.4 Hz, 2H), 7.65 (d, J=6.4 Hz, 1H), 7.52 (d, J=8.0 Hz, 1H), 7.36 (d, J=6.4 Hz, 1H), 7.00 (d, J=8.4 Hz, 2H), 6.71 (s, 1H), 4.18 (t, J=4.2 Hz, 2H), 3.84 (t, J=4.2 Hz, 2H), 3.55-3.71 (m, 8H), 2.87-2.91 (m, 4H);

To a well stirred mixture of hydroxylamine 29 (0.50 g, 1.2 mmol), 4-bromomethylpyridine hydrobromide (0.40 g, 1.6 mmol) and $K_2CO_3$ (0.42 g) in ACN (60 mL), the mixture was heated to reflux for 4 h. The reaction mixture was then filtered to remove excess $K_2CO_3$. The obtained filtrate was evaporated under reduced pressure to give crude mixture which was subjected flash column chromatography on silica gel with gradient elution (20% acetone in DCM to 60% acetone in DCM) to furnish FM21 (0.13 g) in 21% yield: $^1H$ NMR (400 MHz, CHLOROFORM-d) δ 8.42-8.49 (m, 2H), 8.15 (dd, J=1.47, 7.82 Hz, 1H), 7.77-7.84 (m, 2H), 7.59-7.66 (m, 1H), 7.45-7.53 (m, 1H), 7.34 (dt, J=1.22, 7.46 Hz, 1H), 7.28 (d, J=5.87 Hz, 2H), 6.92-6.99 (m, 2H), 6.68 (s, 1H), 4.07-4.15 (m, 2H), 3.70-3.78 (m, 4H), 3.65-3.70 (m, 2H), 3.63 (t, J=5.62 Hz, 2H), 3.55 (t, J=5.62 Hz, 2H), 3.47-3.52 (m, 2H), 2.70-2.80 (m, 4H); $^{13}C$ NMR (101 MHz, CHLOROFORM-d) δ 178.3, 163.3, 161.6, 156.1, 149.5, 149.1, 133.6, 127.9, 125.5, 125.1, 124.1, 123.8, 123.7, 118.0, 115.0, 106.1, 72.3, 69.9, 69.4, 69.3, 67.6, 61.6, 58.7, 54.3, 54.1; LRMS (ESI) m/z 505 ($M^+$+H, 100), 527 ($M^+$+Na, 20); HRMS (ESI) calcd for $C_{29}H_{33}N_2O_6$ ($M^+$+H) 505.2339, Found 505.2325.

The detailed chemical synthesis of flavonoid monomer FM09a is described as shown in the scheme 20.

Scheme 20

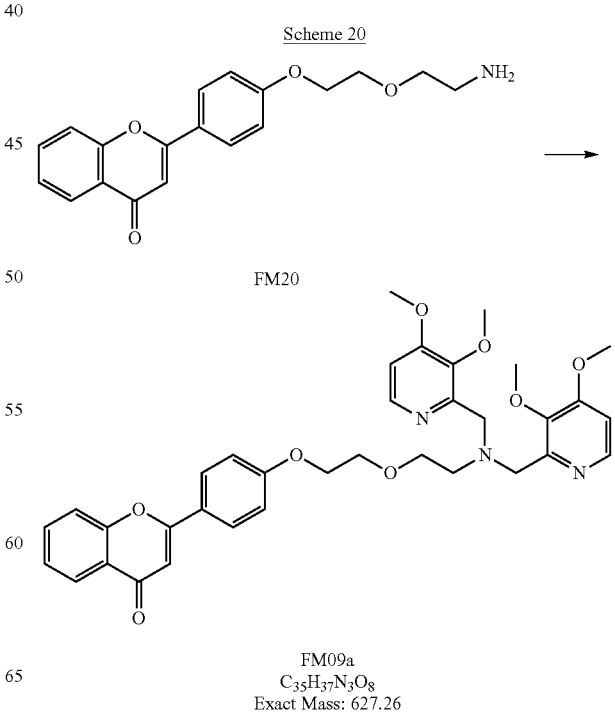

FM09a
$C_{35}H_{37}N_3O_8$
Exact Mass: 627.26

2-(4-(2-(2-(bis((3,4-dimethoxypyridin-2-yl)methyl)amino)ethoxy)ethoxy)phenyl)-4H-chromen-4-one (FM09a)

To a well stirred mixture of FM20 (0.15 g, 0.46 mmol), 2-(chloromethyl)-3,4-dimethoxypyridine hydrochloride (0.29 g, 1.3 mmol) and $K_2CO_3$ (0.20 g, 1.4 mmol) in ACN (20 mL), was heated to reflux for 4 h. After that, the reaction mixture was filtered and the obtained filtrate was evaporated under reduced pressure to give brown oil which was subjected to flash chromatography on silica gel with gradient elution (20% acetone in DCM to 70% acetone in DCM) to furnish FM09a (0.15 g, 0.25 mmol) in 52% yield: $^1$H NMR (400 MHz, CDCl$_3$) δ 8.20-8.14 (m, 3H), 7.81 (d, J=8.8 Hz, 2H), 7.67-7.61 (m, 1H), 7.51 (d, J=8.3 Hz, 1H), 7.36 (t, J=7.5 Hz, 1H), 6.97 (d, J=8.9 Hz, 2H), 6.73 (d, J=5.5 Hz, 2H), 6.69 (s, 1H), 4.10-4.06 (m, 2H), 3.93 (s, 4H), 3.84 (s, 6H), 3.74-3.70 (m, 8H), 3.65 (t, J=6.2 Hz, 2H), 2.86 (t, J=6.2 Hz, 2H); $^{13}$C NMR (101 MHz, CDCl$_3$) δ 178.4, 163.3, 161.7, 159.8, 158.2, 156.2, 140.4, 133.6, 127.9, 125.6, 125.1, 124.1, 123.9, 123.5, 118.0, 115.1, 106.5, 106.2, 69.9, 69.2, 67.7, 60.9, 60.4, 56.1, 53.6; LRMS (ESI) m/z 628 (M$^+$+H, 100), 650 (M$^+$+Na, 11); HRMS (ESI) calcd for $C_{35}H_{37}N_3O_8$ (M$^+$+H) 628.2657, Found 628.2651.

The detailed chemical synthesis of flavonoid monomer FM09b is described as shown in the scheme 21.

Scheme 21

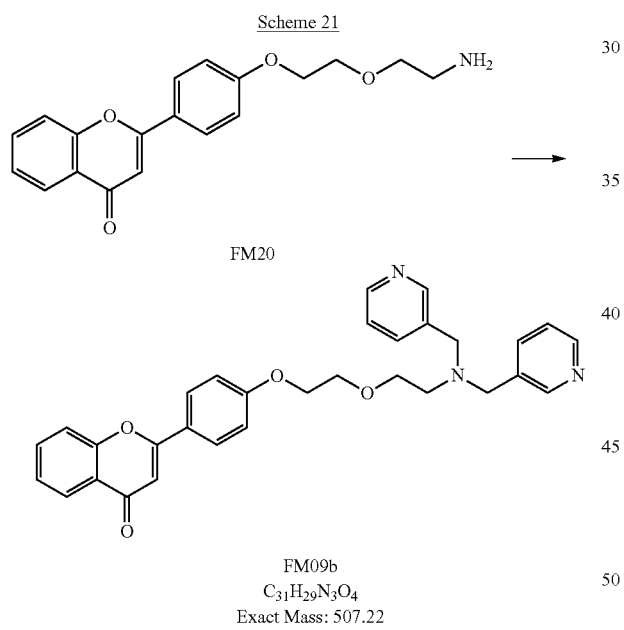

FM09b
$C_{31}H_{29}N_3O_4$
Exact Mass: 507.22

2-(4-(2-(2-(bis(pyridin-3-ylmethyl)amino)ethoxy)ethoxy)phenyl)-4H-chromen-4-one (FM09b)

To a well stirred mixture of FM20 (0.15 g, 0.46 mmol), 3-(chloromethyl)pyridine hydrochloride (0.21 g, 1.3 mmol) and $K_2CO_3$ (0.20 g, 1.4 mmol) in ACN (20 mL), was heated to reflux for 4 h. After that, the reaction mixture was filtered and the obtained filtrate was evaporated under reduced pressure to give brown oil which was subjected to flash chromatography on silica gel with gradient elution (20% acetone in DCM to 70% acetone in DCM) to furnish FM09b (0.13 g, 0.25 mmol) in 53% yield: 1H NMR (400 MHz, CDCl3) δ 8.59 (d, J=4.4 Hz, 2H), 8.20 (d, J=7.8 Hz, 2H), 7.83 (d, J=8.8 Hz, 2H), 7.51-7.68 (m, 6H), 7.38 (t, J=7.3 Hz, 1H), 7.09-7.13 (m, 2H), 6.99 (d, J=8.8 Hz, 2H), 6.71 (s, 1H), 4.13-4.17 (m, 2H), 3.86 (s, 4H), 3.76-3.80 (m, 2H), 3.70 (t, J=5.9 Hz, 2H), 2.86 (t, J=5.9 Hz, 2H); $^{13}$C NMR (101 MHz, CDCl$_3$) δ 178.4, 163.3, 161.6, 156.1, 151.8, 147.2, 144.4, 136.5, 133.6, 128.0, 125.6, 125.1, 124.1, 123.9, 123.5, 118.0, 115.1, 106.2, 69.9, 69.3, 68.0, 60.9, 53.6; LRMS (ESI) m/z 508 (M$^+$+H, 100), 530 (M$^+$+Na, 9); HRMS (ESI) calcd for $C_{31}H_{30}N_3O_4$ (M$^+$+H) 508.2236, Found 508.2238.

The detailed chemical synthesis of flavonoid monomer FM09c is described as shown in the scheme 22.

Scheme 22

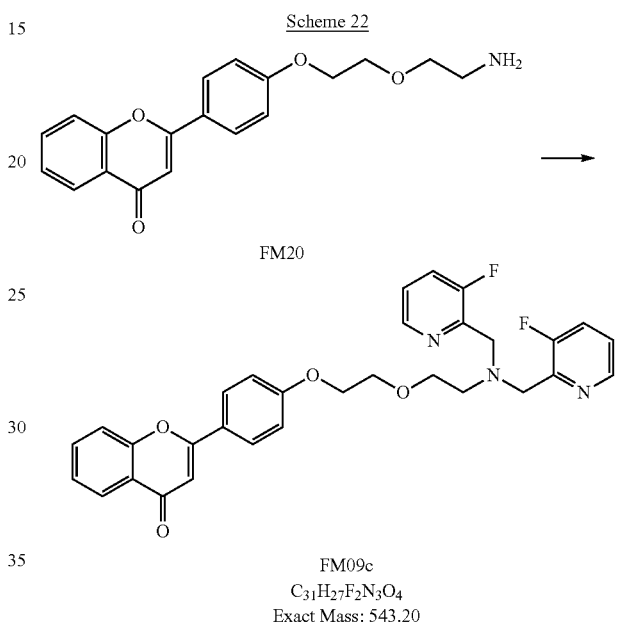

FM09c
$C_{31}H_{27}F_2N_3O_4$
Exact Mass: 543.20

2-(4-(2-(2-(bis((3-fluoropyridin-2-yl)methyl)amino)ethoxy)ethoxy)phenyl)-4H-chromen-4-one (FM09c)

To a well stirred mixture of FM20 (0.15 g, 0.46 mmol), 2-(chloromethyl)-3-fluoropyridine hydrochloride (0.24 g, 1.3 mmol) and $K_2CO_3$ (0.20 g, 1.4 mmol) in ACN (20 mL), was heated to reflux for 4 h. After that, the reaction mixture was filtered and the obtained filtrate was evaporated under reduced pressure to give brown oil which was subjected to flash chromatography on silica gel with gradient elution (20% acetone in DCM to 70% acetone in DCM) to furnish FM09c (0.14 g, 0.25 mmol) in 52% yield: $^1$H NMR (400 MHz, CDCl$_3$) δ 8.35 (d, J=4.6 Hz, 2H), 8.20 (dd, J=7.9, 1.3 Hz, 1H), 7.83 (d, J=8.9 Hz, 2H), 7.70-7.63 (m, 1H), 7.53 (d, J=8.3 Hz, 1H), 7.39 (t, J=7.5 Hz, 1H), 7.31 (dd, J=13.8, 5.2 Hz, 2H), 7.18 (dt, J=8.4, 4.3 Hz, 2H), 6.99 (d, J=8.9 Hz, 2H), 6.71 (s, 1H), 4.15-4.11 (m, 2H), 4.05 (s, 2H), 4.04 (s, 2H), 3.80-3.76 (m, 2H), 3.71 (t, J=5.9 Hz, 2H), 2.94 (t, J=5.9 Hz, 2H); $^{13}$C NMR (101 MHz, CDCl$_3$) δ 178.4, 163.3, 161.6, 159.8, 156.1, 147.7, 144.1, 133.6, 128.0, 125.6, 125.1, 124.1, 123.9, 123.5, 120.3, 118.0, 115.1, 106.2, 69.8, 69.3, 67.8, 60.8, 53.5; LRMS (ESI) m/z 544 (M$^+$+H, 100), 566 (M$^+$+Na, 15); HRMS (ESI) calcd for $C_{31}H_{27}F_2N_3O_4$(M++H) 544.2016, Found 544.1998.

The detailed chemical synthesis of flavonoid monomer FM09d is described as shown in the scheme 23.

Scheme 23

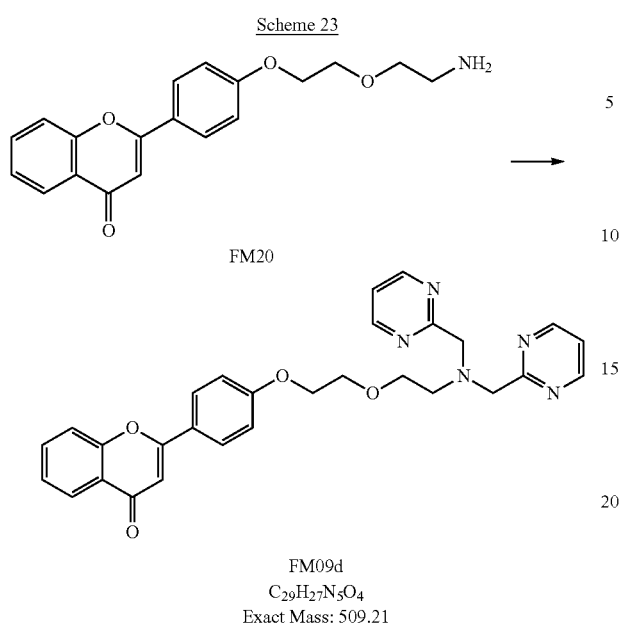

FM09d
C29H27N5O4
Exact Mass: 509.21

2-(4-(2-(2-(bis(pyrimidin-2-ylmethyl)amino)ethoxy)ethoxy)phenyl)-4H-chromen-4-one (FM09d)

To a well stirred mixture of FM20 (0.15 g, 0.46 mmol), 2-(chloromethyl)pyrimidine hydrochloride (0.21 g, 1.3 mmol) and $K_2CO_3$ (0.20 g, 1.4 mmol) in ACN (20 mL), was heated to reflux for 4 h. After that, the reaction mixture was filtered and the obtained filtrate was evaporated under reduced pressure to give brown oil which was subjected to flash chromatography on silica gel with gradient elution (20% acetone in DCM to 70% acetone in DCM) to furnish FM09d (0.13 g, 0.25 mmol) in 51% yield: $^1$H NMR (400 MHz, CDCl3) δ 8.66 (d, J=4.9 Hz, 4H), 8.17 (dd, J=7.9, 1.4 Hz, 1H), 7.82 (d, J=8.9 Hz, 3H), 7.68-7.62 (m, 1H), 7.52 (d, J=8.3 Hz, 1H), 7.37 (t, J=7.5 Hz, 1H), 7.12 (t, J=4.9 Hz, 2H), 6.97 (d, J=8.9 Hz, 2H), 6.70 (s, 1H), 4.25 (s, 4H). 4.13-4.10 (m, 2H), 3.78-3.75 (m, 2H), 3.58-3.56 (m, 2H), 3.07-3.05 (m, 2H); $^{13}$C NMR (101 MHz, CDCl$_3$) δ 178.3, 167.8, 163.3, 161.7, 157.2, 156.1, 133.4, 128.0, 125.6, 125.0, 124.1, 123.9, 118.0, 114.6, 113.5, 106.2, 69.7, 69.3, 67.7, 61.2, 53.1; LRMS (ESI) m/z 510 (M$^+$+H, 100), 532 (M$^+$+Na, 16); HRMS (ESI) calcd for $C_{29}H_{27}N_5O_4$ (M$^+$+H) 510.2176, Found 510.2169.

The detailed chemical synthesis of flavonoid monomer FM09e is described as shown in the scheme 24.

Scheme 24

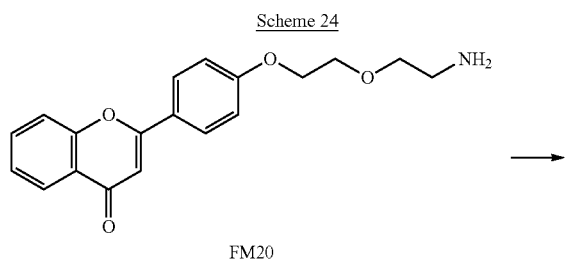

FM20

-continued

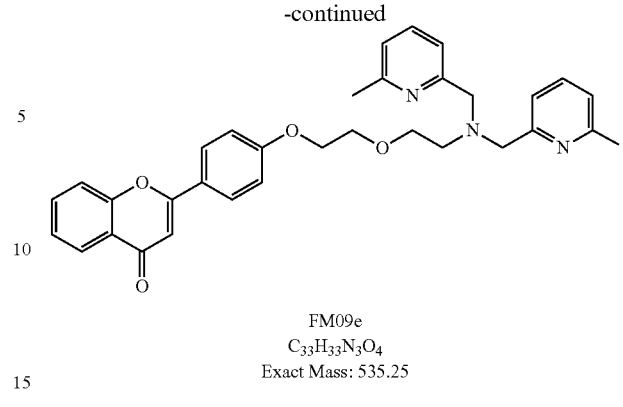

FM09e
C33H33N3O4
Exact Mass: 535.25

2-(4-(2-(2-(bis((6-methylpyridin-2-yl)methyl)amino)ethoxy)ethoxy)phenyl)-4H-chromen-4-one (FM09e)

To a well stirred mixture of FM20 (0.15 g, 0.46 mmol), 2-(chloromethyl)-6-methylpyridine hydrochloride (0.23 g, 1.3 mmol) and $K_2CO_3$ (0.20 g, 1.4 mmol) in ACN (20 mL), was heated to reflux for 4 h. After that, the reaction mixture was filtered and the obtained filtrate was evaporated under reduced pressure to give brown oil which was subjected to flash chromatography on silica gel with gradient elution (20% acetone in DCM to 70% acetone in DCM) to furnish FM09e (0.13 g, 0.25 mmol) in 51% yield: $^1$H NMR (400 MHz, DMSO) δ 8.27 (d, J=8.5 Hz, 2H), 8.04 (dd, J=7.9, 1.1 Hz, 1H), 7.98-7.94 (m, 3H), 7.76-7.70 (m, 3H) 7.54-7.45 (m, 3H), 7.05 (d, J=8.6 Hz, 2H), 6.90 (s, 1H), 4.15 (s, 2H), 4.03 (s, 4H), 3.71-3.68 (m, 2H), 3.65 (t, J=5.6 Hz, 2H), 3.39 (s, 6H), 2.80 (t, J=5.6 Hz, 2H); $^{13}$C NMR (101 MHz, CDCl$_3$) δ 178.3, 163.2, 161.5, 157.8, 155.9, 156.0, 136.1, 133.4, 128.0, 125.7, 125.1, 124.2, 124.1, 121.5, 120.3, 118.0, 115.1, 106.3, 69.9, 69.0, 67.8, 60.9, 53.8, 26.1; LRMS (ESI) m/z 536 (M$^+$+H, 100), 558 (M$^+$+Na, 11); HRMS (ESI) calcd for $C_{33}H_{33}N_3O_4$ (M$^+$+H) 536.2502, Found 536.2509.

The detailed chemical synthesis of flavonoid monomer FM09g is described as shown in the scheme 25.

Scheme 25

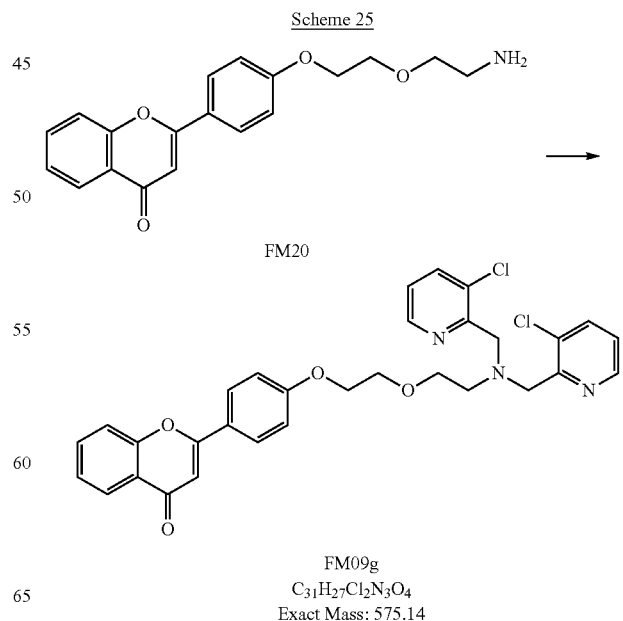

FM09g
C31H27Cl2N3O4
Exact Mass: 575.14

2-(4-(2-(2-(bis((3-chloropyridin-2-yl)methyl)amino)ethoxy)ethoxy)phenyl)-4H-chromen-4-one (FM09g)

To a well stirred mixture of FM20 (0.15 g, 0.46 mmol), 3-chloro-2-(chloromethyl)pyridine hydrochloride (0.26 g, 1.3 mmol) and $K_2CO_3$ (0.20 g, 1.4 mmol) in ACN (20 mL), was heated to reflux for 4 h. After that, the reaction mixture was filtered and the obtained filtrate was evaporated under reduced pressure to give brown oil which was subjected to flash chromatography on silica gel with gradient elution (20% acetone in DCM to 70% acetone in DCM) to furnish FM09g (0.14 g, 0.25 mmol) in 51% yield: $^1$H NMR (400 MHz, CDCl$_3$) δ 8.41 (dd, J=4.6, 1.1 Hz, 2H), 8.19 (dd, J=7.9, 1.1 Hz, 1H), 7.82 (d, J=8.8 Hz, 2H), 7.68-7.63 (m, 1H), 7.57 (dd, J=8.0, 1.2 Hz, 2H), 7.52 (d, J=8.3 Hz, 1H), 7.38 (t, J=7.5 Hz, 1H), 7.09 (dd, J=8.0, 4.7 Hz, 2H), 6.98 (d, J=8.8 Hz, 2H), 6.70 (s, 1H), 4.13-4.10 (m, 2H), 4.09 (s, 4H), 3.78-3.74 (m, 2H), 3.69 (t, J=5.9 Hz, 2H), 3.00 (t, J=5.9 Hz, 2H); $^{13}$C NMR (101 MHz, CDCl$_3$) δ 178.4, 163.3, 161.7, 159.8, 156.1, 147.2, 134.5, 133.5, 132.1, 128.1, 125.6, 125.1, 124.1, 123.8, 119.3, 118.0, 115.0, 106.2, 69.9, 69.3, 67.7, 60.8, 53.4; LRMS (ESI) m/z 576 (M$^+$+H, 100), 598 (M$^+$+Na, 10); HRMS (ESI) calcd for $C_{31}H_{27}Cl_2N_3O_4$ (M$^+$+H) 576.1463, Found 576.1448.

The detailed chemical synthesis of flavonoid monomer FM09h is described as shown in the scheme 26.

Scheme 26

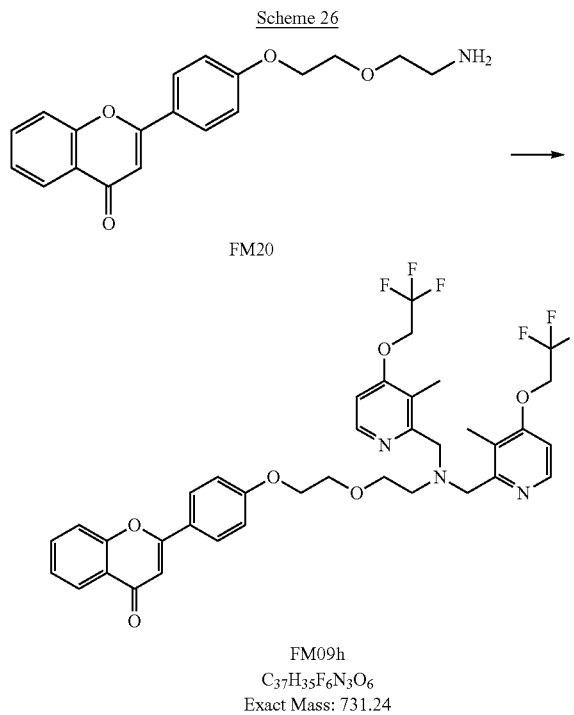

FM09h
$C_{37}H_{35}F_6N_3O_6$
Exact Mass: 731.24

2-(4-(2-(2-(bis((3-methyl-4-(2,2,2-trifluoroethoxy)pyridin-2-yl)methyl)amino)ethoxy)ethoxy)phenyl)-4H-chromen-4-one (FM09h)

To a well stirred mixture of FM20 (0.15 g, 0.46 mmol), 2-(chloromethyl)-3-methyl-4-(2,2,2-trifluoroethoxy)pyridine hydrochloride (0.36 g, 1.3 mmol) and $K_2CO_3$ (0.20 g, 1.4 mmol) in ACN (20 mL), was heated to reflux for 4 h. After that, the reaction mixture was filtered and the obtained filtrate was evaporated under reduced pressure to give brown oil which was subjected to flash chromatography on silica gel with gradient elution (20% acetone in DCM to 70% acetone in DCM) to furnish FM09h (0.18 g, 0.25 mmol) in 51% yield: $^1$H NMR (400 MHz, CDCl$_3$) δ 8.17 (d, J=4.6 Hz, 2H), 8.02 (d, J=7.5 Hz, 1H), 7.67 (d, J=8.0 Hz, 2H), 7.52 (t, J=7.3 Hz, 1H), 7.37 (d, J=8.1 Hz, 1H), 7.23 (t, J=7.1 Hz, 1H), 6.85 (d, J=8.1 Hz, 2H), 6.57 (d, J=4.9 Hz, 2H), 6.52 (s, 1H), 4.33-4.23 (m, 4H), 4.00 (s, 2H), 3.75 (s, 4H), 3.60 (d, J=5.3 Hz, 2H), 3.51 (d, J=5.3 Hz, 2H), 2.70 (s, 2H), 1.95 (s, 6H); $^{13}$C NMR (101 MHz, CDCl$_3$) δ 178.3, 165.8, 163.5, 161.6, 160.2, 156.2, 149.4, 133.6, 128.0, 125.6, 125.1, 124.2, 123.8, 123.5, 117.7, 115.1, 109.5, 105.9, 104.2, 83.5, 70.2, 69.5, 67.5, 60.1, 53.9, 11.2; LRMS (ESI) m/z 732 (M$^+$+H, 100), 754 (M$^+$+Na, 23); HRMS (ESI) calcd for $C_{37}H_{35}F_6N_3O_6$(M$^+$+H) 732.2436, Found 732.2421.

The detailed chemical synthesis of flavonoid monomer FM09i is described as shown in the scheme 27.

Scheme 27

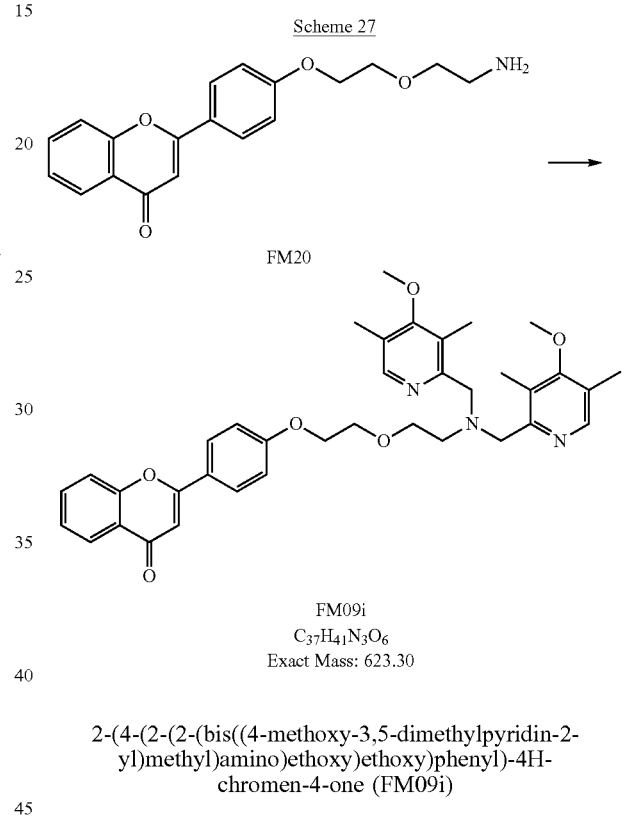

FM09i
$C_{37}H_{41}N_3O_6$
Exact Mass: 623.30

2-(4-(2-(2-(bis((4-methoxy-3,5-dimethylpyridin-2-yl)methyl)amino)ethoxy)ethoxy)phenyl)-4H-chromen-4-one (FM09i)

To a well stirred mixture of FM20 (0.15 g, 0.46 mmol), 2-(chloromethyl)-4-methoxy-3,5-dimethylpyridine hydrochloride (0.29 g, 1.3 mmol) and $K_2CO_3$ (0.20 g, 1.4 mmol) in ACN (20 mL), was heated to reflux for 4 h. After that, the reaction mixture was filtered and the obtained filtrate was evaporated under reduced pressure to give brown oil which was subjected to flash chromatography on silica gel with gradient elution (20% acetone in DCM to 70% acetone in DCM) to furnish FM09i (0.16 g, 0.25 mmol) in 51% yield: $^1$H NMR (400 MHz, CDCl$_3$) δ 8.23 (dd, J=7.9, 1.3 Hz, 1H), 8.16 (s, 2H), 7.86 (d, J=8.9 Hz, 2H), 7.72-7.67 (m, 1H), 7.56 (d, J=8.3 Hz, 1H), 7.42 (t, J=7.5 Hz, 1H), 7.02 (d, J=8.9 Hz, 2H), 6.74 (s, 1H), 4.16-4.12 (m, 2H), 3.81 (s, 3H), 3.73 (t, J=4.7 Hz, 3H), 3.70 (s, 5H), 3.62 (t, J=5.6 Hz, 2H), 2.81 (t, J=5.6 Hz, 2H), 2.22 (s, 6H), 2.10 (s, 6H); $^{13}$C NMR (101 MHz, CDCl$_3$) δ 178.3, 165.4, 163.5, 161.6, 158.2, 156.2, 148.0, 133.6, 128.0, 125.6, 125.1, 124.2, 123.8, 117.7, 115.1, 112.5, 106.2, 105.9, 69.0, 68.4, 67.8, 60.8, 60.3, 54.0, 15.2, 12.1; LRMS (ESI) m/z 624 (M$^+$+H, 100), 646 (M$^+$+Na, 7); HRMS (ESI) calcd for $C_{37}H_{41}N_3O_6$ (M$^+$+H) 624.3082, Found 624.3086.

The detailed chemical synthesis of flavonoid monomer FM09k is described as shown in the scheme 28.

Scheme 28

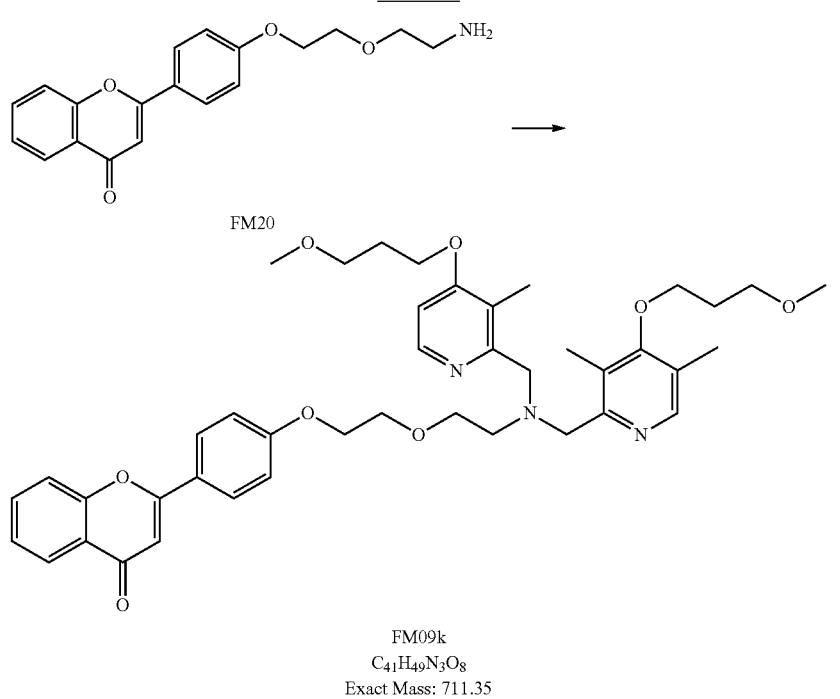

2-(4-(2-(2-(bis((4-(3-methoxypropoxy)-3-methyl pyridin-2-yl)methyl)amino)ethoxy)ethoxy) phenyl)-4H-chromen-4-one (FM09k)

To a well stirred mixture of FM20 (0.15 g, 0.46 mmol), 2-(chloromethyl)-4-(3-methoxypropoxy)-3-methylpyridine hydrochloride (0.35 g, 1.3 mmol) and $K_2CO_3$ (0.20 g, 1.4 mmol) in ACN (20 mL), was heated to reflux for 4 h. After that, the reaction mixture was filtered and the obtained filtrate was evaporated under reduced pressure to give brown oil which was subjected to flash chromatography on silica gel with gradient elution (20% acetone in DCM to 70% acetone in DCM) to furnish FM09k (0.18 g, 0.25 mmol) in 51% yield: $^1$H NMR (400 MHz, CDCl$_3$) δ 8.19 (d, J=4.5 Hz, 2H), 8.02 (d, J=7.6 Hz, 1H), 7.67 (d, J=8.0 Hz, 2H), 7.52 (t, J=7.5 Hz, 1H), 7.37 (d, J=8.1 Hz, 1H), 7.23 (t, J=7.1 Hz, 1H), 6.85 (d, J=8.1 Hz, 2H), 6.57 (d, J=4.9 Hz, 2H), 6.52 (s, 1H), 4.09-4.05 (m, 6H), 3.93 (s, 4H), 3.74-3.70 (m, 2H), 3.65 (t, J=6.2 Hz, 2H), 3.37-3.33 (m, 4H), 3.26 (s, 6H), 2.86 (t, J=6.2 Hz, 2H), 2.14-2.07 (m, 10H); $^{13}$C NMR (101 MHz, CDCl$_3$) δ 178.3, 166.4, 163.5, 161.6, 160.8, 156.2, 147.2, 133.6, 128.0, 125.6, 125.1, 124.2, 123.8, 117.7, 115.1, 113.5, 104.7, 105.9, 72.9, 70.1, 69.5, 66.6, 66.3, 60.2, 59.3, 53.0, 30.2, 11.1; m/z 712 (M$^+$+H, 100), 734 (M$^+$+Na, 15); HRMS (ESI) calcd for $C_{41}H_{49}N_3O_8$ (M++H) 712.3562, Found 712.3557.

The detailed chemical synthesis of flavonoid monomer FM09l is described as shown in the scheme 29.

Scheme 29

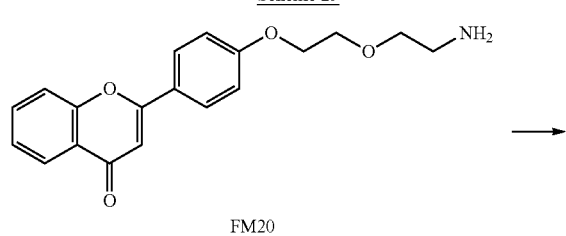

-continued

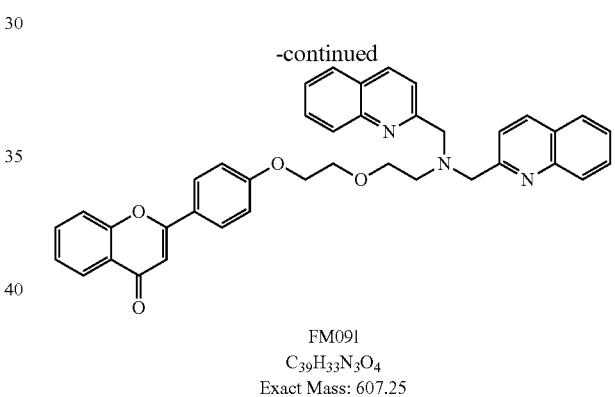

2-(4-(2-(2-(bis(quinolin-2-ylmethyl)amino)ethoxy) ethoxy)phenyl)-4H-chromen-4-one (FM09l)

To a well stirred mixture of FM20 (0.15 g, 0.46 mmol), 2-(chloromethyl)quinoline hydrochloride (0.28 g, 1.3 mmol) and $K_2CO_3$ (0.20 g, 1.4 mmol) in ACN (20 mL), was heated to reflux for 4 h. After that, the reaction mixture was filtered and the obtained filtrate was evaporated under reduced pressure to give brown oil which was subjected to flash chromatography on silica gel with gradient elution (20% acetone in DCM to 70% acetone in DCM) to furnish FM09l (0.15 g, 0.25 mmol) in 51% yield: $^1$H NMR (400 MHz, CDCl$_3$) δ 8.19 (d, J=7.9 Hz, 1H), 8.03 (t, J=9.3 Hz, 4H), 7.77-7.70 (m, 6H), 7.65-7.61 (m, 3H), 7.50-7.42 (m, 3H), 7.36 (t, J=7.5 Hz, 1H), 6.92 (d, J=8.6 Hz, 2H), 6.67 (s, 1H), 4.11 (s, 3H), 3.76-3.69 (m, 2H), 2.93 (t, J=5.5 Hz, 1H); $^{13}$C NMR (101 MHz, CDCl$_3$) δ 178.4, 163.3, 161.6, 156.1, 155.8, 147.2, 134.8, 133.6, 129.5, 128.7, 128.0, 127.8, 126.3, 125.9, 125.6, 125.1, 124.1, 123.9, 122.5, 118.0, 115.1, 106.2, 69.9, 69.3, 68.0, 60.9, 53.6; LRMS (ESI) m/z 608 (M⁺+H, 100), 630 (M⁺+Na, 13); HRMS (ESI) calcd for C₃₉H₃₃N₃O₄ (M⁺+H) 608.2509, Found 608.2518.

The detailed chemical synthesis of flavonoid monomer FM09m is described as shown in the scheme 30.

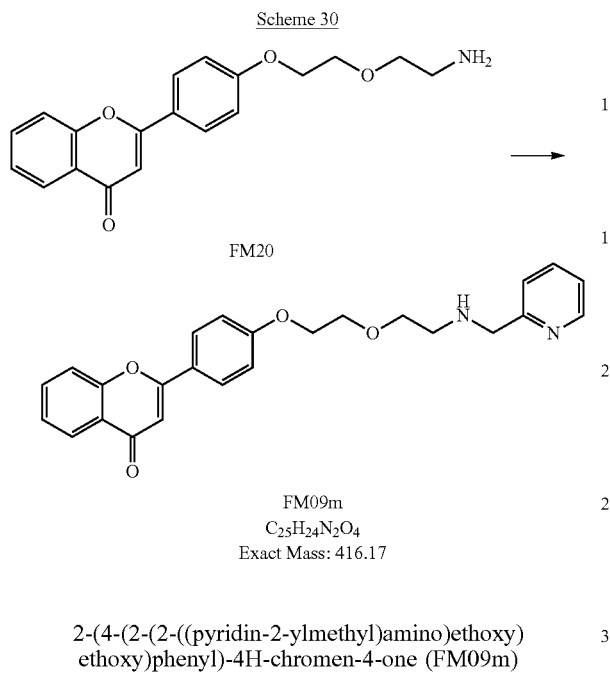

2-(4-(2-(2-((pyridin-2-ylmethyl)amino)ethoxy)ethoxy)phenyl)-4H-chromen-4-one (FM09m)

To a well stirred mixture of FM20 (0.32 g, 1 mmol), 2-(chloromethyl)pyridine hydrochloride (0.21 g, 1.3 mmol) and K₂CO₃ (0.10 g, 0.46 mmol) in ACN (20 mL), was heated to reflux for 4 h. After that, the reaction mixture was filtered and the obtained filtrate was evaporated under reduced pressure to give brown oil which was subjected to flash chromatography on silica gel with gradient elution (20% acetone in DCM to 70% acetone in DCM) to furnish FM09m (0.15 g, 0.37 mmol) in 75% yield: ¹H NMR (400 MHz, CDCl₃) δ 8.56 (d, J=4.3 Hz, 1H), 8.25 (dd, J=7.9, 1.4 Hz, 1H), 7.90 (d, J=8.9 Hz, 2H), 7.74-7.68 (m, 1H), 7.65 (td, J=7.7, 1.7 Hz, 1H), 7.58 (d, J=8.3 Hz, 1H), 7.46-7.41 (m, 1H), 7.33 (d, J=7.8 Hz, 1H), 7.18 (dd, J=6.9, 5.3 Hz, 1H), 7.07 (d, J=8.9 Hz, 2H), 6.77 (s, 1H), 4.26-4.22 (m, 2H), 3.98 (s, 2H), 3.91-3.87 (m, 2H), 3.75 (t, J=5.2 Hz, 2H), 2.93 (t, J=5.2 Hz, 2H); ¹³C NMR (101 MHz, CDCl₃) δ 178.3, 162.7, 161.7, 158.8, 155.6, 149.3, 136.4, 133.6, 127.6, 124.9, 124.5, 124.0, 123.9, 123.1, 121.9, 118.3, 115.7, 106.5, 70.8, 69.5, 68.1, 61.4, 54.0; LRMS (ESI) m/z 417 (M++H, 100), 439 (M⁺+Na, 9); HRMS (ESI) calcd for C₂₅H₂₅N₂O₄ (M⁺+H) 417.1814, Found 417.1813.

The detailed chemical synthesis of flavonoid monomer FM09p is described as shown in the scheme 31.

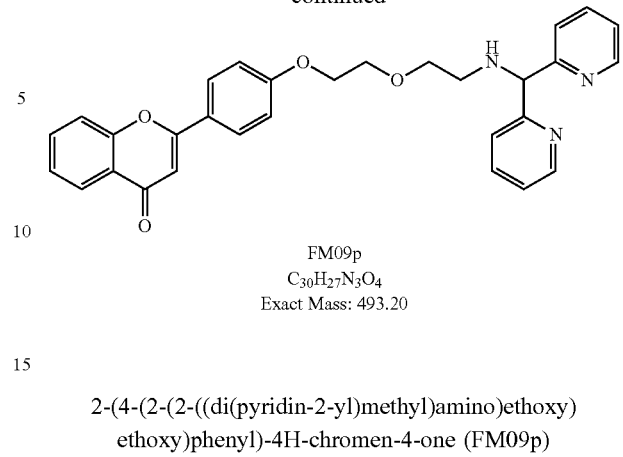

2-(4-(2-(2-((di(pyridin-2-yl)methyl)amino)ethoxy)ethoxy)phenyl)-4H-chromen-4-one (FM09p)

To a well stirred mixture of FM20 (0.15 g, 0.46 mmol) and MgSO₄ (0.20 g, 1.4 mmol) in dry dichloromethane (5 mL) in ice bath, under N₂ protection, di(pyridin-2-yl)methanone (0.08 g, 0.46 mmol) solubilized in dry dichloromethane (3 mL) was added dropwise. The reaction mixture was left under room temperature overnight. After that, sodium borohydride (0.03g, 0.79 mmol) solubilized in methanol was added dropwise to the reaction mixture in ice bath. The reaction mixture was left under room temperature overnight. Then the reaction mixture was filtered and the obtained filtrate was evaporated under reduced pressure to give brown oil which was subjected to flash chromatography on silica gel with gradient elution (20% acetone in DCM to 70% acetone in DCM) to furnish FM09p (0.17 g, 0.35 mmol) in 73% yield: ¹H NMR (400 MHz, CDCl₃) δ 8.55 (d, J=4.2 Hz, 2H), 8.22 (dd, J=7.9, 1.5 Hz, 1H), 7.87 (d, J=8.9 Hz, 2H), 7.71-7.62 (m, 3H), 7.54 (d, J=8.2 Hz, 1H), 7.44-7.37 (m, 3H), 7.19 (dd, J=6.7, 5.0 Hz, 2H), 7.06 (d, J=8.9 Hz, 2H), 6.74 (s, 1H), 5.50 (s, 1H), 4.28-4.20 (m, 2H), 3.92-3.87 (m, 2H), 3.86-3.82 (m, 2H), 3.08 (t, J=5.0 Hz, 2H); ¹³C NMR (101 MHz, CDCl₃) δ178.2, 163.1, 162.7, 159.1, 156.2, 149.0, 136.4, 132.8, 127.9, 125.6, 125.3, 124.7, 123.9, 123.0, 121.9, 118.0, 115.1, 106.2, 70.2, 68.7, 67.3, 64.8, 52.5; LRMS (ESI) m/z 494 (M⁺+H, 100), 516 (M⁺+Na, 22); HRMS (ESI) calcd for C₃₀H₂₇N₃O₄ (M⁺+H) 494.2064, Found 494.2071.

The detailed chemical synthesis of flavonoid monomer FM09am is described as shown in the scheme 32.

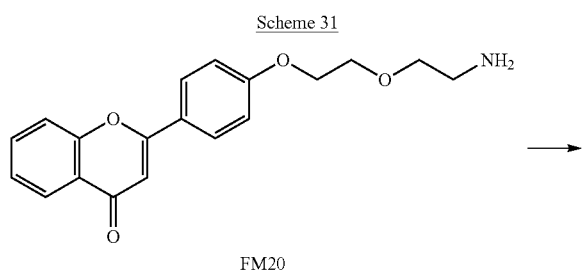

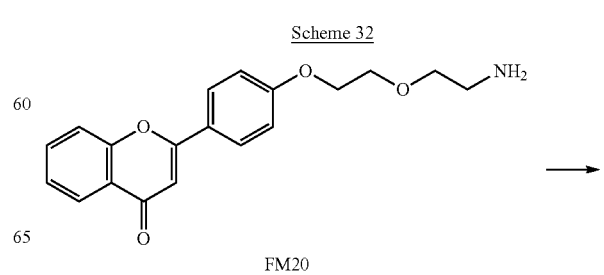

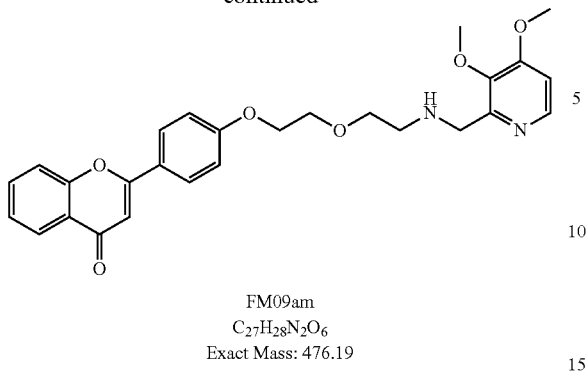

FM09am
$C_{27}H_{28}N_2O_6$
Exact Mass: 476.19

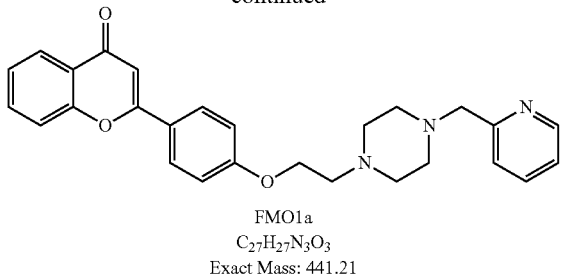

FM01a
$C_{27}H_{27}N_3O_3$
Exact Mass: 441.21

2-(4-(2-(2-(((3,4-dimethoxypyridin-2-yl)methyl)amino)ethoxy)ethoxy)phenyl)-4H-chromen-4-one (FM09am)

To a well stirred mixture of FM20 (0.32 g, 1 mmol), 2-(chloromethyl)-3,4-dimethoxypyridine hydrochloride (0.10 g, 0.46 mmol) and $K_2CO_3$ (0.20 g, 1.4 mmol) in ACN (20 mL), was heated to reflux for 4 h. After that, the reaction mixture was filtered and the obtained filtrate was evaporated under reduced pressure to give brown oil which was subjected to flash chromatography on silica gel with gradient elution (20% acetone in DCM to 70% acetone in DCM) to furnish FM09am (0.12 g, 0.25 mmol) in 50% yield: $^1$H NMR (400 MHz, CDCl$_3$) δ 8.21 (dd, J=7.9, 1.5 Hz, 1H), 8.13 (d, J=5.5 Hz, 1H), 7.85 (d, J=8.9 Hz, 2H), 7.67 (ddd, J=8.6, 7.2, 1.5 Hz, 1H), 7.54 (d, J=8.2 Hz, 1H), 7.43-7.36 (m, 1H), 7.03 (d, J=8.9 Hz, 2H), 6.76 (d, J=5.5 Hz, 1H), 6.72 (s, 1H), 4.23-4.19 (m, 2H), 4.11 (s, 2H), 3.89-3.87 (m, 5H), 3.84 (s, 3H), 3.83-3.78 (m, 2H), 3.05 (t, J=5.2 Hz, 2H); $^{13}$C NMR (101 MHz, CDCl$_3$) δ 178.3, 163.3, 161.7, 159.9, 158.4, 156.2, 140.4, 133.6, 127.8, 125.6, 125.1, 124.3, 123.9, 123.5, 118.2, 115.1, 106.5, 105.2, 69.9, 69.3, 67.7, 60.9, 60.6, 56.5, 53.7; LRMS (ESI) m/z 477 (M$^+$+H, 100), 499 (M$^+$+Na, 20); HRMS (ESI) calcd for $C_{27}H_{28}N_2O_6$ (M$^+$+H) 477.1938, Found 477.1932.

The detailed chemical synthesis of flavonoid monomer FM01a is described as shown in the scheme 33.

Scheme 33.

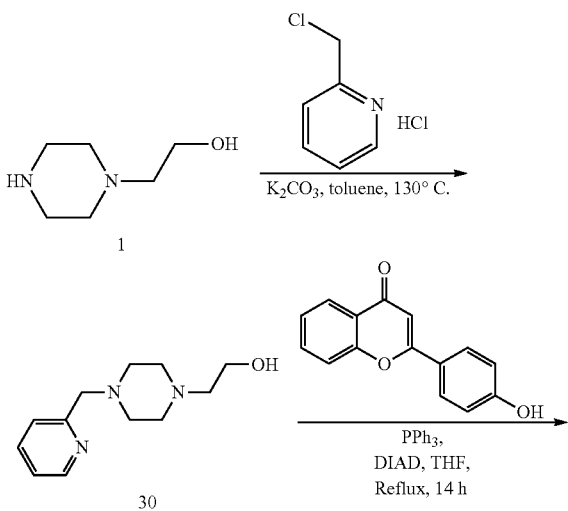

2-(4-(2-(4-(pyridin-2-ylmethyl)piperazin-1-yl)ethoxy)phenyl)-4H-chromen-4-one (FM01a)

A well stirred mixture of hydroxylamine 1 (4.6 g, 35 mmol), 2-chloromethylpyridine hydrochloride (5.9 g, 36 mmol) and $K_2CO_3$ (10 g) in toluene (80 mL) was heated to reflux for 14 h. The reaction mixture was then filtered to remove excess $K_2CO_3$. The obtained filtrate was evaporated under reduced pressure to give oily crude mixture which was subjected vacuum distillation to furnish alcohol 30 (2.4 g) in 32% yield. $^1$H NMR (400 MHz, CDCl$_3$) δ 8.46 (d, J=1.5 Hz, 1H), 8.43 (dd, J=4.8, 1.4 Hz, 1H), 7.61 (d, J=7.8 Hz, 1H), 7.20 (dd, J=7.7, 4.9 Hz, 1H), 3.57 (t, J=5.5 Hz, 2H), 3.46 (s, 2H), 3.34 (s, 1H), 2.52-2.44 (m, 10H); $^{13}$C NMR (101 MHz, CDCl$_3$) δ 155.9. 145.3, 137.6, 122.1, 119.9, 60.4, 59.3, 57.5, 53.0, 52.6. Alcohol 30 was used for the next step without further purification. To a well stirred mixture of alcohol 30 (0.45 g, 2.0 mmol), 4'-hydroxyflavone (0.49 g, 2.0 mmol) and PPh$_3$ (0.56 g, 2.1 mmol) in THF (20 mL) was added diisopropyl azodicarboxylate (DIAD) (0.43 g, 2.1 mmol) dropwise. The reaction mixture was further heated to reflux for 12 h. The reaction mixture was evaporated under reduced pressure to give brown oil which was subjected to flash column chromatography on silica gel with gradient elution (20% acetone in DCM to 80% acetone to DCM) to furnish the desired product FM01a (0.33 g, 0.74 mmol) in 37% yield: 1H NMR (400 MHz, CDCl3) δ 8.54 (d, J=3.6 Hz, 1H), 8.20 (dd, J=7.9, 1.5 Hz, 1H), 7.85 (d, J=8.9 Hz, 2H), 7.69-7.60 (m, 2H), 7.53 (d, J=8.3 Hz, 1H), 7.42-7.35 (m, 2H), 7.15 (dd, J=6.8, 5.5 Hz, 1H), 7.00 (d, J=8.9 Hz, 2H), 6.72 (s, 1H), 4.17 (t, J=5.8 Hz, 2H), 3.67 (s, 3H), 2.85 (t, J=5.8 Hz, 2H), 2.68 (s, 4H), 2.61 (s, 5H); $^{13}$C NMR (101 MHz, CDCl$_3$) δ 178.3, 163.3, 161.7, 157.5, 156.2, 148.0, 137.4, 133.6, 128.0, 125.4, 125.1, 124.2, 123.9, 122.0, 120.9, 118.0, 115.1, 106.2, 66.1, 61.9, 56.8, 53.3, 53.0; m/z 442 (M$^+$+H, 100), 464 (M$^+$+Na, 8); HRMS (ESI) calcd for $C_{27}H_{28}N_3O_3$ (M$^+$+H) 442.2131, Found 442.2135.

The detailed chemical synthesis of flavonoid monomer FM01b is described as shown in the scheme 34.

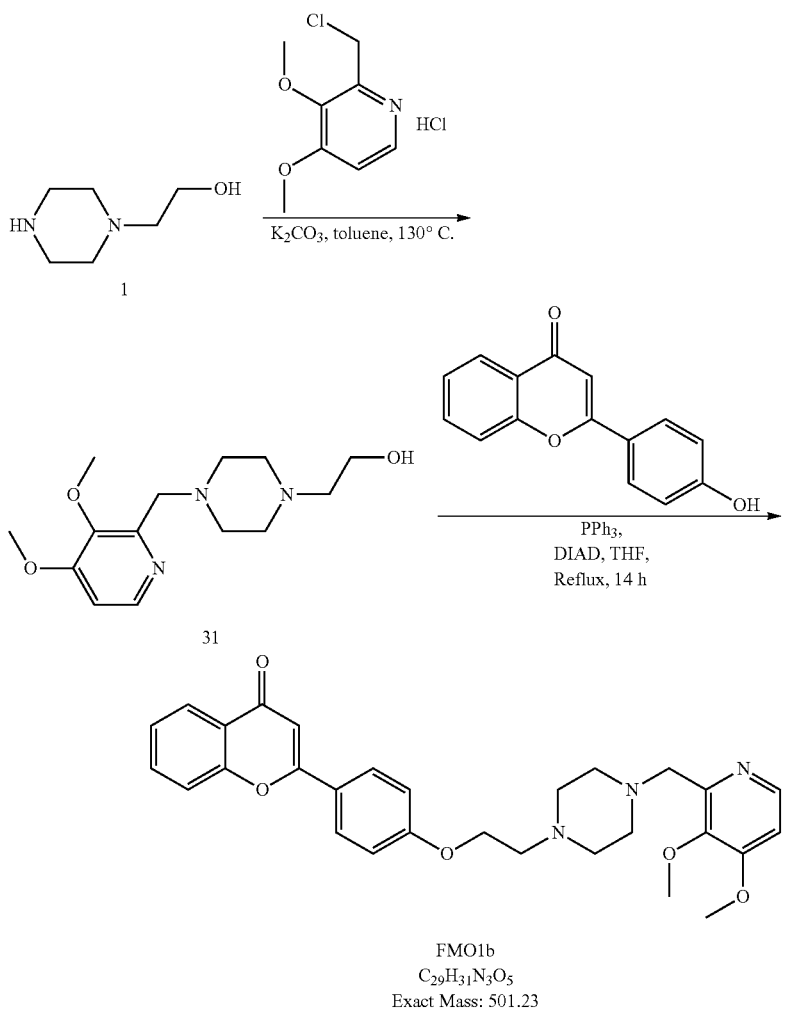

2-(4-(2-(4-((3,4-dimethoxypyridin-2-yl)methyl)piperazin-1-yl)ethoxy)phenyl)-4H-chromen-4-one (FM01b)

A well stirred mixture of hydroxylamine 1 (4.6 g, 35 mmol), 2-(chloromethyl)-3,4-dimethoxypyridine hydrochloride (8.1 g, 36 mmol) and $K_2CO_3$ (10 g) in toluene (80 mL) was heated to reflux for 14 h. The reaction mixture was then filtered to remove excess $K_2CO_3$. The obtained filtrate was evaporated under reduced pressure to give oily crude mixture which was subjected vacuum distillation to furnish alcohol 31 (3.9 g) in 51% yield. $^1$H NMR (400 MHz, CDCl$_3$) δ 7.24 (d, J=5.6 Hz, 1H), 6.60 (t, J=5.6 Hz, 1H), 3.90 (s, 3H), 3.85 (s, 3H), 3.72 (s, 2H), 3.42 (t, J=5.7 Hz, 2H), 2.85 (t, J=5.7 Hz, 2H), 2.67 (s, 6H), 2.56 (s, 3H); $^{13}$C NMR (101 MHz, CDCl$_3$) δ 158.7, 147.6, 140.2, 123.8, 106.4, 68.2, 64.8, 61.4, 59.4, 57.8, 55.2, 52.9. Alcohol 31 was used for the next step without further purification. To a well stirred mixture of alcohol 31 (0.56 g, 2.0 mmol), 4'-hydroxyflavone (0.49 g, 2.0 mmol) and PPh$_3$ (0.56 g, 2.1 mmol) in THF (20 mL) was added diisopropyl azodicarboxylate (DIAD) (0.43 g, 2.1 mmol) dropwise. The reaction mixture was further heated to reflux for 12 h. The reaction mixture was evaporated under reduced pressure to give brown oil which was subjected to flash column chromatography on silica gel with gradient elution (20% acetone in DCM to 80% acetone to DCM) to furnish the desired product FM01b (0.39 g, 0.79 mmol) in 38% yield: $^1$H NMR (400 MHz, CDCl$_3$) δ 8.22 (t, J=7.1 Hz, 2H), 7.86 (d, J=8.8 Hz, 2H), 7.70-7.65 (m, 1H), 7.54 (d, J=8.3 Hz, 1H), 7.40 (t, J=7.5 Hz, 1H), 7.00 (d, J=8.8 Hz, 2H), 6.77 (d, J=5.5 Hz, 1H), 6.73 (s, 1H), 4.18 (t, J=5.7 Hz, 2H), 3.90 (s, 3H), 3.85 (s, 3H), 3.72 (s, 2H), 2.85 (t, J=5.7 Hz, 2H), 2.67 (s, 6H), 2.56 (s, 3H); $^{13}$C NMR (101 MHz, CDCl$_3$) δ 178.2, 163.4, 161.6, 158.5, 156.2, 145.0, 143.4, 133.6, 128.0, 125.3, 125.1, 124.2, 123.9, 123.0, 118.5, 115.1, 106.9, 106.3, 66.2, 61.8, 59.4, 57.4, 56.8, 53.2, 52.9; LRMS (ESI) m/z 502 (M$^+$+H, 100), 524 (M$^+$+Na, 18); HRMS (ESI) calcd for $C_{29}H_{31}N_3O_5$ (M$^+$+H) 502.2326, Found 502.2321.

The detailed chemical synthesis of flavonoid monomer FM05a is described as shown in the scheme 35.

Scheme 35.

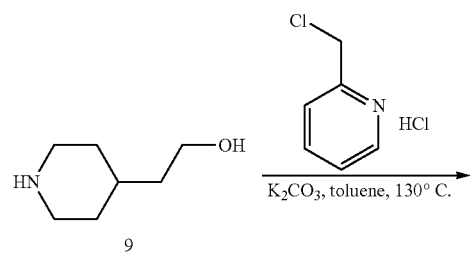

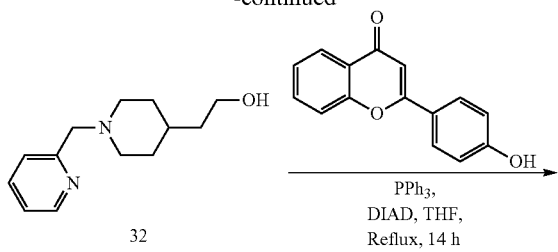

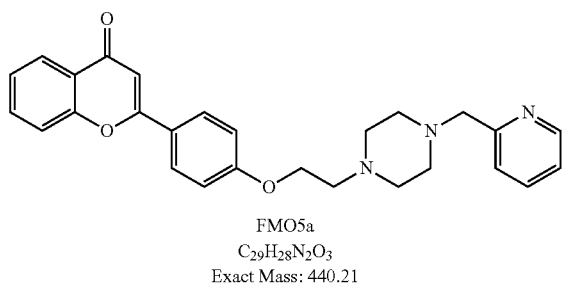

FM05a
C29H28N2O3
Exact Mass: 440.21

2-(4-(2-(1-(pyridin-2-ylmethyl)piperidin-4-yl)ethoxy)phenyl)-4H-chromen-4-one (FM05a)

A well stirred mixture of hydroxylamine 9 (2.6 g, 20 mmol), 2-chloromethylpyridine hydrochloride (3.6 g, 22 mmol) and K₂CO₃ (3.2 g) in toluene (60 mL) was heated to reflux for 14 h. The reaction mixture was then filtered to remove excess K₂CO₃. The obtained filtrate was evaporated under reduced pressure to give oily crude mixture which was subjected to vacuum distillation to furnish alcohol 32 (1.9 g) in 44% yield: ¹H NMR (400 MHz, CDCl₃) 8.44 (d, J=1.5 Hz, 1H), 8.41 (dd, J=4.8, 1.4 Hz, 1H), 7.58 (d, J=7.8 Hz, 1H), 7.16 (dd, J=7.7, 4.9 Hz, 1H), 3.23 (s, 2H), 2.79 (s, 1H), 1.93 (t, J=11.5 Hz, 2H), 1.67-1.49 (m, 4H), 1.35-1.12 (m, 7H); ¹³C NMR (101 MHz, CDCl₃) δ 158.5, 145.4, 144.7, 122.3, 106.1, 66.1, 61.1, 54.0, 38.6, 32.6, 32.2. Alcohol 32 was used for the next step without further purification. To a well stirred mixture of alcohol 32 (0.54 g, 2.5 mmol), 4'-hydroxyflavone (0.60 g, 2.5 mmol) and PPh₃ (0.71 g, 2.7 mmol) in THF (20 mL), was added DIAD (0.55 g, 2.7 mmol) dropwise. The reaction mixture was further heated to reflux for 12 h. The reaction mixture was evaporated under reduced pressure to give brown oil which was subjected to flash column chromatography on silica gel with gradient elution (20% acetone in DCM to 80% acetone to DCM) to furnish the desired product FM05a (0.40 g) in 38% yield: ¹H NMR (400 MHz, CDCl₃) δ 8.53-8.49 (m, 1H), 8.19-8.15 (m, 1H), 7.82 (d, J=8.8 Hz, 1H), 7.65-7.57 (m, 2H), 7.50 (d, J=8.3 Hz, 1H), 7.36 (dd, J=16.2, 8.1 Hz, 2H), 7.12 (dd, J=7.1, 3.9 Hz, 1H), 6.95 (d, J=8.8 Hz, 1H), 6.69 (s, 1H), 4.03 (t, J=6.4 Hz, 1H), 3.62 (d, J=7.1 Hz, 2H), 3.52 (t, J=6.9 Hz, 1H), 2.88 (t, J=11.3 Hz, 2H), 2.15-1.98 (m, 3H), 1.77-1.59 (m, 5H), 1.44-1.18 (m, 3H); ¹³C NMR (101 MHz, CDCl₃) δ 178.4, 163.5, 161.9, 158.6, 156.2, 145.6, 144.5, 133.5, 127.9, 125.6, 125.0, 123.9, 123.8, 122.0, 117.9, 114.9, 106.5, 106.1, 66.1, 61.1, 54.0, 35.6, 32.6, 32.2; LRMS (ESI) m/z 441 (M⁺+H, 100), 463 (M⁺+Na, 16); HRMS (ESI) calcd for C₂₈H₂₉N₂O₃ (M⁺+H) 441.2178, Found 441.2175.

The detailed chemical synthesis of flavonoid monomer FM05b is described as shown in the scheme 36.

Scheme 36.

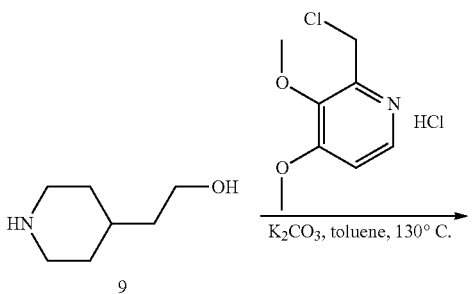

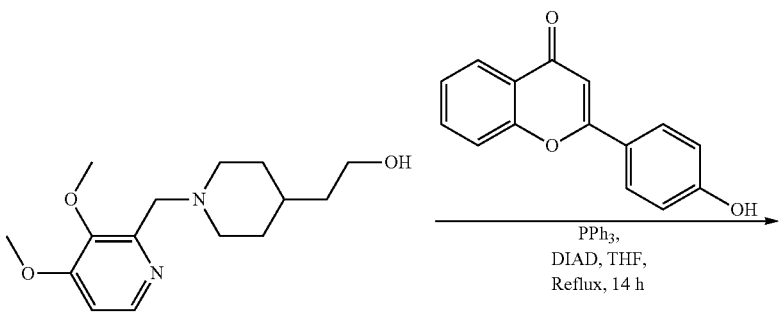

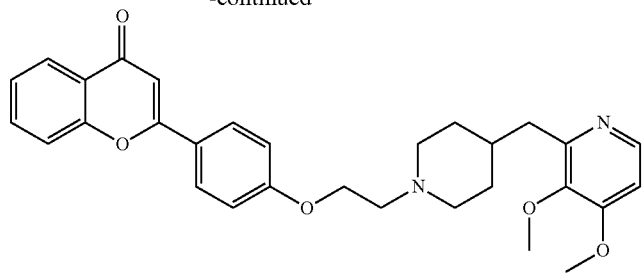

FM05b
C$_{30}$H$_{32}$N$_2$O$_5$
Exact Mass: 500.23

2-(4-(2-(1-((3,4-dimethoxypyridin-2-yl)methyl)piperidin-4-yl)ethoxy)phenyl)-4H-chromen-4-one (FM05b)

A well stirred mixture of hydroxylamine 9 (2.6 g, 20 mmol), 2-(chloromethyl)-3,4-dimethoxypyridine hydrochloride (4.9 g, 22 mmol) and K$_2$CO$_3$ (3.2 g) in toluene (60 mL) was heated to reflux for 14 h. The reaction mixture was then filtered to remove excess K$_2$CO$_3$. The obtained filtrate was evaporated under reduced pressure to give oily crude mixture which was subjected to vacuum distillation to furnish alcohol 33 (1.5 g) in 35% yield: $^1$H NMR (400 MHz, CDCl$_3$) δ7.24 (d, J=5.6 Hz, 1H), 6.60 (t, J=5.6 Hz, 1H), 3.96 (s, 3H), 3.90 (s, 3H), 3.53 (s, 2H), 2.87 (s, 1H), 1.96 (t, J=11.8 Hz, 2H), 1.69-1.54 (m, 4H), 1.38-1.11 (m, 7H); $^{13}$C NMR (101 MHz, CDCl$_3$) δ157.7, 148.6, 143.2, 120.8, 104.4, 67.2, 58.9, 53.7, 36.1, 33.2, 31.8. Alcohol 33 was used for the next step without further purification. To a well stirred mixture of alcohol 33 (0.70 g, 2.5 mmol), 4'-hydroxyflavone (0.60 g, 2.5 mmol) and PPh$_3$ (0.71 g, 2.7 mmol) in THF (20 mL), was added DIAD (0.55 g, 2.7 mmol) dropwise. The reaction mixture was further heated to reflux for 12 h. The reaction mixture was evaporated under reduced pressure to give brown oil which was subjected to flash column chromatography on silica gel with gradient elution (20% acetone in DCM to 80% acetone to DCM) to furnish the desired product FM05b (0.50 g) in 46% yield: $^1$H NMR (400 MHz, CDCl$_3$) δ 8.26 (d, J=5.5 Hz, 1H), 8.24 (dd, J=8.0, 1.3 Hz, 1H), 7.89 (d, J=8.8 Hz, 2H), 7.74-7.66 (m, 1H), 7.57 (d, J=8.3 Hz, 1H), 7.42 (t, J=7.5 Hz, 1H), 7.01 (d, J=8.9 Hz, 2H), 6.78 (d, J=5.5 Hz, 1H), 6.76 (s, 1H), 4.08 (t, J=6.5 Hz, 2H), 3.92 (s, 3H), 3.87 (s, 3H), 3.68 (s, 2H), 2.99 (d, J=11.4 Hz, 2H), 2.13 (t, J=11.0 Hz, 2H), 1.75 (m, 4H), 1.61-1.50 (m, 1H), 1.46-1.34 (m, 2H); $^{13}$C NMR (101 MHz, CDCl$_3$) δ 178.4, 163.5, 161.9, 158.6, 156.2, 145.6, 144.5, 133.5, 127.9, 125.6, 125.0, 123.9, 123.8, 122.0, 117.9, 114.9, 106.5, 106.1, 66.1, 61.1, 58.7, 55.6, 54.0, 35.6, 32.6, 32.2; LRMS (ESI) m/z 501 (M$^+$+H, 100), 523 (M$^+$+Na, 12); HRMS (ESI) calcd for C$_{30}$H$_{32}$N$_2$O$_5$ (M++H) 501.2331, Found 501.2339.

Results

Biological Activities of Amine-Containing Flavonoid Monomers

Anti-Promastigotes Activities

IC$_{50}$ values of known antileishmanials and the amine-containing flavonoid monomers of the present invention to promastigotes (*L. amazonensis* LV78, *L. major* FV1, *L. donovani* HU3, *L. donovani* 39), macrophages (Raw 264.7 and PEM) and mouse fibroblast (L929) were determined.

The anti-promastigotes activities and cytotoxicity of the amine-containing flavonoid monomers of the invention are shown in Table 1.

Many amine-containing flavonoid monomers have IC$_{50}$ less than 5 μM, including FM01, FM02, FM04, FM05, FM06, FM08, FM09, FM13, FM14, FM15, FM17 and FM18. These monomers showed relatively low to moderate cytotoxicity towards L929 fibroblasts (IC$_{50}$ ranged from >11 to >100 μM), RAW264.7 cells (IC$_{50}$ ranged from 15.1 to >100 μM) and PEM (22 to 55.9 μM).

Anti-Amastigotes Activities

PEM cells were infected with late-log promastigotes (*L. amazonensis* LV78, *L. braziliensis* UA847, *L. donovani* HU3, *L. donovani* 39) for 24 hr at 37° C. Infected macrophages were then treated with various antileishmanials and incubated for 3 days at 37° C. After 3 days, the cover slips were stained with Giemsa. The number of amastigotes per 100 macrophages were determined and used to calculate IC$_{50}$ values.

The anti-amastigotes activities of the compounds of the invention are shown in Table 2. Many amine-containing flavonoid monomers have IC$_{50}$ less than 5 μM, including FM01, FM02, FM04, FM05, FM06, FM09, FM13, FM14, FM15, FM17, FM18 and FM19). With reference to Table 2, FM09 displayed the strongest anti-amastigote activity with IC$_{50}$ ranging from <0.37 to 0.6 μM towards both visceral and cutaneous *Leishmania* amastigotes.

Figure 5:
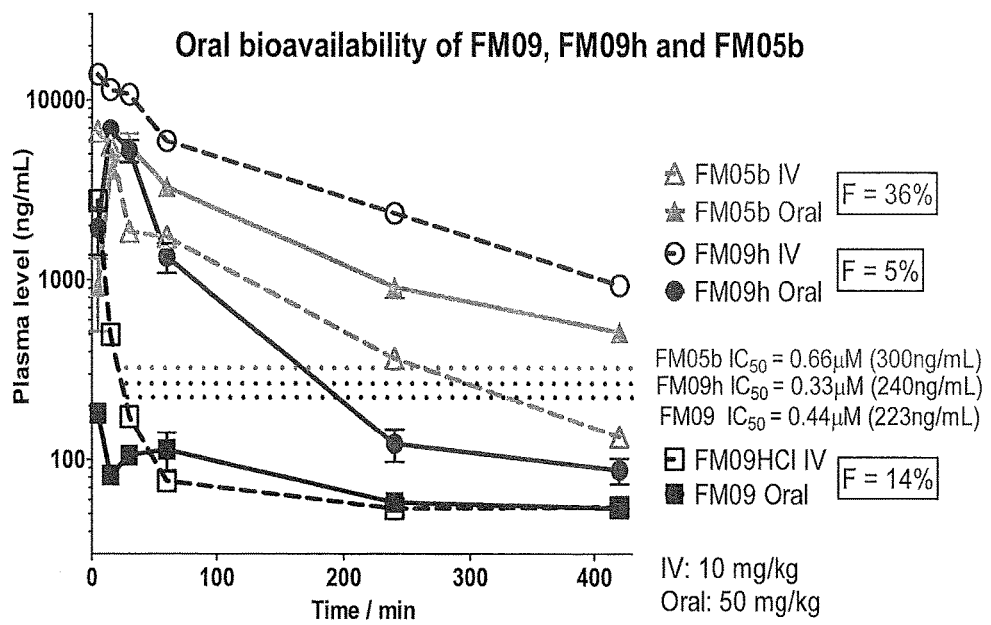
FIG. 5 shows a graph of the pharmacokinetics study of flavonoid FM09, FM09h and FM05b administered to Balb/c mice at either 10 mg/kg iv or 50 mg/kg oral (n=2 to 8). Animals were sacrificed at the indicated time point and plasma level of the corresponding flavonoids were determined using LC-MSMS. $IC_{50}$ of corresponding flavonoids are indicated. Bioavailability (F) was calculated by dividing the dose-adjusted area under curve (AUC) of that of orally-fed over intravenously administered animals.

Derivatives of FM09, FM01 and FM05 were synthesized and their anti-promastigote and anti-amastigote activity were determined (Table 3C). Many amine-containing flavonoid monomers have IC50 less than 5 μM, including FM09a, FM09b, FM09c, FM09e, FM09h, FM09i, FM09k, FM09l, FM01b and FM05b. Detailed pharmacokinetics study of FM09, FM09h and FM05b showed that the bioavailability is 14%, 5% and 36% respectively (Figure. 5). Plasma level of FM09h and FM05b remain at level higher than respective IC50 after 180 and 420 minutes post oral feeding respectively. Orally-fed FM09 is rapidly cleared in the plasma (FIG. 5). This result suggests that both FM05b and FM09h can be orally-fed to achieve therapeutic levels for treating leishmaniasis.

TABLE 1

Anti-promastigote activity and cytotoxicity of flavonoid monomers.

| | Anti-promastigote activity ($IC_{50}$, μM) | | | | Cytotoxicity ($IC_{50}$, μM) | | |
|---|---|---|---|---|---|---|---|
| | *L. amazon* LV78 | *L. major* FV1 | *L. donovani* HU3 | *L. donovani* Ld39 | L929 | RAW264.7 | PEM |
| 39 | | | 0.2 ± 0.03* | 0.21 ± 0.06 | 26.4 | >100 | >88.0 |
| FM01 | 6.0 ± 1.8 | 5.6 ± 1.0 | 1.2 ± 0.3 | 0.7 ± 0.1 | >33 | 51.8 ± 3.3 | ND |
| FM01.HCl | 12.6 ± 0.9 | 6.7 ± 1.9 | ND | 1.3 ± 0.3 | 33.7 | ND | 55.9 |
| FM02 | 4.6 ± 0.6 | 5.4 ± 1.0 | 1.8 ± 0.3 | 2.1 ± 0.6 | 22.1 ± 4.0 | 25.0 ± 1.8 | 22 |
| FM03 | >100 | >100 | 66.2 ± 11.0 | >100 | >100 | >100 | ND |
| FM04 | 2.8 ± 0.8 | 3.8 ± 0.7 | 2.4 ± 0.5 | 2.6 ± 0.5 | >33 | 15.1 ± 3.8 | 20.3 |
| FM04.HCl | ND | ND | ND | ND | ND | ND | ND |
| FM05 | 5.1 ± 1 | 3.9 ± 0.8 | 0.4 ± 0.1 | 0.3 ± 0.1 | >100 | 36.8 ± 4.4 | ND |
| FM05.HCl | 6.0 ± 0.5 | 3.5 ± 0.9 | ND | 1.2 ± 0.5 | ND | ND | 23.8 |
| FM06 | 2.0 ± 0.3 | 3.6 ± 0.7 | 2.2 ± 0.5 | 1.1 ± 0.1 | >33 | 16.8 ± 2.3 | ND |
| FM07 | >100 | >100 | 38.8 ± 6.9 | 21.4 ± 2.6 | 26.0 ± 4.1 | >75 | ND |
| FM08 | 8.3 ± 1.9 | 9.5 ± 1.2 | 1.4 ± 0.4 | 2.7 ± 0.9 | >33 | 49.5 ± 5.6 | ND |
| FM09 | 1.0 ± 0.3 | 0.8 ± 0.1 | 0.5 ± 0.2 | 0.5 ± 0.1 | >33 | 18.9 ± 2.2 | 22.0 |
| FM09.HCl | 0.7 0.2 | 1.2 ± 0.3 | 0.2 ± 0.1 | 0.5 ± 0.1 | 20.2 ± 8.4 | 35.0 ± 6.7 | ND |
| FM10 | 31.4 ± 2.4 | 78.5 ± 11.3 | 37.6 ± 2.8 | 49.5 ± 8.0 | >33 | 34.9 ± 1.9 | ND |
| FM11 | >100 | >100 | 66.9 ± 9.7 | >100 | >33 | 23.5 ± 2.7 | ND |
| FM12 | >100 | >100 | 25.4 ± 3.6 | 15.0 ± 2.2 | >100 | >100 | ND |
| FM13 | 3.5 ± 1.1 | 5.7 ± 3.1 | 1.1 ± 0.6 | 0.7 ± 0.2 | >100 | >100 | ND |
| FM14 | 1.4 ± 0.3 | 1.6 ± 0.6 | 0.3 ± 0.1 | 1.4 ± 0.9 | 10.6 ± 1.2 | 21.6 ± 1.9 | ND |
| FM15 | 4.8 ± 1.3 | 6.4 ± 1.7 | 1.5 ± 0.3 | 1.8 ± 0.7 | 14.9 ± 2.6 | 47 ± 2.7 | ND |
| FM16 | >100 | >100 | >50 | 87.1 ± 13.0 | >100 | >100 | ND |
| FM17 | 0.9 ± 0.3 | 2.1 ± 0.5 | 0.4 ± 0.1 | 1.5 ± 0.5 | >100 | >100 | ND |
| FM18 | 5.5 ± 1 | 4.9 ± 0.4 | 1.9 ± 0.4 | 2.7 ± 0.9 | 39.1 ± 2.5 | 52.6 ± 4.5 | ND |
| FM19 | 17.5 ± 3.2 | 21.6 ± 4.2 | 9.8 ± 2.5 | >100 | 55.1 ± 7.2 | >100 | ND |
| FM20 | 57.6 ± 37.3 | 59.8 ± 6.9 | ND | 34.9 ± 14.1 | 41.5 ± 15.6 | 15.8 | 57.5 ± 9.2 |
| FM21 | 47.8 ± 18.7 | 22.6 ± 10.9 | ND | 3.4 ± 0.9 | 24 | ND | 58.5 ± 4.3 |
| Pentamidine | 15.7 ± 5.2 | 17.8 ± 2.2 | ND | 5.3 ± 0.9 | ND | 30.0 ± 5.0 | 30.4 ± 11 |
| Amphotericin B | 0.24 ± 0.03 | 0.29 ± 0.05 | 0.2 | 0.095 ± 0.02 | ND | 12.0 ± 2.5 | 7.4 ± 0.4 |
| Miltefosine | 32.7 ± 26.9 | 9.7 ± 1.2 | 5.1 ± 1.4 | 17.3 ± 2.1 | ND | 20.0 ± 4.0 | 75.3 ± 9.4 |
| Paramomycin | ND | ND | ND | 24.5 ± 2.4 | ND | >100 | >100 |

$IC_{50}$ values were presented as mean ± standard error of mean.
N = 1-8 independent experiments.
PEM = peritoneal elicited macrophages.
ND = not determined.
*Another wild type *L. donovani* (LdAG83) was used to measure $IC_{50}$ instead of HU3.

TABLE 2

Anti-amastigote activity and cytotoxicity of flavonoid monomers.

| | Anti-amastigote activity ($IC_{50}$, μM) | | | |
|---|---|---|---|---|
| | *L. amazonensis* LV78 | *L. baziliensis* UA847 | *L. donovani* HU3 | *L. donovani* Ld39 |
| FM01 | 1.8 ± 0.6 | 8.4 | >9.0 | >10 |
| FM01.HCl | >9 | ND | ND | ND |
| FM02 | 4.7 ± 1.0 | ND | >10 | 9.6 |
| FM03 | >10 | >10 | >9 | >10 |
| FM04 | 3.7 ± 1.7 | ND | >5 | 6.8 |
| FM04.HCl | ND | ND | ND | ND |
| FM05 | 4.1 ± 0.9 | ND | 3.5 ± 0.7 | >10 |
| FM05.HCl | 6.9 ± 0.9 | ND | ND | ND |
| FM06 | 4.5 ± 1.8 | ND | >10 | >10 |
| FM07 | >10 | >10 | ND | >10 |
| FM08 | 6.7 ± 1.8 | ND | >10 | >10 |
| FM09 | 0.3 ± 0.1 | 0.6 ± 0.1 | 0.4 ± 0.1 | <0.37 |
| FM09.HCl | 0.4 | ND | 1.8 | ND |
| FM10 | 6.0 ± 0.2 | ND | ND | >10 |
| FM11 | 7.1 ± 1.6 | ND | ND | >10 |
| FM12 | >10 | ND | ND | >10 |
| FM13 | 2.5 ± 0.5 | ND | >10 | 3.3 |
| FM14 | 1.9 ± 0.5 | ND | >7 | 8.4 |
| FM15 | >9 | ND | >10 | 3.3 |
| FM16 | >10 | ND | ND | 5.7 |
| FM17 | 3.4 ± 0.9 | ND | >10 | >10 |
| FM18 | 3.1 ± 0.1 | ND | >9 | >10 |
| FM19 | 1.3 ± 0.6 | <0.37 | >10 | >10 |
| FM20 | ND | ND | ND | 0.7 ± 0.1 |

TABLE 2-continued

Anti-amastigote activity and cytotoxicity of flavonoid monomers.

| | Anti-amastigote activity ($IC_{50}$, μM) | | | |
|---|---|---|---|---|
| | L. amazonensis LV78 | L. baziliensis UA847 | L. donovani HU3 | L. donovani Ld39 |
| FM21 | 4.5 | ND | ND | 0.33 |
| SSG | 32.5 ± 17.6 | 35.6 ± 19.9 | ND | 675 ± 75 |
| Pentamidine | 15.7 ± 5.2 | 1.1 ± 0.1 | ND | >30 |
| Amphotericin B | 0.055 ± 0.029 | 0.049 ± 0.01 | ND | 0.062 |
| Miltefosine | 32.7 ± 26.9 | 13 ± 1.3 | ND | 16 ± 6.4 |
| Paromomycin | ND | ND | ND | 41 ± 1.1 |

The values were presented as mean ± standard error of mean.
N = 1-6 independent experiments.
ND = not determined.

Comparison with Compound 39, Monomeric Version of Compound 39 (FM21) and Other Anti-Leishmanial Agents Anti-amastigote activity against L. amazonensis (which causes cutaneous leishmaniasis) of some exemplary amine-containing flavonoid monomers are compared with compound 39 and 39 monomer (FM21) in Table 3A. L. amazonensis can cause cutaneous leishmaniasis. All these monomers are found to be highly potent, with anti-L. amazonensis amastigotes activities of $IC_{50}$ ranged 0.3-3.4 μM, which is comparable to that of 39 (0.43 μM). The most potent flavonoid monomer is FM09, with $IC_{50}$ of 0.3 μM and a selective index of 63. Other exemplary active flavonoid monomers include FM01, FM13, FM14, FM17, FM19 and FM21.

As visceral leishmaniasis (caused by Leishmania donovani) is the major cause of death among various types of leishmaniasis, activity against L. donovani amastigotes (HU3), and especially, SSG-resistant L. donovani (Ld39), would be highly desirable.

Anti-amastigote activity against L. donovani HU3 or Ld39 of some exemplary amine-containing flavonoid monomers are compared to 39 in Table 3B. FM09 is the most active flavonoid monomer ($IC_{50}$=0.4 μM and <0.37 μM against HU3 and Ld39 respectively, with selective index of 47.3. FM21 is also highly active against Ld39 ($IC_{50}$=0.33 μM with selective index of 177). FM05 is also active HU3 amastigotes ($IC_{50}$=3.5 μM with selection index of 10.5) whereas FM13 and 16 are active against Ld39 ($IC_{50}$=3.3, and 5.7 μM with selective index of >33 and >17.5 respectively).

In terms of toxicity to macrophages (Raw264.7 cell line and peritoneal elicited macrophages PEM), although not as safe as 39 ($IC_{50}$=>100 μM against both Raw264.7 cell line and PEM), the monomers of the invention are found to be non-toxic to Raw264.7 cell line ($IC_{50}$=19->100 μM) (Table 3A and 3B). In terms of toxicity to L929 fibroblasts, they are less toxic ($IC_{50}$>33 to >100 μM) than 39 ($IC_{50}$=26.4 μM), except for FM14 ($IC_{50}$=10.6 μM) (Table 1). In terms of toxicity to PEM cells, FM09 is found to be quite non-toxic, although it is slightly more toxic ($IC_{50}$=22.0 μM) as compared to dimer 39 ($IC_{50}$>88 μM) (Table 1).

In terms of physicochemical properties, all flavonoid monomers listed as active against either L. amazonensis (Table 3A) or L. donovani (Table 3B) are smaller than 39, and have fewer H-bond donors and acceptors. They also have a lower calculated ACDLogP (1.978 to 4.537) than 39 (5.104), except FM05 (5.011), FM17 (5.101) and FM19 (5.451). The lower ACDLogP values mean more water soluble; better partition between hydrophilic and hydrophobic phases and potentially easier to be absorbed orally. Indeed, these flavonoid monomers are highly water soluble (up to about 40 mg/mL of the hydrochloride salt) whereas 39 is not (up to about 4 mg/ml).

Importantly, the physicochemical properties of these flavonoid monomers are more favourable than 39 with molecular weights lower than or very close to 500. Number of H-bond acceptors were also lower (5 to 8) than 39 (10).

Selective Index Values

Selective index values of amine-containing flavonoid monomer FM01, FM05, FM09, FM13, FM14, FM16, FM17, FM18 and FM19 and known anti-leishmanial agents (pentamidine, amphotericin B and miltefosine) are demonstrated in Tables 3A and 3B. Specifically, selective index values were determined by dividing $IC_{50}$ toward to Raw264.7 cell line over $IC_{50}$ towards amastigotes (L. amazonensis LV78, and L donovani 39). All of the above flavonoid dimers have selective index higher than 10.

It is established in the art that selective index value smaller than 10 suggests probable non-selective cytotoxicity for the tested compounds (Weniger B et al Phytomedicine (2006)).

TABLE 3A

Selective cytotoxicity of amine-containing flavonoid monomers and known anti-leishmanial agents towards cutaneous leishmaniasis-causing L. amazonensis

| Compounds | Cytotoxicity ($IC_{50}$ (μM)) RAW264.7 (a) | Anti-amastigotes activity $IC_{50}$ (μM) L. amazonensis LV78 (b) | Selective index (a)/(b) | MW | HBA | HBD | ACD/LogP |
|---|---|---|---|---|---|---|---|
| 39 | >100 | 0.43 ± 0.09 | 232.6 | 724 | 10 | 0 | 5.104 |
| FM01 | 51.8 ± 3.3 | 1.8 ± 0.6 | 28.8 | 442 | 6 | 0 | 3.083 |
| FM09 | 18.9 ± 2.2 | 0.3 ± 0.1 | 63.0 | 508 | 7 | 0 | 3.156 |
| FM09.HCl | 35.0 ± 6.7 | 0.4 | 87.5 | ND | | | |

TABLE 3A-continued

Selective cytotoxicity of amine-containing flavonoid monomers and known anti-leishmanial agents towards cutaneous leishmaniasis-causing L. amazonensis

| Compounds | Cytotoxicity (IC$_{50}$ (μM)) RAW264.7 (a) | Anti-amastigotes activity IC$_{50}$ (μM) L. amazonensis LV78 (b) | Selective index (a)/(b) | MW | HBA | HBD | ACD/LogP |
|---|---|---|---|---|---|---|---|
| FM13 | >100 | 2.5 ± 0.5 | >40 | 427 | 5 | 0 | 4.537 |
| FM14 | 21.6 ± 1.9 | 1.9 ± 0.5 | 11.4 | 456 | 6 | 0 | 3.474 |
| FM17 | >100 | 3.4 ± 0.9 | >29.4 | 441 | 5 | 0 | 5.101 |
| FM18 | 52.6 ± 4.5 | 3.1 ± 0.1 | 17.0 | 412 | 5 | 0 | 4.183 |
| FM19 | >100 | 1.3 ± 0.6 | >76.9 | 506 | 5 | 0 | 5.451 |
| FM21 | 58.5* ± 4.3 | 4.5 | 13 | 505 | 8 | 1 | 1.582 |
| SSG | >11000 | 32.5 ± 17.6 | >338.5 | | | | |
| Pentamidine | 30.0 ± 5.0 | 15.7 ± 5.2 | 1.9 | | | | |
| Amphotericin B | 12.0 ± 2.5 | 0.055 ± 0.029 | 218.2 | | | | |
| Miltefosine | 20.0 ± 4.0 | 32.7 ± 26.9 | 0.6 | | | | |
| Paromomycin | >100 | ND | ND | | | | |

*IC$_{50}$ was measured using PEM instead of RAW264.7 macrophage cell line. Hydrogen bond donor and acceptors, ACD/LogP are predicted by ChemSpider (http://www.chemspider.com/)

TABLE 3B

Selective cytotoxicity of amine-containing flavonoid monomers and known anti-leishmanial agents towards visceral leishmaniasis-causing L. donovani (SSG-sensitive L. donovani HU3 and SSG-resistant L. donovani Ld39)

| Compounds | Cytotoxicity (IC$_{50}$ (μM)) RAW264.7 (a) | Anti-amastigotes activity IC$_{50}$ (μM) L. donovani HU3 (b) | Selective index (a)/(b) | Anti-amastigotes activity IC$_{50}$ (μM) L. donovani Ld39 (c) | Selective index (a)/(c) | MW | HBA | HBD | ACD/LogP |
|---|---|---|---|---|---|---|---|---|---|
| 39 | >100 | 0.2 ± 0.06 | >500 | 0.21 ± 0.06 | 47.6 | 724 | 10 | 0 | 5.104 |
| FM05 | 36.8 ± 4.4 | 3.5 ± 0.7 | 10.5 | >10 | <3.7 | 441 | 5 | 0 | 5.011 |
| FM09 | 18.9 ± 2.2 | 0.4 ± 0.1 | 47.3 | <0.37 | >51.1 | 508 | 7 | 0 | 3.156 |
| FM09.HCl | 35.0 ± 6.7 | 1.8 | 19.4 | ND | ND | ND | | | |
| FM13 | >100 | >10 | >10 | 3.3 | >33 | 427 | 5 | 0 | 4.537 |
| FM16 | >100 | ND | ND | 5.7 | >17.5 | 469 | 8 | 0 | 1.978 |
| FM20 | 15.8 | ND | ND | 0.7 | 22.6 | 325 | 5 | 2 | 2.224 |
| FM21 | 58.5* ± 4.3 | ND | ND | 0.33 | 177 | 505 | 8 | 1 | 1.582 |
| SSG | >11000 | ND | ND | 675 ± 75 | >16.3 | | | | |
| Pentamidine | 30.0 ± 5.0 | ND | ND | >30 | <1 | | | | |
| Amphotericin B | 12.0 ± 2.5 | ND | ND | 0.062 | 193.5 | | | | |
| Miltefosine | 20.0 ± 4.0 | ND | ND | 16 ± 6.4 | 1.3 | | | | |
| Paromomycin | >100 | ND | ND | 41 ± 1.1 | >2.4 | | | | |

Hydrogen bond donor and acceptors, ACD/LogP are predicted by ChemSpider (http://www.chemspider.com/)
*IC50 was measured using PEM instead of RAW264.7 macrophage cell line.

TABLE 3C

Selective cytotoxicity of FM09, FM01 and FM05 derivatives towards L. amazonensis and L. donovani HU3.

| Compounds | Cytotoxicity IC$_{50}$ (μM) Mouse fibroblast L929 | Cytotoxicity IC$_{50}$ (μM) Murine macrophages RAW264.7 | Cytotoxicity IC$_{50}$ (μM) Peritoneal macrophages PEM | Anti-Promastigote activity IC$_{50}$ (μM) L. amazonensis LV78 | Anti-Promastigote activity IC$_{50}$ (μM) L. donovani HU3 | Anti-Amastigote activity IC$_{50}$ (μM) L. amazonensis LV78 | Anti-Amastigote activity IC$_{50}$ (μM) L. donovani HU3 |
|---|---|---|---|---|---|---|---|
| FM09a | ND | ND | 10.4 ± 0.64 | 0.32 ± 0.05 | 0.47 ± 0.07 | 0.56 ± 0.21 | 0.3 5 |
| FM09a.HCl | 12.9 ± 2.4 | 8.51 ± 1.99 | ND | 0.77 ± 0.19 | 0.99 ± 0.19 | 0.35 ± 0.01 | 0.5 ± 0.02 |
| FM09b.HCl | 75.1 ± 13.6 | 90.5 ± 0.35 | ND | 8.08 ± 1.99 | 12.9 ± 7.32 | >10 | >10 |
| FM09c | ND | ND | 35.4 ± 1.05 | 3.19 ± 0.66 | 5.09 ± 1.13 | 1.95 ± 0.78 | 3.1 |
| FM09c.HCl | 39 ± 6.1 | 39.2 ± 8.4 | ND | 2.66 ± 0.3 | 4.97 ± 1.04 | 1.45 ± 0.31 | 2.9 ± 1.49 |
| FM09d | >100 | >100 | >100 | 35.3 ± 4.2 | 42.4 ± 7.65 | >10 | >10 |
| FM09e | 18.8 ± 0.95 | 22.1 ± 4.15 | ND | 7.41 ± 1.76 | 4.9 ± 0.78 | 2.4 ± 0.37 | 3.5 ± 0.48 |
| FM09g | 33.7 ± 10.6 | 34.3 ± 13.4 | ND | 28.08 ± 5.24 | 18.1 ± 4.88 | >10 | >10 |
| FM09h | 3.62 ± 0.51 | 3.83 ± 0.96 | 6.4 | 0.47 ± 0.07 | 1.09 ± 0.09 | 0.29 ± 0.05 | 0.3 ± 0.04 |
| FM09i | 2.28 ± 0.83 | 3.85 ± 0.66 | 4.5 | 0.08 ± 0.01 | 0.18 ± 0.07 | 0.27 ± 0.02 | 0.3 ± 0.05 |
| FM09k | 4.7 ± 0.71 | 4.46 ± 1.61 | 5.3 | 0.16 ± 0.05 | 1.06 ± 0.1 | 0.32 ± 0.02 | 0.3 ± 0.04 |
| FM09l | >100 | 76.4 ± 11.8 | 67.1 | 4.44 ± 1.24 | 4.74 ± 0.56 | 3.03 ± 0.41 | 4.5 ± 2.38 |
| FM09m | 23.9 ± 1.15 | 24.7 ± 2.55 | 28.4 | 17.62 ± 3.7 1 | 25.3 ± 3.94 | 4.46 ± 0.68 | 9.3 ± 0.56 |
| FM09m.HCl | ND | ND | 28.3 | 14.29 ± 3.3 | 18.2 ± 2.13 | 7.86 ± 2.15 | >10 |
| FM09p | 2.1 | 6.5 | 12.5 | 2.8 | 2.4 | ND | ND |

TABLE 3C-continued

Selective cytotoxicity of FM09, FM01 and FM05 derivatives towards *L. amazonensis* and *L. donovani* HU3.

| | Cytotoxicity IC$_{50}$ (μM) | | | Anti-Promastigote activity IC$_{50}$ (μM) | | Anti-Amastigote activity IC$_{50}$ (μM) | |
|---|---|---|---|---|---|---|---|
| Compounds | Mouse fibroblast L929 | Murine macrophages RAW264.7 | Peritoneal macrophages PEM | *L. amazonensis* LV78 | *L. donovani* HU3 | *L. amazonensis* LV78 | *L. donovani* HU3 |
| FM09am | ND | ND | ND | ND | ND | ND | ND |
| FM01a | 60.3 ± 2.3 | 82 ± 2.3 | ND | 11.73 ± 1.34 | 15.4 ± 5.98 | 8.74 ± 0.77 | 10 |
| FM01b | 95.8 ± 4.25 | 53.6 ± 6.5 | ND | 3.99 ± 0.99 | 6.15 ± 1.47 | 2.42 ± 0.69 | 3.5 ± 1.01 |
| FM05a | 58.9 ± 23.3 | 57.8 ± 23.9 | 17.6 | 2.97 ± 0.91 | 7.43 ± 2.15 | 3.57 ± 1.73 | 5.2 ± 1.68 |
| FM05b | 10.6 ± 1.13 | 7.73 ± 1.19 | 5.1 | 0.57 ± 0.17 | 0.89 ± 0.33 | 0.3 ± 0.06 | 0.7 ± 0.37 |

IC$_{50}$ values were presented as mean ± standard error of mean.
PEM = peritoneal elicited macrophages.
ND = not determined.

Effect of FM09 on Reactive Oxygen Species (ROS) Level

The ROS levels in both macrophage RAW264.7 and *L. amazonensis* promastigotes was measured by dichlorofluorescein diacetate (DCFDA) dye which is permeable to the cells. With oxidative stress, DCFDA would be oxidized to fluorescent DCF which is an indicator of intracellular ROS level. RAW cells or *L. amazonensis* promastigotes were pre-loaded with 10 μM of DCFDA for 1 hr, washed and exposed to 39, FM09, pentamidine and amphotericin B for different period of time (2, 4, 6, 8, 20, 46 and 72 hr). The fluorescence level was measured at the 520 nm using 485 nm as an excitation wavelength. 0.1% DMSO or 0.3% DMSO was used as a solvent control. The fluorescent value has been subtracted from non-DCFDA stained cells. The values were presented as mean±standard error of mean.

At 10 μM, only positive control, tert-butyl hydroperoxide, increased the ROS level by 2.2- to 2.3-fold after 2 hr, 4 hr and 6 hr (FIG. 1A). No ROS induction was detected in macrophages after exposing to compounds 39, FM09, pentamidine and amphotericin B as shown in FIG. 1A and Table 4A below.

TABLE 4A

| RAW264.7 | Relative fold (RF) | | | | |
|---|---|---|---|---|---|
| ROS Level | 2 hr | 4 hr | 6 hr | 8 hr | 20 hr |
| Stained control cells | 1.0 | 1.0 | 1.0 | 1.0 | 1.0 |
| Stained 0.1% DMSO | 0.9 | 0.8 | 0.8 | 0.8 | 0.8 |
| Stained 10 μM 39 | 0.9 | 0.9 | 0.9 | 0.8 | 0.9 |
| Stained 10 μM FM09 | 1.1 | 1.1 | 1.0 | 1.0 | 1.1 |
| Stained 10 μM amphotericin B | 1.4 | 1.4 | 1.4 | 1.2 | 1.0 |
| Stained 10 μM pentamidine | 0.9 | 0.9 | 0.9 | 0.8 | 0.8 |
| Stained 10 μM tert-butyl hydroperoxide | 2.3 | 2.3 | 2.2 | 1.9 | 1.8 |

Figure 1B:
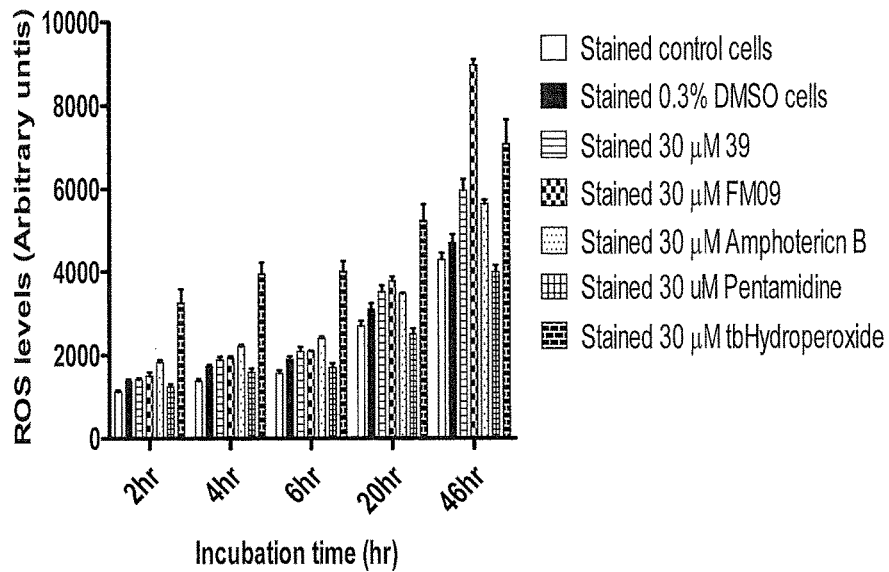

At 30 μM, tert-butyl hydroperoxide, still kept the high level of intracellular ROS (2.9 to 2.6-fold increase at 2 hr, 4 hr and 6 hr). Unexpectedly, a 2.1-fold increase in intracellular ROS level was observed in RAW264.7 cells upon exposure to the FM09 for 46 hr, but not to 39, pentamidine and amphotericin B as shown in FIG. 1B and Table 4B below, indicating that FM09 can kill the amastigotes by triggering intracellular oxidative stress of macrophage.

TABLE 4B

| RAW264.7 | Relative fold (RF) | | | | |
|---|---|---|---|---|---|
| ROS Level | 2 hr | 4 hr | 6 hr | 20 hr | 46 hr |
| Stained control cells | 1.0 | 1.0 | 1.0 | 1.0 | 1.0 |
| Stained 0.3% DMSO | 1.2 | 1.2 | 1.2 | 1.1 | 1.1 |
| Stained 30 μM 39 | 1.3 | 1.4 | 1.3 | 1.3 | 1.4 |
| Stained 30 μM FM09 | 1.3 | 1.4 | 1.3 | 1.4 | 2.1 |
| Stained 30 μM amphotericin B | 1.6 | 1.6 | 1.5 | 1.3 | 1.3 |
| Stained 30 μM pentamidine | 1.1 | 1.2 | 1.1 | 0.9 | 0.9 |
| Stained 30 μM tert-butyl hydroperoxide | 2.9 | 2.9 | 2.6 | 1.9 | 1.6 |

Figure 1C:
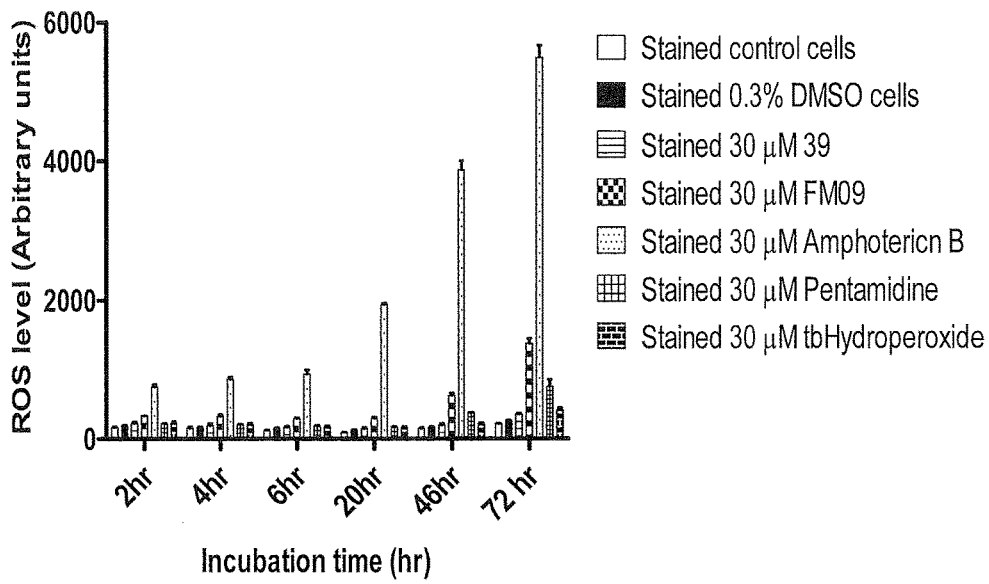
Figure 2A:
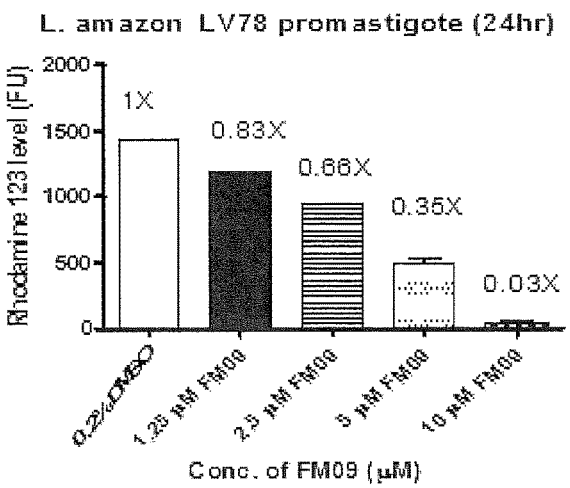
FIG. 2A-D shows the effect of FM09 on mitochondrial membrane potential of promastigote.
Figure 2B:
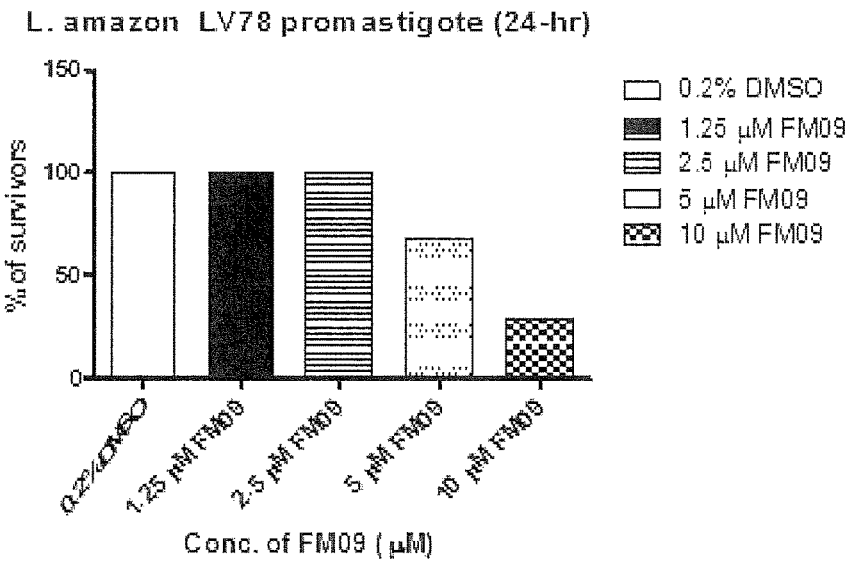
Figure 2C:
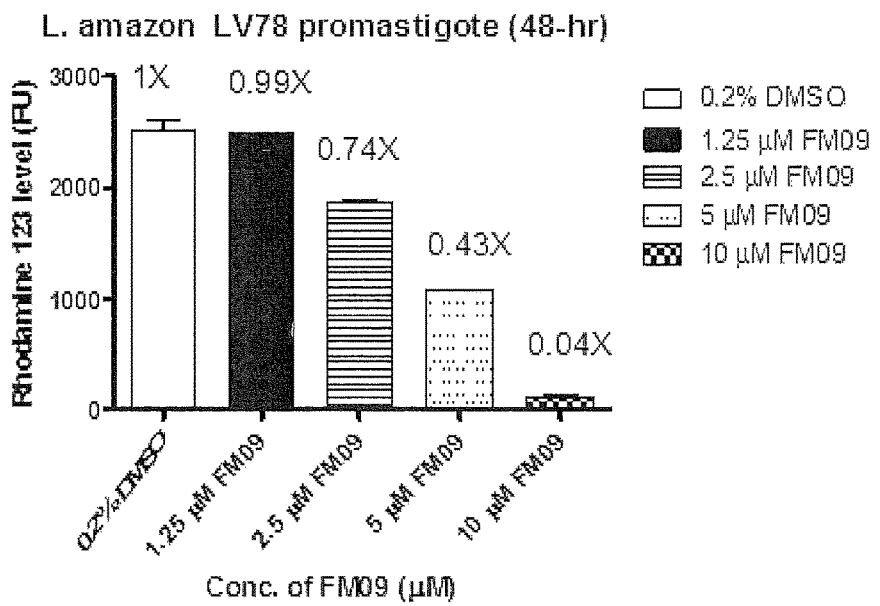
Figure 2D:
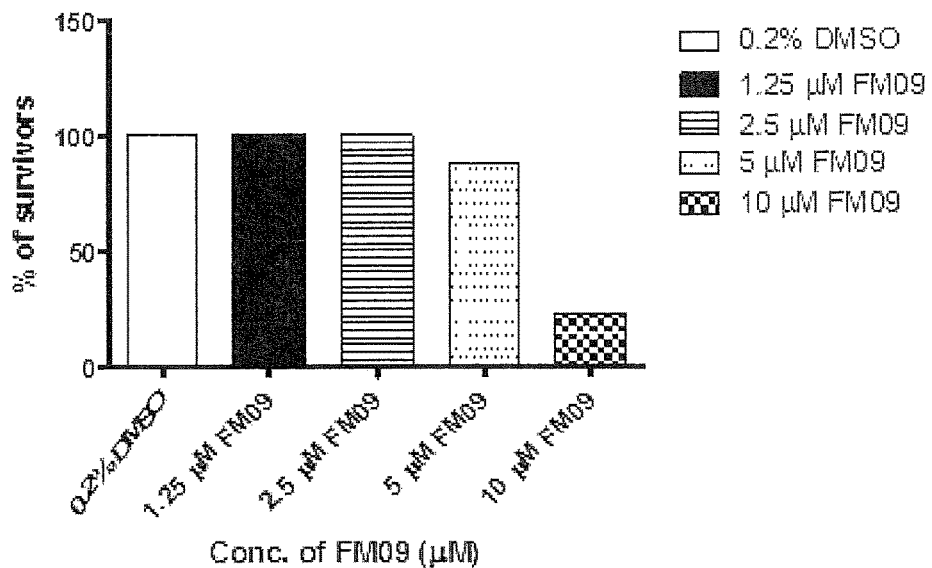

Other than macrophages, we also measured the intracellular ROS level of promastigotes as shown in FIG. 1C and Table 4C below.

TABLE 4C

| *L. amazon* LV78 promastigote | Relative fold (RF) | | | | | |
|---|---|---|---|---|---|---|
| ROS Level | 2 hr | 4 hr | 6 hr | 20 hr | 46 hr | 72 hr |
| Stained control cells | 1.0 | 1.0 | 1.0 | 1.0 | 1.0 | 1.0 |
| Stained 0.3% DMSO | 1.2 | 1.1 | 1.2 | 1.3 | 1.2 | 1.2 |
| Stained 30 μM 39 | 1.3 | 1.3 | 1.3 | 1.6 | 1.4 | 1.6 |
| Stained 30 μM FM09 | 2.0 | 2.1 | 2.3 | 3.2 | 4.3 | 6.2 |
| Stained 30 μM amphotericin B | 4.5 | 5.6 | 7.5 | 21 | 27.1 | 24.9 |
| Stained 30 μM pentamidine | 1.3 | 1.4 | 1.5 | 1.8 | 2.6 | 3.4 |
| Stained 30 μM tert-butyl hydroperoxide | 1.4 | 1.3 | 1.4 | 1.7 | 1.5 | 1.9 |

At 30 μM, FM09 (2.0 to 6.2-fold increase) and amphotericin B (4.5 to 24.9-fold increase) showed a time-dependent increase in the intracellular ROS level from 2 hr to 72 hr, but not 39 and tert-butyl hydroperoxide. Pentamidine induced about 2.6-fold and 3.4-fold increase in ROS level in promastigotes at 46 hr and 72 hr exposure. The data suggests that triggering oxidative stress in both parasites and macrophages is one of the mechanisms of FM09 for causing parasite death.

Effect of FM09 on Mitochondrial Membrane Potential

Mitochondria are a main source of intracellular ROS. The high level of ROS would damage the normal function of mitochondria. We measured the mitochondrial membrane potential of promastigote after FM09 treatment using mitochondria-specific fluorescent probe, rhodamine 123.

*L. amazonensis* promastigotes were cultivated in different concentration (0, 1.25, 2.5, 5 and 10 μM) of FM09 for 24 hr or 48 hr. The promastigotes were washed and exposed to rhodamine 123 (10 μg/mL) for 40 min. The level of rhodamine 123 accumulation was measured at 520 nm using 485 nm as an excitation wavelength. 0.2% DMSO was used as a solvent control. The values were presented as mean±standard error of mean.

A drop of mitochondrial potential was observed after promastigotes treating with different concentrations of FM09 for 24 hr (FIG. 1A) and 48 hr (FIG. 1C). The degree of mitochondrial depolarization is dose-dependent. In treated cells (0 to 5 μM of FM09), the decreased accumulation of rhodamine 123 is due to loss of mitochondrial potential in remaining live cells. It is found that about 100% of survivors were noted at 1.25 and 2.5 μM, and 68% and 88% at 5 μM of FM09 after 24 hr and 48 hr treatment, respectively (FIGS. 1B and 1D). Nevertheless, the marked reduction of rhodamine 123 accumulation at 10 μM of FM09 is due to measuring 29% and 23% of viable cells (FIGS. 1B and 1D). This data suggests that FM09 triggers oxidative stress in parasite followed by a loss of mitochondrial membrane potential.

Oral Bioavailability of Amine-Containing Flavonoid Monomers

A preliminary in vivo oral bioavailability study for the two flavonoid monomers was conducted for FM01 and FM05 having the structures shown below.

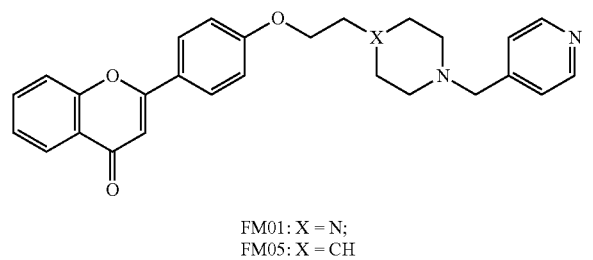

FM01: X = N;
FM05: X = CH

Figure 3:
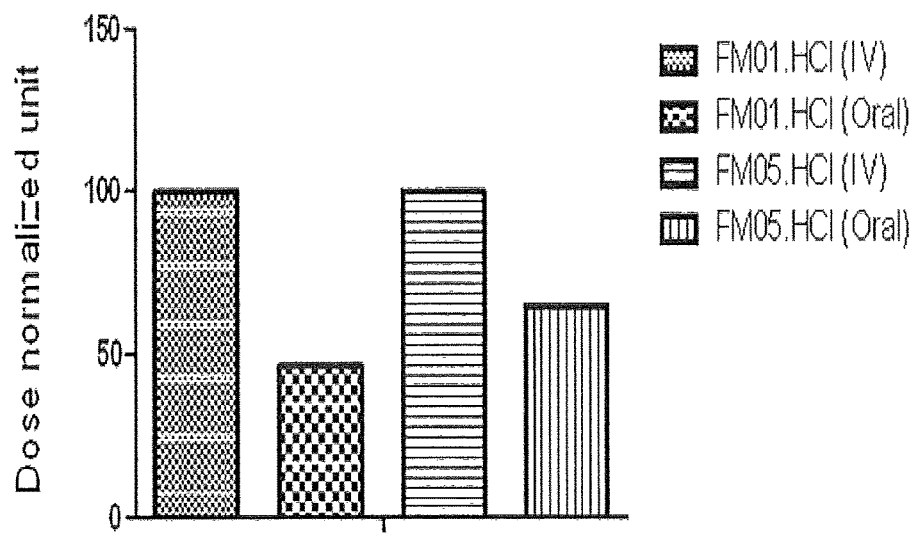
FIG. 3 shows the in vivo single time point plasma concentration comparison of FM01 hydrochloride salt and FM05 hydrochloride salt. FM01.HCl and FM05.HCl were administered to Balb/c mice via intravenous and passive oral administration. The blood plasma was collected at 30 minutes for LC-MSMS analysis and used for preliminary oral bioavailability screening. The corresponding plasma concentration was normalized by the administered dose for oral bioavailability calculation.

FM01 and FM05 hydrochloride salt was dissolved in saline and administered to Balb/c mice either orally or i.v. Plasma level of FM01 and FM05 was determined 30 minutes later by LC-MS and their identity confirmed by LC-MS/MS. Plasma concentration from oral feeding was divided by that obtained from i.v. administration. A higher ratio would suggest likely better oral bioavailability. In these preliminary studies, the ratios were 45% for FM01 and 64% for FM05 (FIG. 3).

Based on the result of the preliminary in vivo study, FM05 hydrochloride salt was selected for further investigation. FM05 hydrochloride salt was dissolved in saline at 4 mg/ml and administered to male balb/c at 42 mg/kg. Blood plasma samples were collected at various time points for pharmacokinetics analysis (n=2 to 3 for each time point).

Figure 4:
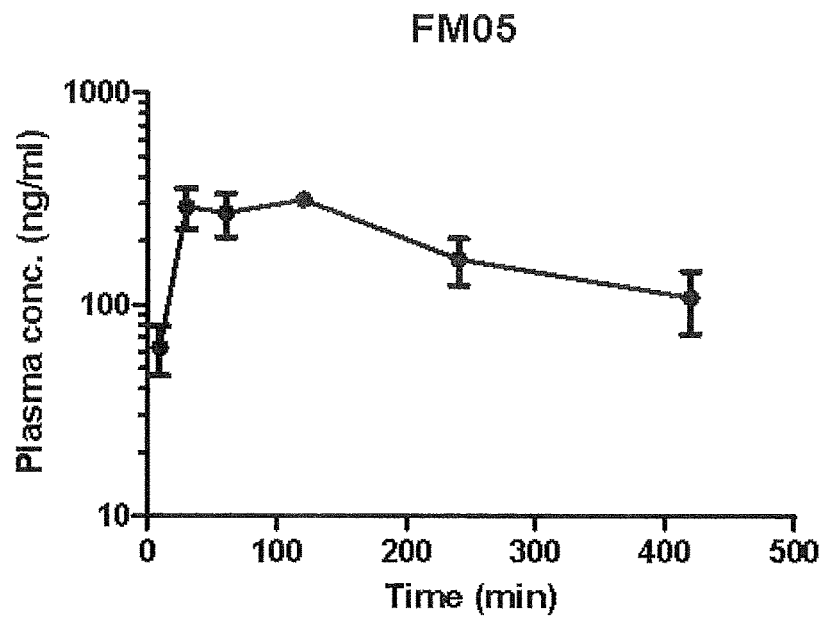
FIG. 4 shows the plasma concentration profile of FM05 in mice.

A 7-hour pharmacokinetics profile of FM05 in Balb/c mice is obtained and shown in FIG. 4 and Table 5 below. As shown, FM05 is orally bioavailable with rapid absorption (half life of distribution and absorption=25 minutes) as suggested by the high plasma concentration (Cmax=313 ng/ml) within early time points (Tmax at 120 minutes). Elimination half life was 202 minutes, suggesting that FM05 is metabolically stable in systemic circulation via oral administration.

TABLE 5

Pharmacokinetics parameter of FM05 hydrochloride salt. Non-compartmental pharmacokinetics analysis was done by PK Solutions 2.0 (Summit Research Service, Ashland, U.S.A)

| Parameter | Unit | Oral Total value |
|---|---|---|
| Dose | mg/kg | 42 |
| AUC(0-7 hr) | ng-min/ml | 83089 |
| Half-life (Elimination) | min | 202 |
| Half-life (Distribution and absorption) | min | 25 |
| MRT (area) | min | 321 |
| Cmax (obs) | ng/ml | 312.8 |
| Tmax (obs) | min | 120 |

REFERENCES

1. Wong I L, Chan K F, Burkett B A, Zhao Y, Chai Y, Sun H, Chan T H, Chow L M. 2007. Flavonoid dimers as bivalent modulators for pentamidine and sodium stibogluconate resistance in *leishmania*. Antimicrob Agents Chemother 51:930-940.
2. Wong I L, Chan K F, Zhao Y, Chan T H, Chow L M. 2009. Quinacrine and a novel apigenin dimer can synergistically increase the pentamidine susceptibility of the protozoan parasite *Leishmania*. J Antimicrob Chemother 63:1179-1190.
3. Weniger B, Vonthron-Senecheau C, Kaiser M, Brun R, Anton R. 2006. Comparative antiplasmodial, leishmanicidal and antitrypanosomal activities of several biflavonoids. Phytomedicine: international journal of phytotherapy and phytopharmacology 13:176-180.

We claim:

1. An anti-leishmanial compound having the general formula of:

Flavonoid-X—$NR^1R^2$ or Flavonoid-X—$R^1R^2$, or a pharmaceutically acceptable salt thereof,
wherein:
the flavonoid is selected from the group consisting of flavone, flavonol, flavanone, and isoflavonoid;
X is a linker, wherein each linker independently comprises one or more groups selected from the group consisting of alkylene, ethyleneoxy, propyleneoxy, butyleneoxy, alkylC(O)—, ethylene amine, propylene amine, butylene amine, alkylcyclic amine, alkylcyclic diamine, or a combination thereof;
wherein:
(i) $R^1$ is independently selected from the group consisting of H, —$(CH_2)_n$-aryl, and —$(CH_2)_n$-heteroaryl which may be optionally substituted; $R_2$ is independently selected from the group consisting of H, —(CH2)n-aryl, and —(CH2)n-heteroaryl which may be optionally substituted; or
(ii) $R^1R^2$ forms a cyclic compound with a general structure of —$(CH_2)_n$—Y—$(CH_2)_m$— wherein Y is $CH_2$, O, or $NR^1$, any of which may be optionally substituted; and wherein n and m are independently selected from an integer between 1 to 6.

2. The anti-leishmanial compound according to claim 1, wherein $R^1$ is independently selected from hydrogen, benzyl, pyrimidyl-CH$_2$—, quinolyl-CH$_2$—, 2-pyridinyl-CH$_2$—, or 4-pyridinyl-CH$_2$—.

3. The anti-leishmanial compound according to claim 1, wherein $R^2$ is independently selected from hydrogen, benzyl, pyrimidyl-CH$_2$—, quinolyl-CH$_2$—, 2-pyridinyl-CH$_2$—, or 4-pyridinyl-CH$_2$—.

4. The anti-leishmanial compound according to claim 1, wherein $R^1$ and $R^2$ are both 2-pyridinyl-CH$_2$ which are each independently substituted with one or more optionally substituted alkyl, optionally substituted alkoxy, halogen, optionally substituted aryl, or optionally substituted heteroaryl groups.

5. The anti-leishmanial compound according to claim 1, wherein $R^1$ and $R^2$ are both 4-pyridinyl-CH$_2$— which are each independently substituted with one or more optionally substituted alkyl, optionally substituted alkoxy, halogen, optionally substituted aryl, or optionally substituted heteroaryl groups.

6. The anti-leishmanial compound according to claim 1, wherein X is a linker selected from the group consisting of ethyleneoxy, propyleneoxy, and butyleneoxy.

7. The anti-leishmanial compound according to claim 6, wherein $R^1$ and/or $R^2$ are selected from pyrimidyl-CH$_2$—, quinolyl-CH$_2$—, 2-pyridinyl-CH$_2$—, or 4-pyridinyl-CH$_2$— groups optionally substituted with one or more optionally substituted alkyl, optionally substituted alkoxy, halogen, optionally substituted aryl, or optionally substituted heteroaryl groups.

8. The anti-leishmanial compound according to claim 1, wherein X is a linker selected from the group consisting of 4-piperidinylmethoxy, 4-piperidinylethoxy, and piperazinylethoxy.

9. The anti-leishmanial compound according to claim 8, wherein $R^1$ is a 2-pyridinyl-CH$_2$— or 4-pyridinyl-CH$_2$— group optionally substituted with one or more optionally substituted alkyl, optionally substituted alkoxy, halogen, optionally substituted aryl, or optionally substituted heteroaryl groups.

10. The anti-leishmanial compound according to claim 1, wherein the compound is selected from the group consisting of:

| | | |
|---|---|---|
| FM09a | 2-(4-(2-(2-(bis((3,4-dimethoxypyridin-2-yl)methyl)amino)ethoxy)ethoxy)phenyl)-4H-chromen-4-one | 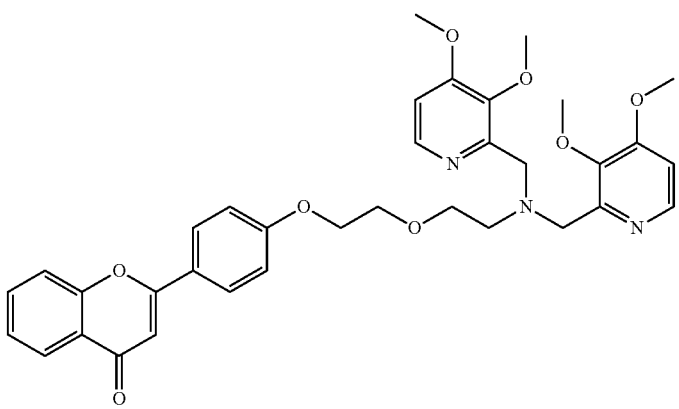 |

FM09a
C$_{35}$H$_{37}$N$_3$O$_8$
Exact Mass: 627.26

| | | |
|---|---|---|
| FM09b | 2-(4-(2-(2-(bis(pyridin-3-ylmethyl)amino)ethoxy)ethoxy)phenyl)-4H-chromen-4-one | 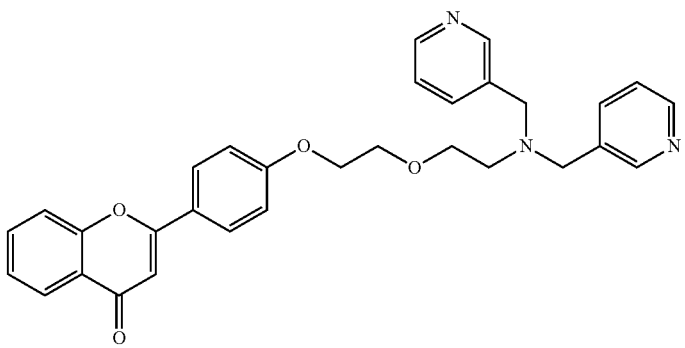 |

FM09b
C$_{31}$H$_{29}$N$_3$O$_4$
Exact Mass: 507.22

-continued
| | | |
|---|---|---|
| FM09c | 2-(4-(2-(2-(bis((3-fluoropyridin-2-yl)methyl)amino)ethoxy)ethoxy)phenyl)-4H-chromen-4-one | 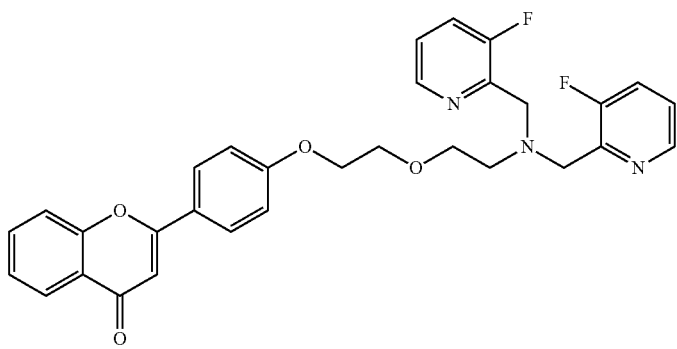<br>FM09c<br>$C_{31}H_{27}F_2N_3O_4$<br>Exact Mass: 543.20 |
| FM09d | 2-(4-(2-(2-(bis(pyrimidin-2-ylmethyl)amino)ethoxy)ethoxy)phenyl)-4H-chromen-4-one | 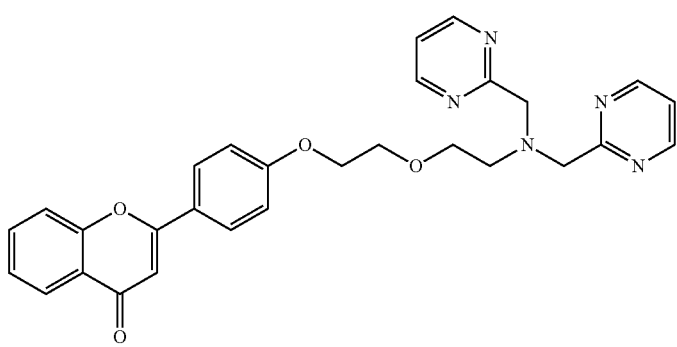<br>FM09d<br>$C_{29}H_{27}N_5O_4$<br>Exact Mass: 509.21 |
| FM09e | 2-(4-(2-(2-(bis((6-methylpyridin-2-yl)methyl)amino)ethoxy)ethoxy)phenyl)-4H-chromen-4-one | 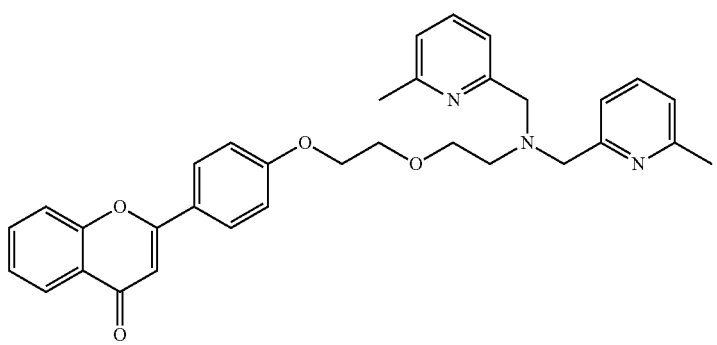<br>FM09e<br>$C_{33}H_{33}N_3O_4$<br>Exact Mass: 535.25 |

-continued

| | | |
|---|---|---|
| FM09g | 2-(4-(2-(2-(bis((3-chloropyridin-2-yl)methyl)amino)ethoxy)ethoxy)phenyl)-4H-chromen-4-one | 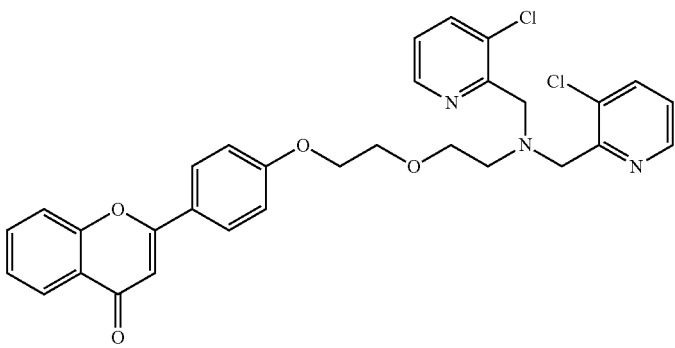<br>FM09g<br>C$_{31}$H$_{27}$Cl$_2$N$_3$O$_4$<br>Exact Mass: 575.14 |
| FM09h | 2-(4-(2-(2-(bis((3-methyl-4-(2,2,2-trifluoroethoxy)pyridin-2-yl)methyl)amino)ethoxy)ethoxy)phenyl)-4H-chromen-4-one | 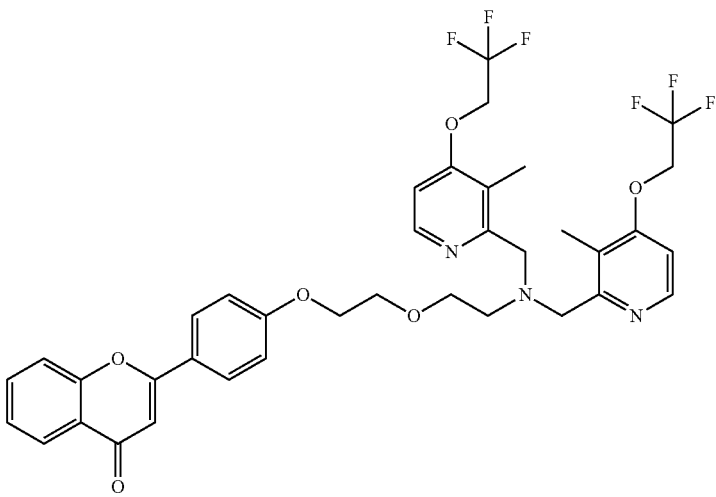<br>FM09h<br>C$_{37}$H$_{35}$F$_6$N$_3$O$_6$<br>Exact Mass: 731.24 |
| FM09i | 2-(4-(2-(2-(bis((4-methoxy-3,5-dimethylpyridin-2-yl)methyl)amino)ethoxy)ethoxy)phenyl)-4H-chromen-4-one | 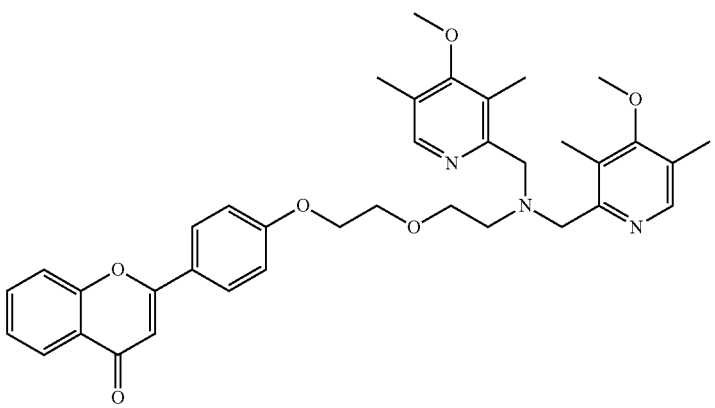<br>FM09i<br>C$_{37}$H$_{41}$N$_3$O$_6$<br>Exact Mass: 623.30 |

-continued
| FM09k | 2-(4-(2-(2-(bis((4-(3-methoxypropoxy)-3-methylpyridin-2-yl)methyl)amino)ethoxy)ethoxy)phenyl)-4H-chromen-4-one | 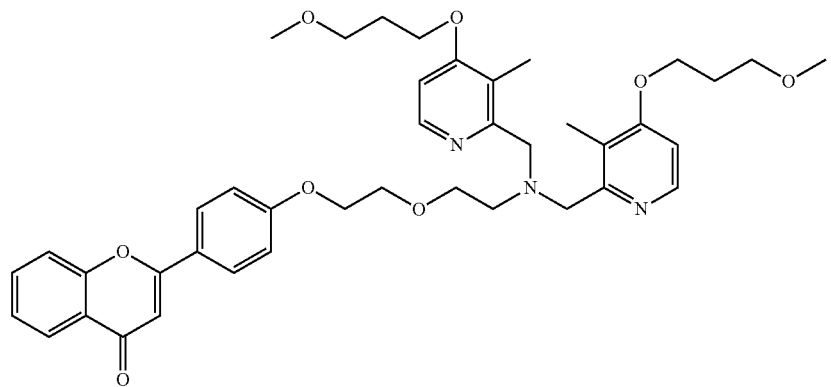 FM09k<br>$C_{41}H_{49}N_3O_8$<br>Exact Mass: 711.35 |
| --- | --- | --- |
| FM09l | 2-(4-(2-(2-(bis(quinolin-2-ylmethyl)amino)ethoxy)ethoxy)phenyl)-4H-chromen-4-one | 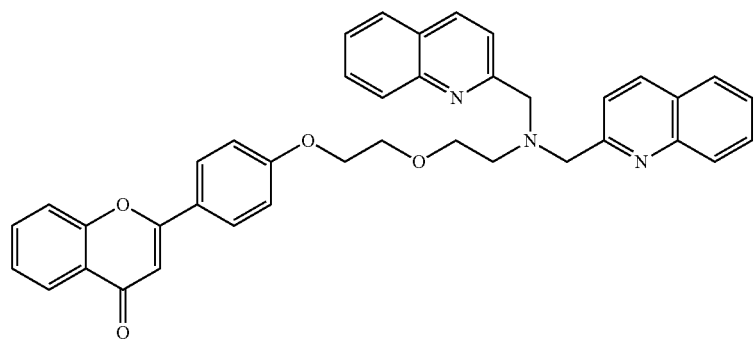 FM09l<br>$C_{39}H_{33}N_3O_4$<br>Exact Mass: 607.25 |
| FM09m | 2-(4-(2-(2-((pyridin-2-ylmethyl)amino)ethoxy)ethoxy)phenyl)-4H-chromen-4-one | 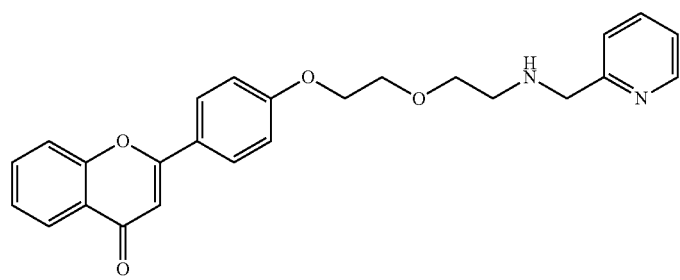 FM09m<br>$C_{25}H_{24}N_2O_4$<br>Exact Mass: 416.17 |

-continued

| | | |
|---|---|---|
| FM09p | 2-(4-(2-(2-((di(pyridin-2-yl)methyl)amino)ethoxy)ethoxy)phenyl)-4H-chromen-4-one | 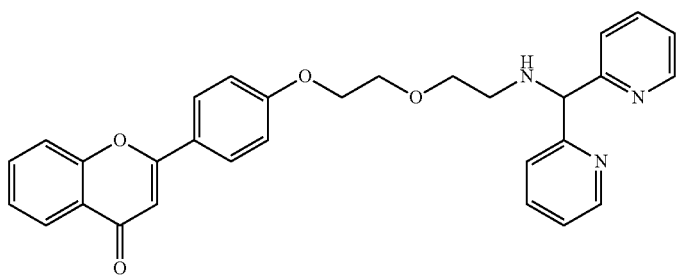<br>FM09p<br>$C_{30}H_{27}N_3O_4$<br>Exact Mass: 493.20 |
| FM09am | 2-(4-(2-(2-(((3,4-dimethoxypyridin-2-yl)methyl)amino)ethoxy)ethoxy)phenyl)-4H-chromen-4-one | 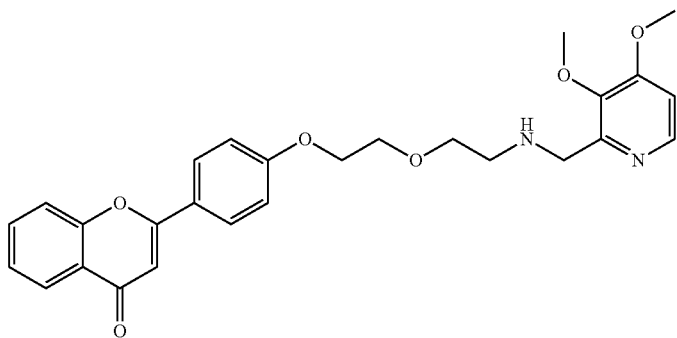<br>FM09am<br>$C_{27}H_{28}N_2O_6$<br>Exact Mass: 476.19 |
| FM01a | 2-(4-(2-(4-(pyridin-2-ylmethyl)piperazin-1-yl)ethoxy)phenyl)-4H-chromen-4-one | 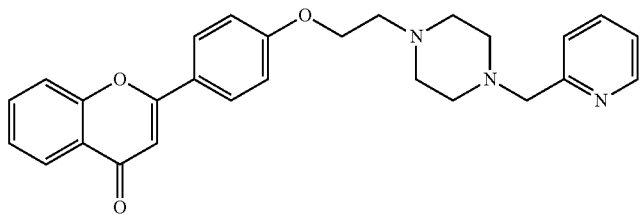<br>FM01a<br>C27H27N3O3<br>Exact Mass: 441.21 |
| FM01b | 2-(4-(2-(4-((3,4-dimethoxypyridin-2-yl)methyl)piperazin-1-yl)ethoxy)phenyl)-4H-chromen-4-one | 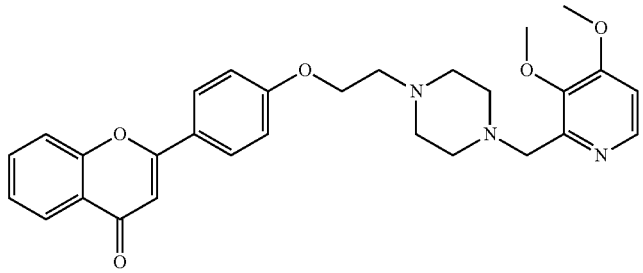<br>FM01b<br>$C_{29}H_{31}N_3O_5$<br>Exact Mass: 501.23 |

-continued

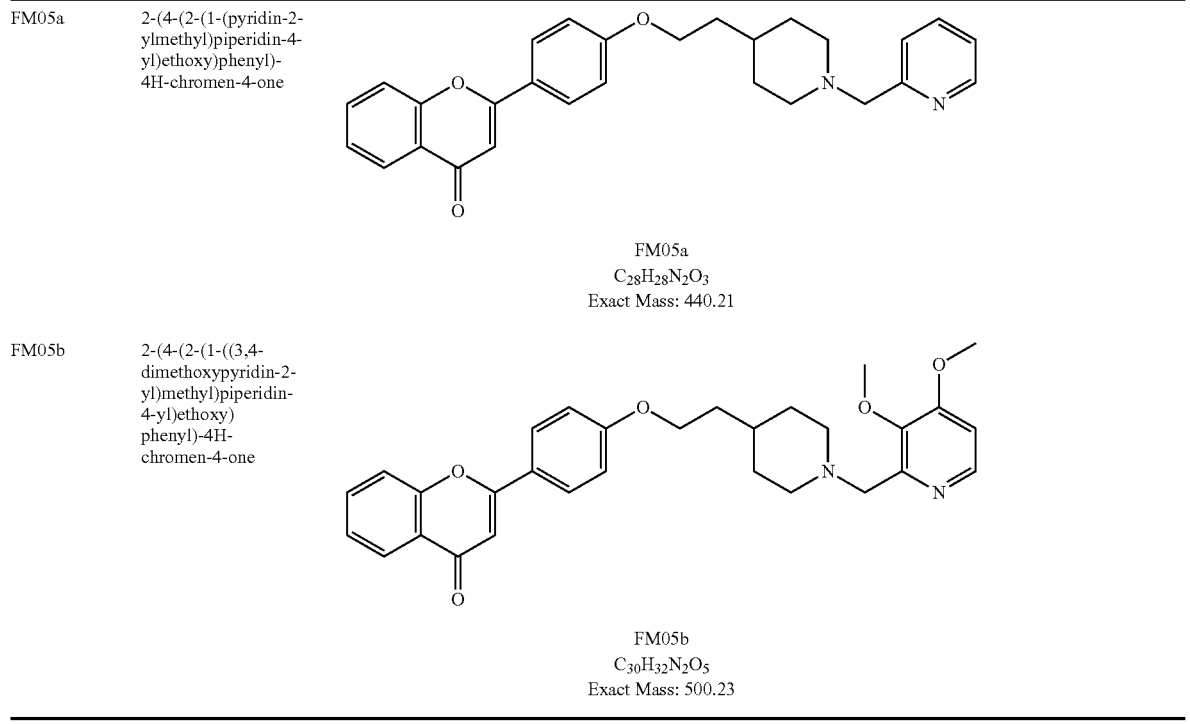

| FM05a | 2-(4-(2-(1-(pyridin-2-ylmethyl)piperidin-4-yl)ethoxy)phenyl)-4H-chromen-4-one |
| FM05b | 2-(4-(2-(1-((3,4-dimethoxypyridin-2-yl)methyl)piperidin-4-yl)ethoxy)phenyl)-4H-chromen-4-one |

FM05a
$C_{28}H_{28}N_2O_3$
Exact Mass: 440.21

FM05b
$C_{30}H_{32}N_2O_5$
Exact Mass: 500.23

11. A method of inhibiting a parasitic disease—caused by the genus *Leishmania*—comprising the step of administering an effective amount of a compound as defined in claim 1, or a pharmaceutically acceptable salt thereof.

12. The method of claim 11, wherein the parasitic diseases is caused by one of the parasites selected from the group consisting of *L. donovani, L. amazonensis, L. tarentolae, L. tropica, L. enriettii, L. mexicana,* and *L. major.*

13. The method of claim 11, wherein the parasitic disease is visceral leishmaniasis.

14. The method of claim 11, wherein the parasitic disease is cutaneous leishmaniasis.

15. A method of treating a protozoan infection—selected from the group consisting of malaria, Chagas disease, trypanosomiasis, and toxoplasmosis—comprising the step of administering an effective amount of a compound as defined in claim 1, or a pharmaceutically acceptable salt "or solvate" thereof.

16. A pharmaceutical composition comprising an effective amount of a compound as defined in claim 1, or a pharmaceutically acceptable salt "or solvate" thereof and a pharmaceutically acceptable carrier.

17. The pharmaceutical composition of claim 16 further comprising an additional anti-leishmanial agent selected from the group consisting of sodium stibogluconate, meglumine antimoniate, amphotericin B, miltefosine, pentamidine and Paromomycin.

* * * * *